(12) United States Patent
Nagasawa et al.

(10) Patent No.: US 7,422,863 B2
(45) Date of Patent: Sep. 9, 2008

(54) MOLTING HORMONE RECEPTOR AND METHOD FOR SCREENING LIGAND TO THE RECEPTOR

(75) Inventors: Hiromichi Nagasawa, Tokyo (JP); Norihiko Izawa, Tokyo (JP); Yutaka Kurihara, Tokyo (JP); Shinji Nagata, Tokyo (JP); Takafumi Maruyama, Chiba (JP)

(73) Assignees: Kumiai Chemical Industry Co., Ltd., Tokyo (JP); Hiromichi Nagasawa, Tokyo (JP)

( * ) Notice: Subject to any disclaimer, the term of this patent is extended or adjusted under 35 U.S.C. 154(b) by 186 days.

(21) Appl. No.: 10/544,673

(22) PCT Filed: Feb. 2, 2004

(86) PCT No.: PCT/JP2004/001006

§ 371 (c)(1),
(2), (4) Date: Aug. 4, 2005

(87) PCT Pub. No.: WO2004/070028

PCT Pub. Date: Aug. 19, 2004

(65) Prior Publication Data

US 2006/0211043 A1   Sep. 21, 2006

(30) Foreign Application Priority Data

Feb. 7, 2003   (JP) ............................. 2003-031606

(51) Int. Cl.
*C07K 14/72* (2006.01)
*C07K 1/00* (2006.01)
*C07K 14/00* (2006.01)
*C07K 17/00* (2006.01)
*G01N 33/53* (2006.01)
*G01N 33/566* (2006.01)
*C12P 21/04* (2006.01)
*C12P 21/06* (2006.01)
*A61K 38/24* (2006.01)
*A61K 38/27* (2006.01)

(52) U.S. Cl. .................. 435/7.8; 435/7.1; 435/71.2; 435/69.1; 530/350; 530/417; 530/399; 436/501

(58) Field of Classification Search ............... None
See application file for complete search history.

(56) References Cited

U.S. PATENT DOCUMENTS 6,379,945 B1 * 4/2002 Jepson et al. ............... 435/243
2002/0037556 A1 * 3/2002 Zitzmann et al. .......... 435/69.1

FOREIGN PATENT DOCUMENTS

EP   1176152 A2   1/2002
EP   1 182 212 A2   2/2002
WO   WO-96/37609 A1   11/1996
WO   WO-00/15791 A1   3/2000
WO   WO-01/70816 A2   9/2001
WO   WO-02/061102 A2   8/2002

OTHER PUBLICATIONS

Riddiford et al. 2001. Vitamins and Hormones 60:1-73, only p. 6 is enclosed.*
Helmrich. 2001.The Biochemistry of Cell Signaling. Chapter 11, p. 192, Oxford University Press.*
Wells, 1990, Biochemistry 29:8509-8517.*
Ngo et al., 1994, The Protein Folding Problem and Tertiary Structure Prediction, Merz et al., eds, Birkhauser, Boston, pp. 491-495.*
Kenichi Mikitani "A novel Ecdysteroid Responsive Reporter Plasmid Regulated by the 5'-Upstream Region of the *Drosophila melanogaster* (Diptera: Drosophilidae) Acetylcholinesterase Gene" (Appl. Entomol. Zool. 31 (4): 1996 p. 531-536).
Kenichi Mikitani "Ecdysteroid Receptor Binging Activity and Ecdysteroid Agonist Activity at the Level of Gene Expression are Correlated with the Activity of Dibenzoyl Hydrazines in Larvae of *Bombyx mori*" (J. Insect Physiol. vol. 42, No. 10: 1996 p. 937-941).
Kenichi Mikitani "A New Nonsteroidal Chemical Class of Ligand for the Ecdysteroid Receptor 3,5-di-tert-butyl-4-hydroxy-N-isobutyl-benzamide Shows Apparent Insect Molting Hormone Activities at Molecular and Cellular Levels" (Biochemical and Biophysical Research Communications 227: 1996 p. 427-432).
Andi Trisyono et al. "Establishment and Characterization of an *Ostrinia nubilalis* Cell Line, and Its Response to Ecdysone Agonists" ( In Vitro Cell. Dev. Biol.- Animal 36:2000 p. 400-404).
Maruyama et al., Japan Society for Bioscience, Biotechnology, and Agrochemistry, 2002 Nendo Taikai Koen Yoshishu (2002), p. 280.
Fujiwara et al., Insect Biochem. Mol. Biol. (1995), vol. 25, No. 7, pp. 845-856.
Martinez et al., Insect Biochem. Mol. Biol. (1999), vol. 29, No. 10, pp. 915-930.
Tzertzinis et al., J. Mol. Biol. (1994), vol. 238, No. 3, pp. 479-486.
Perera et al., Dev. Genet. (1998), vol. 22, No. 2, pp. 169-179.
Maruyama et al., Japan Society for Bioscience, Biotechnology, and Agrochemistry, 2003 Nendo Taikai Koen Yoshishu, Mar. 5, 2003, p. 268.

* cited by examiner

Primary Examiner—Lorraine Spector
Assistant Examiner—Shulamith H Shafer
(74) Attorney, Agent, or Firm—Birch, Stewart, Kolasch & Birch, LLP

(57) ABSTRACT

The present invention provides a completely novel molting hormone receptor, which is used for efficiently screening a substance that can be applied to a disinfestant or the like. An insect molting hormone receptor comprising the following polypeptide (a) and polypeptide (b) or (c):

(a) a polypeptide having the amino acid sequence shown in SEQ ID NO: 1;
(b) a polypeptide having the amino acid sequence shown in SEQ ID NO: 2; and
(c) a polypeptide having the amino acid sequence shown in SEQ ID NO: 3.

15 Claims, 27 Drawing Sheets

Fig. 1
(a)
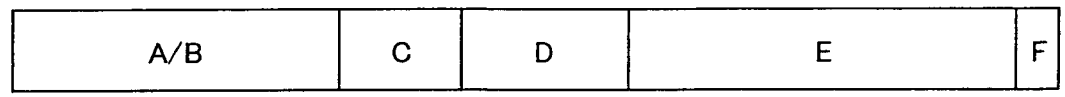
(b)
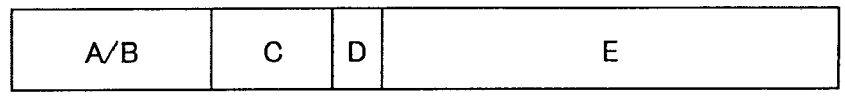

Fig. 2

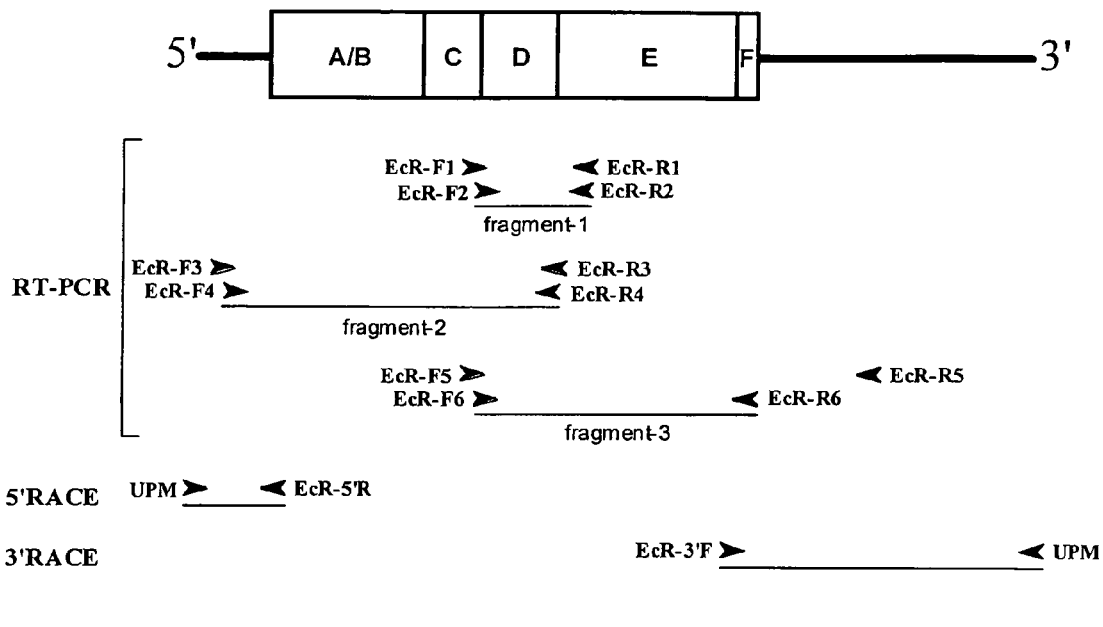

| Primer | Sequence |
|---|---|
| EcR-F1 | 5'-CTGGCGGTIGGIATGMGNCC-3' |
| EcR-F2 | 5'-GTCGGGATGMGICCNGARTG-3' |
| EcR-R1 | 5-'CCCTTCGCGAAYTCNACDAT-3' |
| EcR-R2 | 5'-TCGACGATIARYTGNACNGT-3' |
| EcR-F3 | 5'-TCGCGTRCTYTTCTCACCTG-3' |
| EcR-F4 | 5'-CGTRCTYTTCTCACCTGTTG-3' |
| EcR-R3 | 5'-TTCCTCATCTTCATCCGACTCTGTGAT-3' |
| EcR-R4 | 5'-CATCTTCATCCGACTCTGTGATTCTTC-3' |
| EcR-F5 | 5'-CAGTAGATGATCACATGCCT-3' |
| EcR-F6 | 5'-ATGATCACATGCCTCCCATT-3' |
| EcR-R5 | 5'-TTYCAYCCAATAGAAACATC-3' |
| EcR-R6 | 5'-GTCTATGAGCGTTCTCTCTCCT-3' |
| EcR-3'F | 5'-GTTCCTCGAGGAGATCTGGGACGTG-3' |
| UPM | 5'-CTAATACGACTCACTATAGGGCAAGCAGTGGTAACAACGCAGAGT-3' |
| EcR-5'R | 5'-ATCCTCCGGCAAAGGCTTTCACTTCAC-3' |

Fig. 3

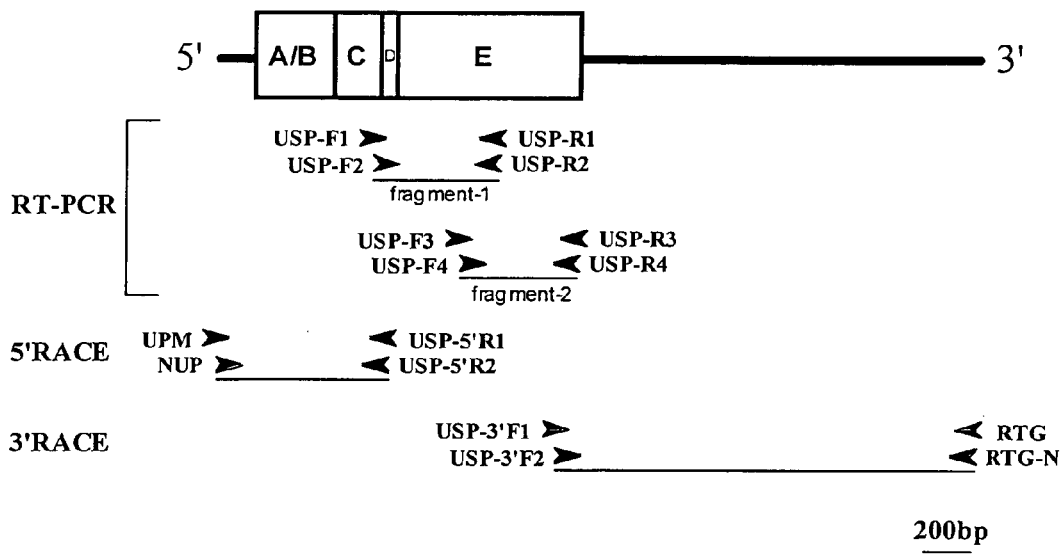

| Primer | Sequence |
|---|---|
| USP-F1 | 5'-ATCAGAARTGTCTNGCNTGC-3' |
| USP-F2 | 5'-ARTGTCTIGCNTGCGGNATG-3' |
| USP-R1 | 5'-CTCGGACAGCACGCGRTCRA-3' |
| USP-R2 | 5'-GACAGCACGCGRTCRAADAT-3' |
| USP-F3 | 5'-CGATCGCITGGMGNTCNATG-3' |
| USP-F4 | 5'-TCGCITGGMGITCNATGGAG-3' |
| USP-R3 | 5'-CTACAKGATIYTGGTRTCGA-3' |
| USP-R4 | 5'-CAKGATIYTGGTRTCGATSG-3' |
| USP-5'R1 | 5'-TGAGCTGCTTGGATGTGCAT-3' |
| USP-5'R2 | 5'-GCTGCTTGGATGTGCATCCT-3' |
| UPM | 5'-CTAATACGACTCACTATAGGGCAAGCAGTGGTAACAACGCAGAGT-3' |
| NUP | 5'-AAGCAGTGGTAACAACGCAGAGT-3' |
| USP-3'F1 | 5'-CGCTCCATCTCGCTGAAGAGCTTC-3' |
| USP-3'F2 | 5'-GTCCATCGCGTCCTACATC-3' |
| RTG | 5'-AACTGGAAGAATTCGCGGCCG-3' |
| RTG-N | 5'-TGGAAGAATTCGCGGCCGCAG-3' |

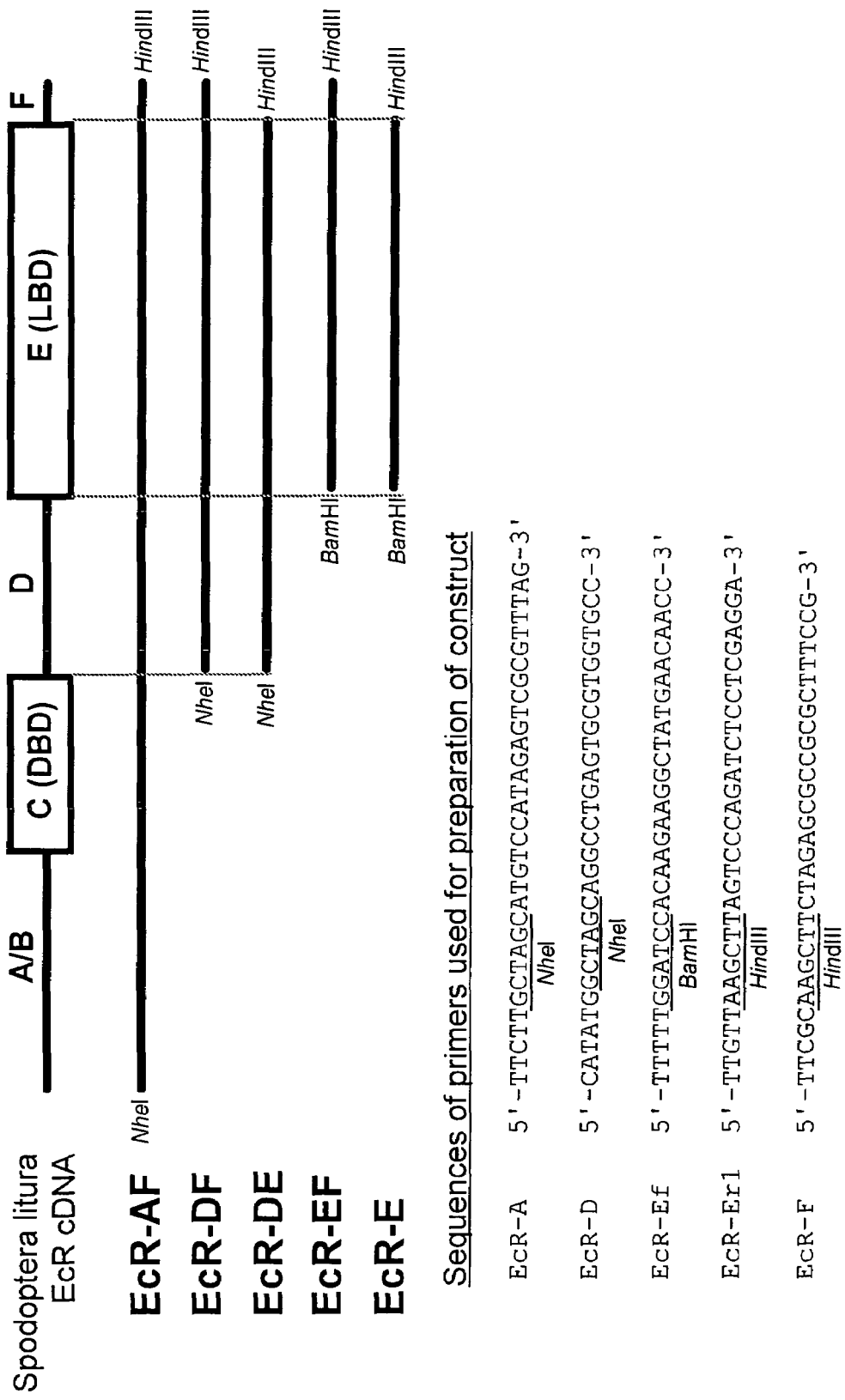

1 : EcR-AF- supernatant
2 : EcR-AF- precipitate
3 : EcR-DF- supernatant
4 : EcR-DF- precipitate
5 : EcR-DE- supernatant
6 : EcR-DE- precipitate
7 : EcR-EF- supernatant
8 : EcR-EF- precipitate
9 : EcR-E- supernatant
10 : EcR-E- precipitate
11 : control- supernatant
12 : control- precipitate Fig. 7
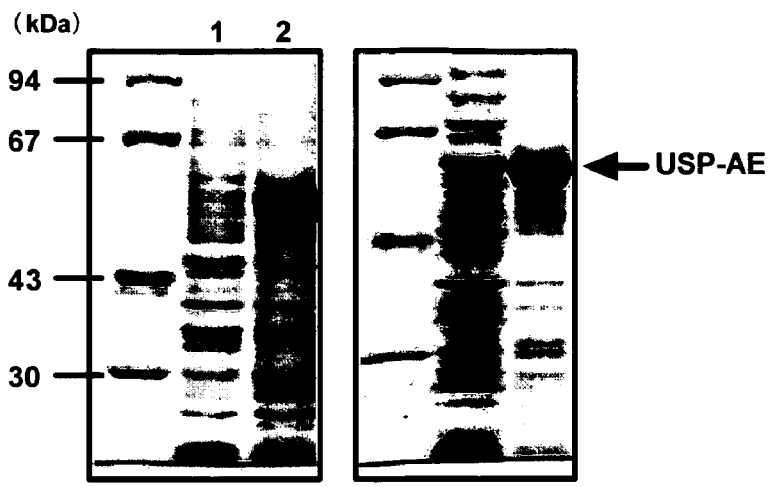
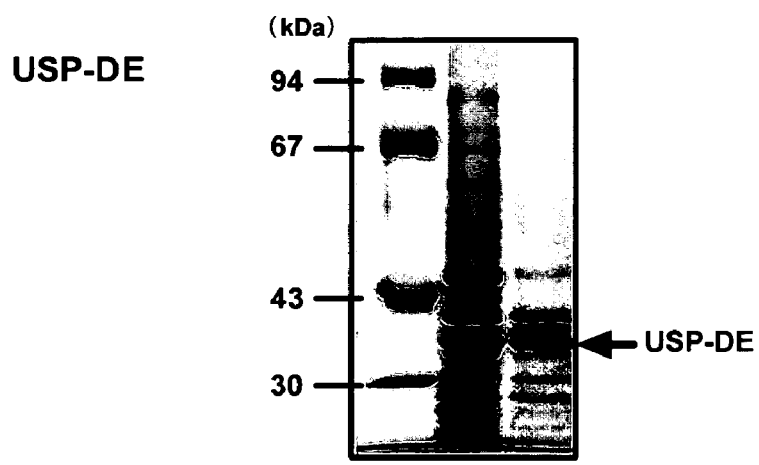
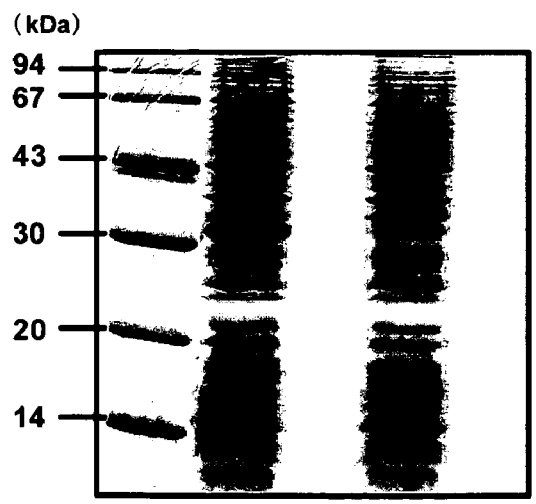

T: trypsin autodigest product

▽: EcR-AF trypsin digest product
(m/z)
1016.6
1358.1
1394.3
1491.8
2037.9
2142.3
2242.3
2361.4

T: trypsin autodigest product

▽: EcR-DF trypsin digest product
(m/z)
1016.7
1394.8
2038.0
2143.4
2346.0

T: trypsin autodigest product

▽: EcR-DE trypsin digest product
(m/z)
1017.1
1394.7
2038.0
2143.0
2346.1

T: trypsin autodigest product

▽: EcR-EF trypsin digest product
(m/z)
1016.6
1536.0
1792.8
2038.0
2346.0

Fig. 10
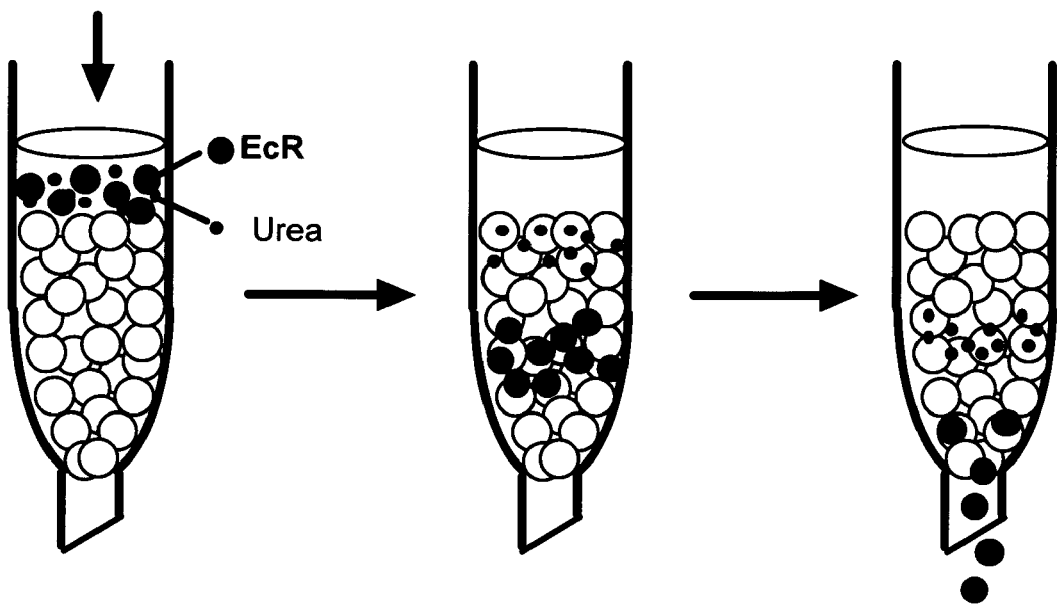
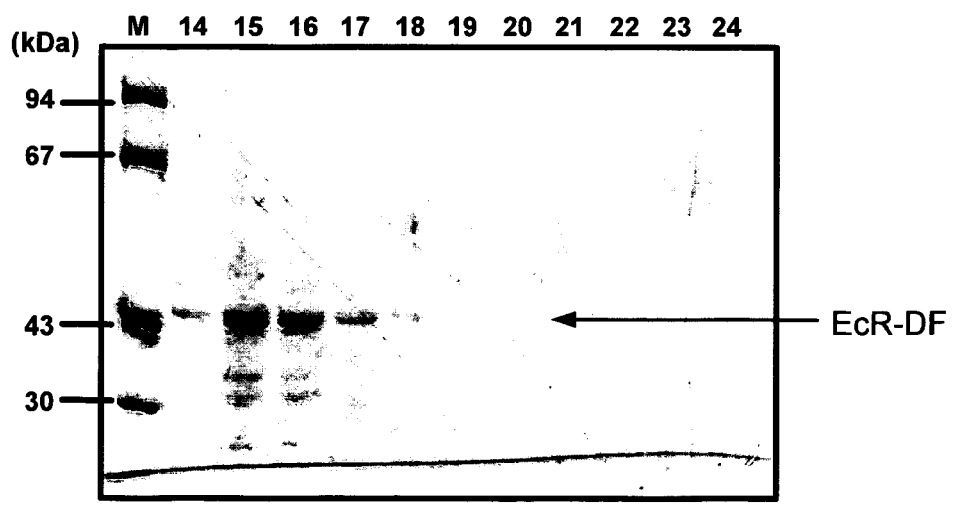

1 : USP-AE-Supernatant
2 : USP-AE-Pass by
3 : USP-AE-Wash
4 : USP-AE-Elute

5 : USP-DE-Pass by
6 : USP-DE-Wash1
7 : USP-DE-Wash2
8 : USP-DE-Elute1
9 : USP-DE-Elute2

10 : USP-E-Pass by
11 : USP-E-Wash1
12 : USP-E-Wash2
13 : USP-E-Elute1

| EcR-Af | 5'-CATTA<u>GGATCC</u>ATGTCCATAGAGTCGCGTTTAG-3' |
| | *Bam*HI |
| EcR-Df | 5'-CATTA<u>GGATCC</u>AGGCCTGAGTGCGTGGTGCCT-3' |
| | *Bam*HI |
| EcR-Fr | 5'-GATTT<u>ACTAGT</u>CTAGAGCGCCGCGCTTTCCG-3' |
| | *Spe*I |
| USP-Af | 5'-ATAAC<u>GGATCC</u>ATGTCAGTGGCGAAGAAAGATAAG-3' |
| | *Bam*HI |
| USP-Df | 5'-ATTAC<u>GGATCC</u>AAGAGGGAGGCAGTTCAAGAG-3' |
| | *Bam*HI |
| USP-Er | 5'-ATTAC<u>ACTAGT</u>TACATGACGTTGGCGTCGATG-3' |
| | *Spe*I |

SEQUENCE LISTING

<160> NUMBER OF SEQ ID NOS: 53

<210> SEQ ID NO 1
<211> LENGTH: 363
<212> TYPE: PRT
<213> ORGANISM: Spodoptera litura

<400> SEQUENCE: 1

| | | | | | | | | | | | | | | |
|---|---|---|---|---|---|---|---|---|---|---|---|---|---|---|
| Met | Gly | Ser | Ser | His | His | His | His | His | Ser | Ser | Gly | Leu | Val | Pro |
| 1 | | | | 5 | | | | | 10 | | | | | 15 |

Arg Gly Ser His Met Ala Ser Arg Pro Glu Cys Val Val Pro Glu Asn
            20                  25                  30

Gln Cys Ala Met Lys Arg Lys Glu Lys Lys Ala Gln Arg Glu Lys Asp
            35                  40                  45

Arg Leu Pro Val Ser Thr Thr Val Asp Asp His Met Pro Pro Ile
 50                      55                  60

Met Gln Cys Asp Pro Pro Pro Glu Ala Ala Arg Ile Leu Glu Cys
 65                  70                  75                  80

Leu Gln Asn Glu Val Leu Pro Arg Tyr Leu Thr Glu Pro Ile Met Glu
                    85                  90                  95

Gln Asn Arg Leu Lys Asn Val Pro Pro Leu Ser Pro Asn Gln Lys Ser
                100                 105                 110

Leu Ile Ala Arg Leu Val Trp Tyr Gln Glu Gly Tyr Glu Gln Pro Ser
                115                 120                 125

Glu Glu Asp Leu Arg Arg Ile Thr Glu Thr Trp Gln Ser Asp Glu Asp
                130                 135                 140

Glu Glu Glu Ser Asp Met Pro Phe Arg Gln Ile Thr Glu Met Thr Ile
145                 150                 155                 160

Leu Thr Val Gln Leu Ile Val Glu Phe Ala Lys Gly Leu Pro Gly Phe
                165                 170                 175

Ala Lys Ile Ser Gln Ser Asp Gln Ile Thr Leu Leu Lys Ala Cys Ser
                180                 185                 190

Ser Glu Val Met Met Leu Arg Val Ala Arg Arg Tyr Asp Ala Ser Thr
                195                 200                 205

Asp Ser Val Leu Phe Ala Asn Asn Gln Ala Tyr Thr Arg Asp Asn Tyr
                210                 215                 220

Arg Lys Ala Gly Met Ala Tyr Val Ile Glu Asp Leu Leu His Phe Cys
225                 230                 235                 240

Arg Cys Met Tyr Ala Met Pro Met Asp Asn Ile Gln Tyr Ala Leu Leu
                245                 250                 255

Thr Ala Ile Val Ile Phe Ser Asp Arg Pro Gly Leu Glu Gln Pro Leu
                260                 265                 270

Leu Val Glu Glu Ile Gln Arg Tyr Tyr Leu Asn Thr Leu Arg Met Tyr
                275                 280                 285

Val Leu Asn Leu His Cys Gly Thr Pro Arg Trp Pro Val Val Tyr Gly
                290                 295                 300

Lys Val Leu Ser Val Leu Ser Glu Leu Arg Thr Leu Gly Met Gln Asn
305                 310                 315                 320

Ser Asn Met Cys Ile Ser Leu Lys Leu Lys Asn Arg Lys Leu Pro Pro
                325                 330                 335

Phe Leu Glu Glu Ile Trp Asp Val Ala Asp Val Ser Thr Thr Ala Thr
                340                 345                 350

Pro Ala Asn Pro Val Thr Glu Ser Ala Ala Leu
                355                 360

<210> SEQ ID NO 2
<211> LENGTH: 490
<212> TYPE: PRT
<213> ORGANISM: Spodoptera litura

<400> SEQUENCE: 2

-continued

```
Met Gly Ser Ser His His His His His His Ser Ser Gly Leu Val Pro
 1               5                   10                  15

Arg Gly Ser His Met Ala Ser Met Ser Val Ala Lys Lys Asp Lys Pro
             20                  25                  30

Thr Met Ser Val Thr Ala Leu Ile Asn Trp Ala Arg Pro Leu Pro Pro
         35                  40                  45

Gly Gln Gln Gln Gln Pro Met Thr Pro Thr Ser Pro Gly Ser Met
 50                  55                  60

Leu Gln Pro Met Ala Thr Pro Ser Asn Ile Pro Thr Val Asp Cys Ser
 65              70                  75                  80

Leu Asp Ile Gln Trp Leu Asn Leu Glu Ser Gly Phe Met Ser Pro Met
                 85                  90                  95

Ser Pro Pro Glu Met Lys Pro Asp Thr Ala Met Leu Asp Gly Leu Arg
            100                 105                 110

Asp Asp Ser Thr Pro Pro Ala Phe Lys Asn Tyr Pro Pro Asn His
            115                 120                 125

Pro Leu Ser Gly Ser Lys His Leu Cys Ser Ile Cys Gly Asp Arg Ala
        130                 135                 140

Ser Gly Lys His Tyr Gly Val Tyr Ser Cys Glu Gly Cys Lys Gly Phe
145                 150                 155                 160

Phe Lys Arg Thr Val Arg Lys Asp Leu Thr Tyr Ala Cys Arg Glu Glu
                165                 170                 175

Arg Asn Cys Ile Ile Asp Lys Arg Gln Arg Asn Arg Cys Gln Tyr Cys
                180                 185                 190

Arg Tyr Gln Lys Cys Leu Ala Cys Gly Met Lys Arg Glu Ala Val Gln
                195                 200                 205

Glu Glu Arg Gln Arg Ala Ala Arg Gly Ala Glu Asp Ala His Pro Ser
            210                 215                 220

Ser Ser Val Gln Val Gln Glu Leu Ser Ile Glu Arg Leu Leu Glu Met
225                 230                 235                 240

Glu Ser Met Val Ala Asp Pro Thr Glu Glu Tyr Gln Phe Leu Arg Val
                245                 250                 255

Gly Pro Asp Ser Asn Val Pro Pro Lys Phe Arg Ala Pro Val Ser Ser
                260                 265                 270

Leu Cys Gln Ile Gly Asn Lys Gln Ile Ala Ala Leu Val Val Trp Ala
            275                 280                 285

Arg Asp Ile Pro His Phe Asn Ser Leu His Leu Glu Asp Gln Met Leu
            290                 295                 300

Leu Ile Lys Ala Ser Trp Asn Glu Leu Leu Leu Phe Ala Ile Ala Trp
305                 310                 315                 320

Arg Ser Met Glu Tyr Leu Thr Glu Glu Arg Glu Val Val Asp Ser Ser
                325                 330                 335

Gly Asn Arg Ser Thr Ser Pro Pro Gln Leu Met Cys Leu Met Pro Gly
            340                 345                 350

Met Thr Leu His Arg Asn Ser Ala Leu Gln Ala Gly Val Gly Gln Ile
            355                 360                 365

Phe Asp Arg Val Leu Ser Glu Leu Ser Leu Lys Met Arg Ala Leu Arg
        370                 375                 380

Phe Asp Gln Ala Glu Tyr Val Ala Leu Lys Ala Ile Ile Leu Leu Asn
385                 390                 395                 400

Pro Asp Val Lys Gly Leu Lys Asn Arg Leu Asp Val Glu Leu Leu Arg
                405                 410                 415
```

```
Glu Lys Met Phe Ser Cys Leu Asp Glu Tyr Val Arg Arg Ser Arg Gly
            420                 425                 430

Gly Glu Glu Gly Arg Phe Ala Ala Leu Leu Leu Arg Leu Pro Ala Leu
        435                 440                 445

Arg Ser Ile Ser Leu Lys Ser Phe Glu His Leu Phe Phe His Leu
    450                 455                 460

Val Ala Asp Thr Ser Ile Ala Ser Tyr Ile Arg Asp Ala Leu Arg Ser
465                 470                 475                 480

His Ala Pro Pro Ile Asp Ala Asn Val Met
                485                 490

<210> SEQ ID NO 3
<211> LENGTH: 311
<212> TYPE: PRT
<213> ORGANISM: Spodoptera litura

<400> SEQUENCE: 3

Met Gly Ser Ser His His His His His Ser Ser Gly Leu Val Pro
  1               5                  10                  15

Arg Gly Ser His Met Ala Ser Lys Arg Glu Ala Val Gln Glu Glu Arg
                20                  25                  30

Gln Arg Ala Ala Arg Gly Ala Glu Asp Ala His Pro Ser Ser Ser Val
            35                  40                  45

Gln Val Gln Glu Leu Ser Ile Glu Arg Leu Leu Glu Met Glu Ser Met
        50                  55                  60

Val Ala Asp Pro Thr Glu Glu Tyr Gln Phe Leu Arg Val Gly Pro Asp
65                  70                  75                  80

Ser Asn Val Pro Pro Lys Phe Arg Ala Pro Val Ser Ser Leu Cys Gln
                85                  90                  95

Ile Gly Asn Lys Gln Ile Ala Ala Leu Val Val Trp Ala Arg Asp Ile
            100                 105                 110

Pro His Phe Asn Ser Leu His Leu Glu Asp Gln Met Leu Leu Ile Lys
        115                 120                 125

Ala Ser Trp Asn Glu Leu Leu Leu Phe Ala Ile Ala Trp Arg Ser Met
    130                 135                 140

Glu Tyr Leu Thr Glu Glu Arg Glu Val Val Asp Ser Ser Gly Asn Arg
145                 150                 155                 160

Ser Thr Ser Pro Pro Gln Leu Met Cys Leu Met Pro Gly Met Thr Leu
                165                 170                 175

His Arg Asn Ser Ala Leu Gln Ala Gly Val Gly Gln Ile Phe Asp Arg
            180                 185                 190

Val Leu Ser Glu Leu Ser Leu Lys Met Arg Ala Leu Arg Phe Asp Gln
        195                 200                 205

Ala Glu Tyr Val Ala Leu Lys Ala Ile Ile Leu Leu Asn Pro Asp Val
    210                 215                 220

Lys Gly Leu Lys Asn Arg Leu Asp Val Glu Leu Leu Arg Glu Lys Met
225                 230                 235                 240

Phe Ser Cys Leu Asp Glu Tyr Val Arg Arg Ser Arg Gly Gly Glu Glu
                245                 250                 255

Gly Arg Phe Ala Ala Leu Leu Leu Arg Leu Pro Ala Leu Arg Ser Ile
            260                 265                 270

Ser Leu Lys Ser Phe Glu His Leu Phe Phe His Leu Val Ala Asp
        275                 280                 285

Thr Ser Ile Ala Ser Tyr Ile Arg Asp Ala Leu Arg Ser His Ala Pro
    290                 295                 300
```

Pro Ile Asp Ala Asn Val Met
305             310

<210> SEQ ID NO 4
<211> LENGTH: 20
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (9)..(9)
<223> OTHER INFORMATION: I
<220> FEATURE:
<221> NAME/KEY: modified_base
<222> LOCATION: (12)..(12)
<223> OTHER INFORMATION: I
<220> FEATURE:
<221> NAME/KEY: misc_feature
<222> LOCATION: (18)..(18)
<223> OTHER INFORMATION: n represents a,g,c or t

<400> SEQUENCE: 4
ctggcggtng gnatgmgncc                                              20

<210> SEQ ID NO 5
<211> LENGTH: 20
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (12)..(12)
<223> OTHER INFORMATION: I
<220> FEATURE:
<221> NAME/KEY: misc_feature
<222> LOCATION: (15)..(15)
<223> OTHER INFORMATION: n represents a,g,c or t

<400> SEQUENCE: 5
gtcgggatgm gnccngartg                                              20

<210> SEQ ID NO 6
<211> LENGTH: 20
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (15)..(15)
<223> OTHER INFORMATION: n represents a,g,c or t

<400> SEQUENCE: 6
cccttcgcga aytcnacdat                                              20

<210> SEQ ID NO 7
<211> LENGTH: 20
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (15)..(15)
<223> OTHER INFORMATION: n represents a,g,c or t

```
<220> FEATURE:
<221> NAME/KEY: misc_feature
<222> LOCATION: (18)..(18)
<223> OTHER INFORMATION: n represents a,g,c or t

<400> SEQUENCE: 7
tcgacgatna rytgnacngt                                              20

<210> SEQ ID NO 8
<211> LENGTH: 20
<212> TYPE: DNA
<213> ORGANISM: Artificial Sequence
<220> FEATURE:
<223> OTHER INFORMATION: synthetic construct

<400> SEQUENCE: 8
tcgcgtrcty ttctcacctg                                              20

<210> SEQ ID NO 9
<211> LENGTH: 20
<212> TYPE: DNA
<213> ORGANISM: Artificial Sequence
<220> FEATURE:
<223> OTHER INFORMATION: synthetic construct

<400> SEQUENCE: 9
cgtrctyttc tcacctgttg                                              20

<210> SEQ ID NO 10
<211> LENGTH: 27
<212> TYPE: DNA
<213> ORGANISM: Artificial Sequence
<220> FEATURE:
<223> OTHER INFORMATION: synthetic construct

<400> SEQUENCE: 10
ttcctcatct tcatccgact ctgtgat                                      27

<210> SEQ ID NO 11
<211> LENGTH: 27
<212> TYPE: DNA
<213> ORGANISM: Artificial Sequence
<220> FEATURE:
<223> OTHER INFORMATION: synthetic construct

<400> SEQUENCE: 11
catcttcatc cgactctgtg attcttc                                      27

<210> SEQ ID NO 12
<211> LENGTH: 20
<212> TYPE: DNA
<213> ORGANISM: Artificial Sequence
<220> FEATURE:
<223> OTHER INFORMATION: synthetic construct

<400> SEQUENCE: 12
cagtagatga tcacatgcct                                              20

<210> SEQ ID NO 13
<211> LENGTH: 20
<212> TYPE: DNA
<213> ORGANISM: Artificial Sequence
<220> FEATURE:
<223> OTHER INFORMATION: synthetic construct

<400> SEQUENCE: 13
```
atgatcacat gcctcccatt                                               20

<210> SEQ ID NO 14
<211> LENGTH: 20
<212> TYPE: DNA
<213> ORGANISM: Artificial Sequence
<220> FEATURE:
<223> OTHER INFORMATION: synthetic construct

<400> SEQUENCE: 14
ttycayccaa tagaaacatc                                               20

<210> SEQ ID NO 15
<211> LENGTH: 22
<212> TYPE: DNA
<213> ORGANISM: Artificial Sequence
<220> FEATURE:
<223> OTHER INFORMATION: synthetic construct

<400> SEQUENCE: 15
gtctatgagc gttctctctc ct                                            22

<210> SEQ ID NO 16
<211> LENGTH: 27
<212> TYPE: DNA
<213> ORGANISM: Artificial Sequence
<220> FEATURE:
<223> OTHER INFORMATION: synthetic construct

<400> SEQUENCE: 16
atcctccggc aaaggctttc acttcac                                       27

<210> SEQ ID NO 17
<211> LENGTH: 25
<212> TYPE: DNA
<213> ORGANISM: Artificial Sequence
<220> FEATURE:
<223> OTHER INFORMATION: synthetic construct

<400> SEQUENCE: 17
gttcctcgag gagatctggg acgtg                                         25

<210> SEQ ID NO 18
<211> LENGTH: 45
<212> TYPE: DNA
<213> ORGANISM: Artificial Sequence
<220> FEATURE:
<223> OTHER INFORMATION: synthetic construct

<400> SEQUENCE: 18
ctaatacgac tcactatagg gcaagcagtg gtaacaacgc agagt                   45

<210> SEQ ID NO 19
<211> LENGTH: 3054
<212> TYPE: DNA
<213> ORGANISM: Spodoptera litura

<400> SEQUENCE: 19
tactccgctg acgacggtcg cgcgcgcgca acgtactcgt ttttactgct ccgaacgacg    60
cgttaacccc gtctccacat caccggacga actcgtggga ctcgcgtgct cttcttacct   120
gttgctcgga ttgtgttgtg actagaaaaa gttgtcgccg ctctaacaag acttccgagt   180
cctattggat tgttgcacga aagtcaagac agtggatagc aattcgtttc tgtttgaacg   240
ttgcgtagac gagtggtgca tgtccataga gtcgcgttta gatagtttag tgcgaggaaa   300

```
aagtgaagtg aaagcctttg ccggaggatg tccctcggcg ctcttggata ccggagcgtg    360
tgactcgctc gcagacatga gacgacgctg gtataacaac ggaggtttcc agacgctgcg    420
aatgctcgag gagagctcgt ctgaagtgac atcgtcttca gcgttaggtc tgcctccagc    480
tatggtaatg tccccggaat cgctggcgtc gccagagtac ggcggcctgg agctgtgggg    540
ctatgaagat ggccttacaa catatagcat ggcacagtcg ctgggctctt gcacaatgga    600
gcaacagcag cagccgcagc agcagcaaca gccccagctg actcagccat tgccatcaat    660
gccgttaccc atgccaccga caacaccgaa atcagaaaat gagtcgatgt catcaggtcg    720
tgaggaactg tcaccggctt caagtgttaa cggctgcagt acagatggcg aggcgaggcg    780
gcagaagaaa ggcccagcac cacggcaaca agaggagcta tgtctcgtct gcggcgacag    840
agcctccggg taccattaca acgcgctcac atgtgaaggg tgtaaaggat tcttcaggcg    900
gagtgtaacc aaaaatgcag tgtacatatg caaatttgga cacgcatgtg agatggatat    960
gtatatgcgg agaaaatgtc aagagtgtcg gttgaagaaa tgtctggcag tgggcatgag   1020
gcctgagtgc gtggtgcctg aaaaccagtg tgcgatgaaa cggaaagaga aaaaggcaca   1080
aagggaaaaa gacaagttgc ccgtcagtac aacgacagta gatgatcaca tgcctcccat   1140
tatgcaatgt gatccaccgc ccccagaggc tgcaagaatt aacgaggtgt tgccacggta   1200
cctgactgaa ccgataatgg agcagaacag gctgaagaat gtgcccccc tctctcccaa    1260 ccaaaagtcc ctcatagcga ggctggtctg gtaccaagaa ggctacgaac aaccatcaga   1320
agaggaccta agaagaatca cagagacctg gcagtcggat gaagatgagg aagaatcgga   1380
tatgccgttc cgtcagatca cagagatgac gatcctcaca gtgcagctca ttgtcgaatt   1440
cgctaagggt ctaccaggct cgcaaagat ctcacaatcg gatcagatca cgttattaaa    1500
ggcctgttcg agtgaggtga tgatgttgcg agtagctcgg cggtatgatg cgtcgacaga   1560
tagcgtgttg ttcgccaaca accaggcgta cactcgcgac aactaccgca aggcaggcat   1620
ggcctacgtc atcgaggacc tactgcactt ctgtaggtgc atgtacgcca tgccgatgga   1680
taacatccaa tacgcactgc tcaccgccat cgtcattttc tcagaccggc ccgggcttga   1740
gcaacccctg ttggtggagg agatccagag atattacctg aacacgctgc ggatgtacgt   1800
tctgaacctg cactgtggga cgccgcgctg gccgtcgtc tacggtaagg tcctcagcgt    1860
cctgtcggag ctgcgcaccc tgggcatgca gaactccaac atgtgcatct cgctcaagtt   1920
gaagaacagg aagttgccgc cgttcctcga ggagatctgg gacgtggcgg acgtgtccac   1980
cacggccacg ccggcaaacc ccgtgacgga aagcgcggcg ctctagcccc gccgccctc    2040 aggagagaac gctcatagac tggctagttt tagtgaagtg cacggacact gacgtcggac   2100
gtgatcaacc tatttataag gactgcgaat tttaccactt aagagggtac acctgtaccc   2160
gatttcgtac gtattcggtg accgacgacg atgatgtgcg agagattagt gaatatatgt   2220
gttgttgaac gtttggagaa tatatattag tgttgatcgt tacgggcccg cgccgccgcc   2280
ggtcggcaac tcgaccgacg cccgccgcgg ctccgacttt atttcgtttt cgactggata   2340
ctgagttggt cactcggata cgactgtatg ataagacttc gttcgataag tacacctcct   2400
aaattacaca tacgtacata cgttacgaga gttattagag acaaagtaat atatgaaaag   2460
atgtttctat tgggtgaaaa gttatgttat gtttatttac caaaatgaac aatacgtctg   2520
gcgtcctggg ctgtcgactg tgttgtgtcg tgtagtccgc cgtggccaca ttcccgtggt   2580
gtcacgacaa cgtggtttat attatagtaa atgtgaggcg tgttatcgtg tcctgtcgat   2640
```

```
ttagttccga ttcatgttct atcgtcctgt gcccgcgtcc ctcgactaaa tgaataatta    2700
taatttattg ctgtgattac atttatgaca tgttgatcta ctgtaggctg atgtaagtac    2760
gacgtataca atacaagctg tgtgtcgttg atagcttcta cacatgcaag cctctattag    2820
tttcagtacg tgtttaattc acatggacac tcggcccgca ataatataat aataatcgat    2880
gtacattcac cattctacga ctaagatcac acgacattag tatctaaacg aatacaccat    2940
actgttgact ccttaaacgt agatactgaa gccagtaaca attgaaatgt cagtgcaatt    3000
tatggctact ttcataatca tacaaaaaaa aaaaaaaaaa aaaaaaaaaa aaaa           3054
```

<210> SEQ ID NO 20
<211> LENGTH: 588
<212> TYPE: PRT
<213> ORGANISM: Spodoptera litura

<400> SEQUENCE: 20

```
Met Ser Ile Glu Ser Arg Leu Asp Ser Leu Val Arg Gly Lys Ser Glu
 1               5                  10                  15

Val Lys Ala Phe Ala Gly Gly Cys Pro Ser Ala Leu Leu Asp Thr Gly
            20                  25                  30

Ala Cys Asp Ser Leu Ala Asp Met Arg Arg Trp Tyr Asn Asn Gly
        35                  40                  45

Gly Phe Gln Thr Leu Arg Met Leu Glu Glu Ser Ser Glu Val Thr
    50                  55                  60

Ser Ser Ser Ala Leu Gly Leu Pro Pro Ala Met Val Met Ser Pro Glu
65                  70                  75                  80

Ser Leu Ala Ser Pro Glu Tyr Gly Gly Leu Glu Leu Trp Gly Tyr Glu
                85                  90                  95

Asp Gly Leu Thr Thr Tyr Ser Met Ala Gln Ser Leu Gly Ser Cys Thr
            100                 105                 110

Met Glu Gln Gln Gln Pro Gln Gln Gln Gln Pro Gln Leu Thr
        115                 120                 125

Gln Pro Leu Pro Ser Met Pro Leu Pro Met Pro Pro Thr Thr Pro Lys
    130                 135                 140

Ser Glu Asn Glu Ser Met Ser Ser Gly Arg Glu Glu Leu Ser Pro Ala
145                 150                 155                 160

Ser Ser Val Asn Gly Cys Ser Thr Asp Gly Glu Ala Arg Arg Gln Lys
                165                 170                 175

Lys Gly Pro Ala Pro Arg Gln Gln Glu Glu Leu Cys Leu Val Cys Gly
            180                 185                 190

Asp Arg Ala Ser Gly Tyr His Tyr Asn Ala Leu Thr Cys Glu Gly Cys
        195                 200                 205

Lys Gly Phe Phe Arg Arg Ser Val Thr Lys Asn Ala Val Tyr Ile Cys
    210                 215                 220

Lys Phe Gly His Ala Cys Glu Met Asp Met Tyr Met Arg Arg Lys Cys
225                 230                 235                 240

Gln Glu Cys Arg Leu Lys Lys Cys Leu Ala Val Gly Met Arg Pro Glu
                245                 250                 255

Cys Val Val Pro Glu Asn Gln Cys Ala Met Lys Arg Lys Glu Lys Lys
            260                 265                 270

Ala Gln Arg Glu Lys Asp Lys Leu Pro Val Ser Thr Thr Thr Val Asp
        275                 280                 285

Asp His Met Pro Pro Ile Met Gln Cys Asp Pro Pro Pro Glu Ala
    290                 295                 300
```

```
Ala Arg Ile Asn Glu Val Leu Pro Arg Tyr Leu Thr Glu Pro Ile Met
305                 310                 315                 320

Glu Gln Asn Arg Leu Lys Asn Val Pro Pro Leu Ser Pro Asn Gln Lys
            325                 330                 335

Ser Leu Ile Ala Arg Leu Val Trp Tyr Gln Glu Gly Tyr Glu Gln Pro
        340                 345                 350

Ser Glu Glu Asp Leu Arg Arg Ile Thr Glu Thr Trp Gln Ser Asp Glu
    355                 360                 365

Asp Glu Glu Glu Ser Asp Met Pro Phe Arg Gln Ile Thr Glu Met Thr
370                 375                 380

Ile Leu Thr Val Gln Leu Ile Val Glu Phe Ala Lys Gly Leu Pro Gly
385                 390                 395                 400

Phe Ala Lys Ile Ser Gln Ser Asp Gln Ile Thr Leu Leu Lys Ala Cys
            405                 410                 415

Ser Ser Glu Val Met Met Leu Arg Val Ala Arg Arg Tyr Asp Ala Ser
        420                 425                 430

Thr Asp Ser Val Leu Phe Ala Asn Asn Gln Ala Tyr Thr Arg Asp Asn
    435                 440                 445

Tyr Arg Lys Ala Gly Met Ala Tyr Val Ile Glu Asp Leu Leu His Phe
450                 455                 460

Cys Arg Cys Met Tyr Ala Met Pro Met Asp Asn Ile Gln Tyr Ala Leu
465                 470                 475                 480

Leu Thr Ala Ile Val Ile Phe Ser Asp Arg Pro Gly Leu Glu Gln Pro
            485                 490                 495

Leu Leu Val Glu Glu Ile Gln Arg Tyr Tyr Leu Asn Thr Leu Arg Met
        500                 505                 510

Tyr Val Leu Asn Leu His Cys Gly Thr Pro Arg Trp Pro Val Val Tyr
    515                 520                 525

Gly Lys Val Leu Ser Val Leu Ser Glu Leu Arg Thr Leu Gly Met Gln
530                 535                 540

Asn Ser Asn Met Cys Ile Ser Leu Lys Leu Lys Asn Arg Lys Leu Pro
545                 550                 555                 560

Pro Phe Leu Glu Glu Ile Trp Asp Val Ala Asp Val Ser Thr Thr Ala
            565                 570                 575

Thr Pro Ala Asn Pro Val Thr Glu Ser Ala Ala Leu
        580                 585

<210> SEQ ID NO 21
<211> LENGTH: 32
<212> TYPE: DNA
<213> ORGANISM: Artificial Sequence
<220> FEATURE:
<223> OTHER INFORMATION: synthetic construct

<400> SEQUENCE: 21
catatggcta gcaggcctga gtgcgtggtg cc                              32

<210> SEQ ID NO 22
<211> LENGTH: 32
<212> TYPE: DNA
<213> ORGANISM: Artificial Sequence
<220> FEATURE:
<223> OTHER INFORMATION: synthetic construct

<400> SEQUENCE: 22
ttgttaagct tagtcccaga tctcctcgag ga                              32
```

```
<210> SEQ ID NO 23
<211> LENGTH: 20
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (14)..(14)
<223> OTHER INFORMATION: n represents a,g,c or t
<220> FEATURE:
<221> NAME/KEY: misc_feature
<222> LOCATION: (17)..(17)
<223> OTHER INFORMATION: n represents a,g,c or t

<400> SEQUENCE: 23
atcagaartg tctngcntgc                                              20

<210> SEQ ID NO 24
<211> LENGTH: 20
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (8)..(8)
<223> OTHER INFORMATION: I
<220> FEATURE:
<221> NAME/KEY: misc_feature
<222> LOCATION: (11)..(11)
<223> OTHER INFORMATION: n represents a,g,c or t
<220> FEATURE:
<221> NAME/KEY: misc_feature
<222> LOCATION: (17)..(17)
<223> OTHER INFORMATION: n represents a,g,c or t

<400> SEQUENCE: 24
artgtctngc ntgcggnatg                                              20

<210> SEQ ID NO 25
<211> LENGTH: 20
<212> TYPE: DNA
<213> ORGANISM: Artificial Sequence
<220> FEATURE:
<223> OTHER INFORMATION: synthetic construct

<400> SEQUENCE: 25
ctcggacagc acgcgrtcra                                              20

<210> SEQ ID NO 26
<211> LENGTH: 20
<212> TYPE: DNA
<213> ORGANISM: Artificial Sequence
<220> FEATURE:
<223> OTHER INFORMATION: synthetic construct

<400> SEQUENCE: 26
gacagcacgc grtcraadat                                              20

<210> SEQ ID NO 27
<211> LENGTH: 20
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (8)..(8)
<223> OTHER INFORMATION: I
<220> FEATURE:
```

```
<221> NAME/KEY: misc_feature
<222> LOCATION: (14)..(14)
<223> OTHER INFORMATION: n represents a,g,c or t
<220> FEATURE:
<221> NAME/KEY: misc_feature
<222> LOCATION: (17)..(17)
<223> OTHER INFORMATION: n represents a,g,c or t

<400> SEQUENCE: 27
cgatcgcntg gmgntcnatg                                              20

<210> SEQ ID NO 28
<211> LENGTH: 20
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (11)..(11)
<223> OTHER INFORMATION: I
<220> FEATURE:
<221> NAME/KEY: misc_feature
<222> LOCATION: (14)..(14)
<223> OTHER INFORMATION: n represents a,g,c or t

<400> SEQUENCE: 28
tcgcntggmg ntcnatggag                                              20

<210> SEQ ID NO 29
<211> LENGTH: 20
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (10)..(10)
<223> OTHER INFORMATION: I

<400> SEQUENCE: 29
ctacakgatn ytggtrtcga                                              20

<210> SEQ ID NO 30
<211> LENGTH: 20
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (7)..(7)
<223> OTHER INFORMATION: I

<400> SEQUENCE: 30
cakgatnytg gtrtcgatsg                                              20

<210> SEQ ID NO 31
<211> LENGTH: 20
<212> TYPE: DNA
<213> ORGANISM: Artificial Sequence
<220> FEATURE:
<223> OTHER INFORMATION: synthetic construct

<400> SEQUENCE: 31
tgagctgctt ggatgtgcat                                              20
```

-continued

```
<210> SEQ ID NO 32
<211> LENGTH: 20
<212> TYPE: DNA
<213> ORGANISM: Artificial Sequence
<220> FEATURE:
<223> OTHER INFORMATION: synthetic construct

<400> SEQUENCE: 32
gctgcttgga tgtgcatcct                                               20

<210> SEQ ID NO 33
<211> LENGTH: 24
<212> TYPE: DNA
<213> ORGANISM: Artificial Sequence
<220> FEATURE:
<223> OTHER INFORMATION: synthetic construct

<400> SEQUENCE: 33
cgctccatct cgctgaagag cttc                                          24

<210> SEQ ID NO 34
<211> LENGTH: 19
<212> TYPE: DNA
<213> ORGANISM: Artificial Sequence
<220> FEATURE:
<223> OTHER INFORMATION: synthetic construct

<400> SEQUENCE: 34
gtccatcgcg tcctacatc                                                19

<210> SEQ ID NO 35
<211> LENGTH: 45
<212> TYPE: DNA
<213> ORGANISM: Artificial Sequence
<220> FEATURE:
<223> OTHER INFORMATION: synthetic construct

<400> SEQUENCE: 35
ctaatacgac tcactatagg gcaagcagtg gtaacaacgc agagt                   45

<210> SEQ ID NO 36
<211> LENGTH: 23
<212> TYPE: DNA
<213> ORGANISM: Artificial Sequence
<220> FEATURE:
<223> OTHER INFORMATION: synthetic construct

<400> SEQUENCE: 36
aagcagtggt aacaacgcag agt                                           23

<210> SEQ ID NO 37
<211> LENGTH: 21
<212> TYPE: DNA
<213> ORGANISM: Artificial Sequence
<220> FEATURE:
<223> OTHER INFORMATION: synthetic construct

<400> SEQUENCE: 37
aactggaaga attcgcggcc g                                             21

<210> SEQ ID NO 38
<211> LENGTH: 21
<212> TYPE: DNA
<213> ORGANISM: Artificial Sequence
<220> FEATURE:
```

<223> OTHER INFORMATION: synthetic construct

<400> SEQUENCE: 38
tggaagaatt cgcggccgca g          21

<210> SEQ ID NO 39
<211> LENGTH: 3280
<212> TYPE: DNA
<213> ORGANISM: Spodoptera litura

<400> SEQUENCE: 39

```
gagtcagagc agcgacgccg cccgcatcgg ccgcgagaac ggcgccgctc gcgacattta      60
cgaaaatcga tgcacgatcc gtaaccggca tttaacatta attaactact tgcagtgggt     120
tgatagtaat gtgaggatgc ttgtgtgtgg ccatgtcagt ggcgaagaaa gataagccga     180
ctatgtcggt aacggcactt atcaactggg cacgacccct gccgccaggc cagcagcagc     240
agcagccgat gacgcctacg tcgcctggaa gcatgcttca gccgatggct acaccgtcta     300
acataccgac tgttgactgt tcgctggata ccaatggct gaacttagag agcggtttta     360
tgtcgccgat gtcaccgccg gagatgaagc cagacacggc gatgctagac ggcttgcgag     420
acgactccac cccgcccct gcattcaaga actacccccc caatcatccc ttaagtggtt      480
ccaagcacct ctgttctata tgtggagaca gagcgtcggg aaaacattat ggagtataca     540
gttgtgaggg ttgcaaaggg ttttcaaga ggacggtaag aaaagatctg acgtacgcgt      600
gtcgtgagga gcgtaactgt ataatagaca agcggcagag gataggtgc cagtactgca      660
ggtatcagaa atgtctggct tgcgggatga agagggaggc agttcaagag gagcgacaaa     720
gggcagccag aggtgcggag gatgcacatc caagcagctc agtgcaggta caggaattgt     780
caatcgagcg gttgttggag atggagtcga tggtggctga tcccactgaa gagtaccagt     840
tcctccgtgt ggggcctgac agtaatgtgc cacctaagtt ccgtgcccct gtctcaagcc     900
tttgtcagat aggtaacaaa cagatagcag cgttggttgt ctgggcacgc gacatcccgc     960
acttcaattc tctccacctg gaagaccaga tgctgctcat caaggcatcc tggaacgaac    1020
tgctactctt tgctatcgcc tggcggtcta tggagtattt gacagaggag cgtgaggttg    1080
tagatagctc tggtaacagg tccacatcgc caccacaact catgtgcctc atgcctggta    1140
tgaccctaca ccgtaactcg gctctccaag caggcgtcgg ccagatattc gaccgcgtcc    1200
tttcggaact gtccctcaaa atgcgcgctc tccgcttcga ccaggccgag tatgtcgcgc    1260
tcaaagccat catactgctc aatcctgatg tgaaaggact gaaaaacaga ctagatgttg    1320
aacttttacg agaaaagatg ttctcgtgcc tggacgagta cgtgcggcgg tcgcgcggcg    1380
gcgaggaggg caggttcgcg gcgctcctgc tgcgcctgcc cgcgctgcgc tccatctcgc    1440
tgaagagctt cgagcacctg ttcttcttcc acctcgtggc cgacacgtcc atcgcgtcct    1500
acatccgcga cgcgctgcgc agccacgccc gcccatcga cgccaacgtc atgtaaccat    1560
acggctccta cgcggcagct acgatatact tctcttatct tctctatcat tataagagcg    1620
accggtcgaa ggttcgaggt gagagcactg gtttcggcca tctaattagg attcttttat    1680
ggaaagttag ctttagcaga cgtcgagtgg gcgtgtcgaa gtggttaaga acgtttcgag    1740
gtcttagatt gataatcttg acacctcagt gtatgtgcgt gtgaccgcta cacgacctct    1800
acgatgtaca agtttatata taacggttc tgaacaaaat tgttgctata attataggaa     1860
attcttaat atttaaactt aagtaaaatc tcataaatcg ttaaaataac caaaaggcct    1920
ttgttttatt tagagagcac tgaaggctgt gtttgacaac attctggcta tgcaaagtac    1980
```

-continued

```
gcggacgcga tgtagtgtat aatgagtcgt tggttatatg atatatcatt tactataagt    2040
acctggatgt cgataactct aattcaaccg gcccttcgtc cacttcgtat tggtaagcag    2100
ctacgcaagc agtagagagt gtaagtacaa tatcgacgcg tcgtgtatcg gtccaagtat    2160
cgagatccac acggtagcgg ttagatagtg taaatggggc cgcctctttt attacgtaga    2220
ttatgattaa cgtaaatatt agtcattcat ttattaggga attttaatcg tcaggtaggt    2280
gtccatagcg aattaatata atgttagact aattaatgtg taattttaac atttaccaaa    2340
tctctcttca aagcacatac atttattact atgtattttta atggattgat aagtgtccta    2400
tgagccagag ataaaatcat gttgattcgt aaaaactaaa agataaatta tacgaaattt    2460
tatgcttcat atatttcccg tgttacatac atgttggtgc tttaacatgc attatttaca    2520
tattgtgcat attaaatatg catagtaagc attaaaatta atgttacttg ataaaacctt    2580
attttcctta cgactagcat agaatgttat gaaactgtaa atatatcttg catgtacaat    2640
gtaattttat tgtttagacg agtaatttat attgcatatt aatatataac tcaccagcgg    2700
tgtaggtggt gggtacaaac ggatagaatg gcctacaaaa tgtaaacaaa acatgtattt    2760
cttggacagg ccactttatt tttgtacacg acggtatctg taacatgcat ttgaaaattc    2820
actaacaaaa ttaaccagta ttatgtattt aacattcacg agacacagat caagtggacg    2880
gcattagagc gatatatgaa cgagtgacga gcatggctaa agaaaatgct aattaagtta    2940
aattgttgaa attaagaaag ctatgtaatg ttgacttgca gctcaatgat gtttaactgg    3000
tatatttggg actatttaag atattcacat actgtagatt gttgaccgtt gacaaccagt    3060
attcctgtta ttatgaagat aaatgttgaa cactgatatt actctatgga ttggtttgaa    3120
ttatatgacg gagatgttgc agtggttgtg agatgattta tactgatgtt cactaattat    3180
ctgactaaat ttaagttata tttttgtata gacatacata gctttaagat tcgtgaatgg    3240
tgattaaaat tattatcaca aaaaaaaaaa aaaaaaaaa                           3280
```

<210> SEQ ID NO 40
<211> LENGTH: 467
<212> TYPE: PRT
<213> ORGANISM: Spodoptera litura

<400> SEQUENCE: 40

```
Met Ser Val Ala Lys Lys Asp Lys Pro Thr Met Ser Val Thr Ala Leu
  1               5                  10                  15

Ile Asn Trp Ala Arg Pro Leu Pro Pro Gly Gln Gln Gln Gln Gln Pro
             20                  25                  30

Met Thr Pro Thr Ser Pro Gly Ser Met Leu Gln Pro Met Ala Thr Pro
         35                  40                  45

Ser Asn Ile Pro Thr Val Asp Cys Ser Leu Asp Ile Gln Trp Leu Asn
     50                  55                  60

Leu Glu Ser Gly Phe Met Ser Pro Met Ser Pro Glu Met Lys Pro
 65                  70                  75                  80

Asp Thr Ala Met Leu Asp Gly Leu Arg Asp Asp Ser Thr Pro Pro
                 85                  90                  95

Ala Phe Lys Asn Tyr Pro Pro Asn His Pro Leu Ser Gly Ser Lys His
            100                 105                 110

Leu Cys Ser Ile Cys Gly Asp Arg Ala Ser Gly Lys His Tyr Gly Val
        115                 120                 125

Tyr Ser Cys Glu Gly Cys Lys Gly Phe Phe Lys Arg Thr Val Arg Lys
    130                 135                 140
```

-continued

Asp Leu Thr Tyr Ala Cys Arg Glu Glu Arg Asn Cys Ile Ile Asp Lys
145                 150                 155                 160

Arg Gln Arg Asn Arg Cys Gln Tyr Cys Arg Tyr Gln Lys Cys Leu Ala
                165                 170                 175

Cys Gly Met Lys Arg Glu Ala Val Gln Glu Arg Gln Arg Ala Ala
            180                 185                 190

Arg Gly Ala Glu Asp Ala His Pro Ser Ser Val Gln Val Gln Glu
        195                 200                 205

Leu Ser Ile Glu Arg Leu Leu Glu Met Glu Ser Met Val Ala Asp Pro
    210                 215                 220

Thr Glu Glu Tyr Gln Phe Leu Arg Val Gly Pro Asp Ser Asn Val Pro
225                 230                 235                 240

Pro Lys Phe Arg Ala Pro Val Ser Ser Leu Cys Gln Ile Gly Asn Lys
                245                 250                 255

Gln Ile Ala Ala Leu Val Val Trp Ala Arg Asp Ile Pro His Phe Asn
            260                 265                 270

Ser Leu His Leu Glu Asp Gln Met Leu Leu Ile Lys Ala Ser Trp Asn
        275                 280                 285

Glu Leu Leu Leu Phe Ala Ile Ala Trp Arg Ser Met Glu Tyr Leu Thr
290                 295                 300

Glu Glu Arg Glu Val Val Asp Ser Ser Gly Asn Arg Ser Thr Ser Pro
305                 310                 315                 320

Pro Gln Leu Met Cys Leu Met Pro Gly Met Thr Leu His Arg Asn Ser
                325                 330                 335

Ala Leu Gln Ala Gly Val Gly Gln Ile Phe Asp Arg Val Leu Ser Glu
            340                 345                 350

Leu Ser Leu Lys Met Arg Ala Leu Arg Phe Asp Gln Ala Glu Tyr Val
        355                 360                 365

Ala Leu Lys Ala Ile Ile Leu Leu Asn Pro Asp Val Lys Gly Leu Lys
370                 375                 380

Asn Arg Leu Asp Val Glu Leu Leu Arg Glu Lys Met Phe Ser Cys Leu
385                 390                 395                 400

Asp Glu Tyr Val Arg Arg Ser Arg Gly Gly Glu Gly Arg Phe Ala
                405                 410                 415

Ala Leu Leu Leu Arg Leu Pro Ala Leu Arg Ser Ile Ser Leu Lys Ser
            420                 425                 430

Phe Glu His Leu Phe Phe Phe His Leu Val Ala Asp Thr Ser Ile Ala
        435                 440                 445

Ser Tyr Ile Arg Asp Ala Leu Arg Ser His Ala Pro Pro Ile Asp Ala
    450                 455                 460

Asn Val Met
465

<210> SEQ ID NO 41
<211> LENGTH: 33
<212> TYPE: DNA
<213> ORGANISM: Artificial Sequence
<220> FEATURE:
<223> OTHER INFORMATION: synthetic construct

<400> SEQUENCE: 41
ttcttgctag catgtccata gagtcgcgtt tag                           33

<210> SEQ ID NO 42
<211> LENGTH: 31

<212> TYPE: DNA
<213> ORGANISM: Artificial Sequence
<220> FEATURE:
<223> OTHER INFORMATION: synthetic construct

<400> SEQUENCE: 42
attacaagct tacatgacgt tggcgtcgat g                                    31

<210> SEQ ID NO 43
<211> LENGTH: 33
<212> TYPE: DNA
<213> ORGANISM: Artificial Sequence
<220> FEATURE:
<223> OTHER INFORMATION: synthetic construct

<400> SEQUENCE: 43
catatggcta gcaagaggga ggcagttcag gag                                  33

<210> SEQ ID NO 44
<211> LENGTH: 33
<212> TYPE: DNA
<213> ORGANISM: Artificial Sequence
<220> FEATURE:
<223> OTHER INFORMATION: synthetic construct

<400> SEQUENCE: 44
ttcttgctag catgtccata gagtcgcgtt tag                                  33

<210> SEQ ID NO 45
<211> LENGTH: 32
<212> TYPE: DNA
<213> ORGANISM: Artificial Sequence
<220> FEATURE:
<223> OTHER INFORMATION: synthetic construct

<400> SEQUENCE: 45
tttttggatc cacaagaagg ctatgaacaa cc                                   32

<210> SEQ ID NO 46
<211> LENGTH: 31
<212> TYPE: DNA
<213> ORGANISM: Artificial Sequence
<220> FEATURE:
<223> OTHER INFORMATION: synthetic construct

<400> SEQUENCE: 46
ttcgcaagct tctagagcgc cgcgctttcc g                                    31

<210> SEQ ID NO 47
<211> LENGTH: 32
<212> TYPE: DNA
<213> ORGANISM: Artificial Sequence
<220> FEATURE:
<223> OTHER INFORMATION: synthetic construct

<400> SEQUENCE: 47
tttttggatc cttcagtgca ggtacaggaa tt                                   32

<210> SEQ ID NO 48
<211> LENGTH: 33
<212> TYPE: DNA
<213> ORGANISM: Artificial Sequence
<220> FEATURE:
<223> OTHER INFORMATION: synthetic construct

<400> SEQUENCE: 48

-continued

<210> SEQ ID NO 49
<211> LENGTH: 32
<212> TYPE: DNA
<213> ORGANISM: Artificial Sequence
<220> FEATURE:
<223> OTHER INFORMATION: synthetic construct

<400> SEQUENCE: 49
cattaggatc caggcctgag tgcgtggtgc ct            32

<210> SEQ ID NO 50
<211> LENGTH: 31
<212> TYPE: DNA
<213> ORGANISM: Artificial Sequence
<220> FEATURE:
<223> OTHER INFORMATION: synthetic construct

<400> SEQUENCE: 50
gatttactag tctagagcgc cgcgctttcc g             31

<210> SEQ ID NO 51
<211> LENGTH: 35
<212> TYPE: DNA
<213> ORGANISM: Artificial Sequence
<220> FEATURE:
<223> OTHER INFORMATION: synthetic construct

<400> SEQUENCE: 51
ataacggatc catgtcagtg gcgaagaaag ataag         35

<210> SEQ ID NO 52
<211> LENGTH: 32
<212> TYPE: DNA
<213> ORGANISM: Artificial Sequence
<220> FEATURE:
<223> OTHER INFORMATION: synthetic construct

<400> SEQUENCE: 52
attacggatc caagagggag gcagttcaag ag            32

<210> SEQ ID NO 53
<211> LENGTH: 32
<212> TYPE: DNA
<213> ORGANISM: Artificial Sequence
<220> FEATURE:
<223> OTHER INFORMATION: synthetic construct

<400> SEQUENCE: 53
attacactag ttacatgacg ttggcgtcga tg            32

MOLTING HORMONE RECEPTOR AND METHOD FOR SCREENING LIGAND TO THE RECEPTOR

TECHNICAL FIELD

The present invention relates to a molting hormone receptor having ability to bind to an insect molting hormone such as ecdysteroid and a method for screening a ligand binding to the above receptor.

BACKGROUND ART

Various objects such as improvement of productivity or improvement of the quality of products can be achieved by pest control in agricultural production sites such as fields. Thus, various studies regarding pest control have been conducted. It has been desired that a disinfestant comprising an insect growth inhibitor as a main component will be developed, for example.

Molting and/or metamorphosis are characteristic phenomena of insects. Such molting and/or metamorphosis of insects are controlled by hormones. It has been known that molting and/or metamorphosis of insects are controlled by a steroid hormone, ecdysteroid. First, ecdysteroid synthesized in the body of an insect binds to a heterodimer consisting of a molting hormone receptor and USP (ultraspiracle) existing in the nucleus through the cell membrane, so as to form a complex. Subsequently, this complex binds to a response sequence existing upstream of an early gene cluster, so as to induce the expression of the early gene cluster. Thereafter, as a result of the expression of the early gene cluster, the expression of a gene cluster associated with the molting and/or metamorphosis of the insect is promoted, and the molting and/or metamorphosis of the insect progresses.

Thus, it has been known that a molting hormone receptor is located at the uppermost stream of a signaling pathway during the molting and/or metamorphosis of an insect. Accordingly, it is said that a search for a substance inhibiting the binding of ecdysteroid to a molting hormone receptor that is used as the aforementioned insect growth inhibitor is effective for the development of a disinfestant.

However, a method for screening such a substance that inhibits the binding of ecdysteroid to a molting hormone receptor has not yet been established. A substance that is effective as a disinfestant could not easily be screened. As a system for screening an insect growth inhibitor, screening systems such as a system using an insect as a whole, a system using a portion of tissues such as epidermis, or a system using cultured cells have conventionally been known (refer to Non-Patent Documents 1 to 4). However, under the present circumstances, almost no studies have been conducted regarding the screening of an insect growth inhibitor at a molecular level (protein level).

Non-Patent Document 1

Kenichi Mikitani Appl. Entomol. Zool. 31 (4): 531-536

A novel ecdysone responsive reportaer plasmid regulated by the 5'-upstreme region of the Drosophila melanogaster (Diptera; Drosophilidae) acethylcholinesterase gene Non-Patent Document 2

Kenichi Mikitani J. Insect Physiol. 42: (10) 937-941 October 1996

Ecdysteroid receptor binding activity and ecdysteroid agonist activity at the level of gene expression are correlated with the activity of dibenzoyl hydrazines in larvae of Bombyx mori Non-Patent Document 3

Kenichi Mikitani BIOCHEM. BIOPHYS. RES. COMMUN. 227: (2) 427-432 Oct. 14, 1996

A new nonsteroidal chemical class of ligand for the ecdysteroid receptor 3,5-di-tert-butyl-4-hydroxy-N-isobutyl-benzamide shows apparent insect molting hormone activities at molecular and cellular levels Non-Patent Document 4

Trisyono A, Goodman C L, Grasela J J, et al. IN VITRO CELLULAR & DEVELOPMENTAL BIOLOGY-ANIMAL 36: (6) 400-404 June 2000

Establishment and characterization of an Ostriniia nubilalis cell line, and its response to ecdysone agonists Thus, taking into consideration the aforementioned actual situation, it is an object of the present invention to provide a completely novel molting hormone receptor and a method for screening a ligand binding thereto, so as to efficiently screen a substance that can be applied to a disinfestant or the like.

DISCLOSURE OF THE INVENTION

As a result of intensive studies directed towards achieving the aforementioned object, the present inventors have discovered a novel binding of a molting hormone to each domain of a molting hormone receptor, thereby completing the present invention.

The present invention includes the following features.

(1) An insect molting hormone receptor comprising the following polypeptide (a) and polypeptide (b) or (c):

(a) a polypeptide, which has the amino acid sequence shown in SEQ ID NO: 1 (EcR-DF), or a polypeptide, which has an amino acid sequence comprising a deletion, substitution, or addition of one or more amino acids with respect to the amino acid sequence shown in SEQ ID NO: 1 (EcR-DF), and which forms a complex with the following polypeptide (b) or (c) and is capable of binding to a molting hormone in a state where it forms the above-described complex;

(b) a polypeptide, which has the amino acid sequence shown in SEQ ID NO: 2 (USP-AE), or a polypeptide, which has an amino acid sequence comprising a deletion, substitution, or addition of one or more amino acids with respect to the amino acid sequence shown in SEQ ID NO: 2 (USP-AE), and which may form a complex with the above-described polypeptide (a); and (c) a polypeptide, which has the amino acid sequence shown in SEQ ID NO: 3 (USP-DE), or a polypeptide, which has an amino acid sequence comprising a deletion, substitution, or addition of one or more amino acids with respect to the amino acid sequence shown in SEQ ID NO: 3 (USP-DE), and which may form a complex with the above-described polypeptide (a).

(2) The insect molting hormone receptor described in (1) above, wherein the above-described polypeptides (a), (b), and (c) are expressed in Escherichia coli.

(3) The insect molting hormone receptor described in (1) above, wherein the above-described polypeptide (a) is allowed to express in Escherichia coil and is then subjected to gel filtration, and thus, the above-described polypeptide (a) has activity of binding to the above-described polypeptide (b) or (c).

(4) A method for screening a ligand binding to a molting hormone receptor, which comprises: a first step of allowing a test substance to act on the insect molting hormone receptor described in any one of (1) to (3) above; and a second step of measuring the binding of the above-described complex to the above-described test substance.

(5) The method for screening a ligand binding to a molting hormone receptor described in (4) above, wherein, in the above-described first step, the above-described insect molting hormone receptor is mixed with the above-described test substance, and the mixture is then reacted for 30 to 90 minutes.

(6) The method for screening a ligand binding to a molting hormone receptor described in (4) above, wherein, in the above-described first step, the above-described insect molting hormone receptor is mixed with the above-described test substance, and the mixture is then reacted at a temperature between 20° C. and 37° C.

(7) The method for screening a ligand binding to a molting hormone receptor described in (4) above, wherein, in the above-described first step, the above-described insect molting hormone receptor is mixed with the above-described test substance, and the mixture is then reacted under conditions where substantially no salts exist.

(8) An agent for screening a ligand binding to an insect molting hormone receptor, which comprises the following polypeptide (a) and polypeptide (b) or (c):

(a) a polypeptide, which has the amino acid sequence shown in SEQ ID NO: 1 (EcR-DF), or a polypeptide, which has an amino acid sequence comprising a deletion, substitution, or addition of one or more amino acids with respect to the amino acid sequence shown in SEQ ID NO: 1 (EcR-DF), and which forms a complex with the following polypeptide (b) or (c) and is capable of binding to a molting hormone in a state where it forms the above-described complex;

(b) a polypeptide, which has the amino acid sequence shown in SEQ ID NO: 2 (USP-AE), or a polypeptide, which has an amino acid sequence comprising a deletion, substitution, or addition of one or more amino acids with respect to the amino acid sequence shown in SEQ ID NO: 2 (USP-AE), and which may form a complex with the above-described polypeptide (a); and (c) a polypeptide, which has the amino acid sequence shown in SEQ ID NO: 3 (USP-DE), or a polypeptide, which has an amino acid sequence comprising a deletion, substitution, or addition of one or more amino acids with respect to the amino acid sequence shown in SEQ ID NO: 3 (USP-DE), and which may form a complex with the above-described polypeptide (a).

(9) The agent for screening a ligand binding to an insect molting hormone receptor described in (7) above, wherein the above-described polypeptides (a), (b), and (c) are expressed in *Escherichia coli*.

(10) The agent for screening a ligand binding to an insect molting hormone receptor described in (8) above, wherein the above-described polypeptide (a) is allowed to express in *Escherichia coli* and is then subjected to gel filtration, and thus, the above-described polypeptide (a) has activity of binding to the above-described polypeptide (b) or (c).

This specification includes part or all of the contents as disclosed in the specification and/or drawings of Japanese Patent Application No. 2003-031606, which is a priority document of the present application.

BRIEF DESCRIPTION OF THE DRAWINGS

FIG. 1(*a*) is a block diagram schematically showing a domain structure of EcR, and FIG. 1(*b*) is a block diagram schematically showing a domain structure of USP;

FIG. 2 is a view showing the positions and sequences (SEQ ID NOS: 4-18), of primers prepared by cDNA cloning of EcR;

FIG. 3 is a view showing the positions and sequences (SEQ ID NOS: 23-38) of primers prepared by cDNA cloning of USP;

FIG. 4 is a view showing EcR recombinants with various lengths prepared in Example 2 (SEQ ID NOS: 44, 21, 45, 22 and 46);

FIG. 7 includes several photographs showing the results of SDS-PAGE performed on USP recombinants expressed in *Escherichia coli*;

FIG. 10 is a photograph showing the results of SDS-PAGE, which are obtained by subjecting all EcR recombinants to a refolding reaction in which gel filtration chromatography has been applied, and confirming that all the EcR recombinant have been eluted at a position of exclusion limit;

BEST MODE FOR CARRYING OUT THE INVENTION

Figure 5:
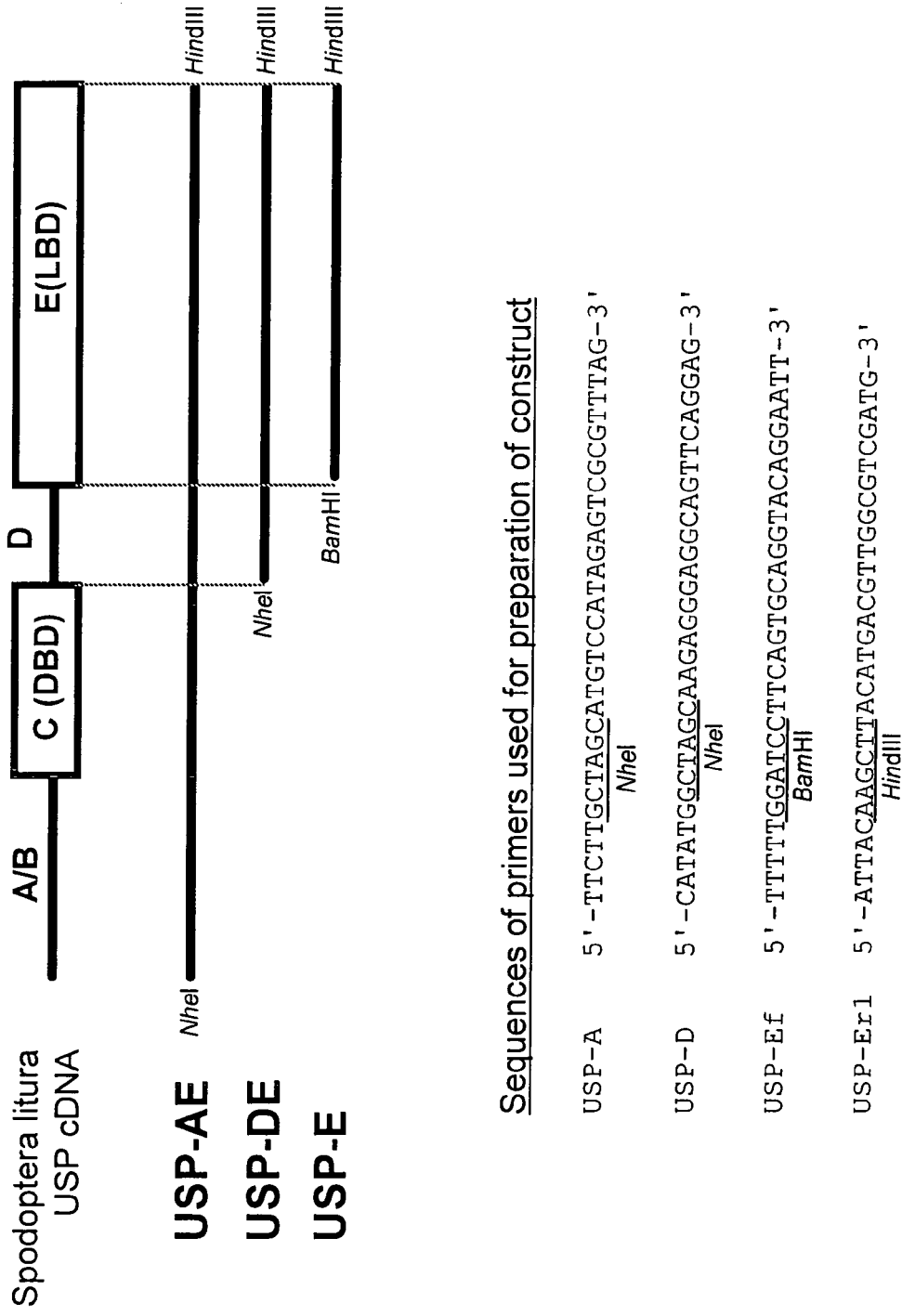
FIG. 5 is a view showing USP recombinants with various lengths prepared in Example 2 (SEQ ID NOS: 41, 43, 47 and 42)

The present invention will be described in detail below.

A screening method to which the present invention is applied (hereinafter referred to simply as "the present screening method" at times) comprises: allowing a test substance to act a complex consisting of a segment from D region to F region (hereinafter abbreviated as EcR-DF at times) of a molting hormone receptor derived from *Spodoptera litura* (hereinafter abbreviated as EcR at times) and a segment from A region to E region (hereinafter abbreviated as USP-AE at times) of Ultraspiracle derived from *Spodoptera litura* (hereinafter abbreviated as USP at times) or a segment from D region to E region thereof (hereinafter abbreviated as USP-DE at times); and then measuring the binding of the complex to the test substance; so as to evaluate the ability of the test substance to bind to the molting hormone receptor (ligand ability).

As shown in FIG. 1a, the term "molting hormone receptor" is used herein to mean a receptor binding to a molting hormone, which comprises 6 regions consisting of A/B region, C region, D region, E region, and F region. Such a molting hormone receptor has been identified in insects other than *Spodoptera litura*. The results of studies regarding such insects other than *Spodoptera litura* suggest that the C region of EcR is a DNA-binding region. In addition, it is suggested that the E region of EcR is a hormone-binding region in insects other than *Spodoptera litura*.

Moreover, as shown in FIG. 1b, USP is an orphan receptor, which comprises 5 regions consisting of A/B region, C region, D region, and E region, and forms a heterodimer together with a molting hormone receptor.

First, EcR-DF used in the present screening method will be described. An example of EcR-DF may be a segment having the amino acid sequence shown in SEQ ID NO: 1. However, EcR-DF is not limited to the segment having the amino acid sequence shown in SEQ ID NO: 1. For example, EcR-DF may be a segment, which has an amino acid sequence comprising a deletion, substitution, and/or addition of one or more amino acids with respect to the amino acid sequence shown in SEQ ID NO: 1, and which forms a complex with USP-AE or USP-DE and is capable of binding to ecdysone in a state where it forms the above complex. The term "more amino acids" is used herein to mean, for example, 2 to 50 amino acids, preferably 2 to 20 amino acids, and more preferably 2 to 10 amino acids.

Moreover, EcR-DF may be a segment comprising the D region and F region of EcR. For example, a portion of the C region may be comprised on the N-terminal side of the D region of EcR. That is to say, an example of an amino acid sequence comprising an addition of 1 or more amino acids with respect to the amino acid sequence shown in SEQ ID NO: 1 may be an amino acid sequence, which comprises the D region and F region of EcR and comprises a portion of the C region on the N-terminal side of the above D region. The term "a portion of the C region" is used herein to mean, for example, 1 to 20 amino acids, preferably 1 to 10 amino acids, and more preferably 1 to 5 amino acids.

Next, a method for preparing EcR-DF will be described. In the present screening method, a method for preparing EcR-DF is not particularly limited. For example, EcR-DF can be prepared as follows. That is, a cDNA library of *Spodoptera litura* is first prepared, and cDNA encoding EcR is cloned using certain primers. Subsequently, using this EcR cDNA, the nucleotide sequence of the coding region of the EcR gene is determined. Primers for amplifying a region encoding EcR-DF are designed based on the nucleotide sequence. Using the primers, PCR is carried out with EcR cDNA as a template, so as to amplify DNA encoding EcR-DF. Thereafter, the amplified DNA is cloned into a suitable vector, and a suitable host is then transformed with the above vector. Thereafter, EcR-DF, which has been allowed to express in the obtained transformant, is recovered, so as to prepare EcR-DF.

In the aforementioned method for preparing EcR, mRNA used for preparing a cDNA library may be extracted from *Spodoptera litura* at any stage such as an imago, a larva, or a chrysalis. In addition, such mRNA may be extracted from any sites of *Spodoptera litura*. Specifically, total RNA can be extracted from the fat body of a *Spodoptera litura* larva, and mRNA contained in the extracted total RNA can be used.

Preparation of a cDNA library from mRNA contained in total RNA can be carried out according to a common method. That is, first strand cDNA is synthesized from total RNA, and then, using this as a template, EcR cDNA can be cloned.

As primers used for cloning of EcR cDNA, degenerate primers designed based on sequences conserved among other lepidopters can be used. Specific examples of such degenerate primers may include 6 sets of degenerate primers as shown in FIG. 2. These 6 sets of degenerate primers were named as EcR-F1 and EcR-R1; EcR-F2 and EcR-R2; EcR-F3 and EcR-R3; EcR-F4 and EcR-R4; EcR-F5 and EcR-R5; and EcR-F6 and EcR-R6.

The nucleotide sequences of these degenerate primers are shown below.

```
EcR-F1:                              (SEQ ID NO: 4)
5'-CTGGCGGTIGGIATGMGNCC-3'

EcR-F2:                              (SEQ ID NO: 5)
5'-GTCGGGATGMGICCNGARTG-3'

EcR-R1:                              (SEQ ID NO: 6)
5-'CCCTTCGCGAAYTCNACDAT-3'

EcR-R2:                              (SEQ ID NO: 7)
5'-TCGACGATIARYTGNACNGT-3'

EcR-F3:                              (SEQ ID NO: 8)
5'-TCGCGTRCTYTTCTCACCTG-3'

EcR-F4:                              (SEQ ID NO: 9)
5'-CGTRCTYTTCTCACCTGTTG-3'
```

```
-continued

EcR-R3:                                  (SEQ ID NO: 10)
5'-TTCCTCATCTTCATCCGACTCTGTGAT-3'

EcR-R4:                                  (SEQ ID NO: 11)
5'-CATCTTCATCCGACTCTGTGATTCTTC-3'

EcR-F5:                                  (SEQ ID NO: 12)
5'-CAGTAGATGATCACATGCCT-3'

EcR-F6:                                  (SEQ ID NO: 13)
5'-ATGATCACATGCCTCCCATT-3'

EcR-R5:                                  (SEQ ID NO: 14)
5'-TTYCAYCCAATAGAAACATC-3'

EcR-R6:                                  (SEQ ID NO: 15)
5'-GTCTATGAGCGTTCTCTCTCCT-3'
```

Using these degenerate primers, RT-PCR is carried out with the first strand cDNA synthesized from the total RNA as a template, so as to synthesize a cDNA fragment. Thereafter, the nucleotide sequence of the synthesized cDNA fragment is determined, and the homology thereof with EcR of other lepidopters is then analyzed. When the above cDNA fragment shows high homology with EcR of other lepidopters, it can be determined that it is EcR cDNA.

Subsequently, based on this nucleotide sequence, a specific primer (EcR-5'R) used in 5' RACE for determining the nucleotide sequence of the full-length cDNA of EcR, and a specific primer (EcR-3'F1) used in 3' RACE therefor, can be designed.

```
EcR-5'R:                                 (SEQ ID NO: 16)
5'-ATCCTCCGGCAAAGGCTTTCACTTCAC-3'

EcR-3'F1:                                (SEQ ID NO: 17)
5'-GTTCCTCGAGGAGATCTGGGACGTG-3'
```

Using these primers EcR-5'R and EcR-3'F1 and a primer (UPM) specific for the anchor sequence of SMART™RACE cDNA Amplification Kit, PCR is carried out with the first strand cDNA synthesized from the total RNA as a template, so as to synthesize a cDNA fragment. The nucleotide sequence of UPM is shown below.

```
UPM:                                     (SEQ ID NO: 18)
5'-CTAATACGACTCACTATAGGGCAAGCAGTGGTAACAACGCAGAGT-3'
```

Thereafter, from the nucleotide sequence of the synthesized cDNA and the nucleotide sequence of the cDNA fragment synthesized using the aforementioned degenerate primers, the nucleotide sequence of the full-length cDNA of EcR can be determined. The nucleotide sequence of the full-length cDNA of EcR is shown in SEQ ID NO: 19, and the putative amino acid sequence of EcR is shown in SEQ ID NO: 20.

In order to construct all expression vector having DNA encoding EcR-DF, first, using a primer EcR-D: 5'-CATATG-GCTAGCAGGCCTGAGTGCGTGGTGCC-3' (SEQ ID NO: 21) and a primer EcR-F: 5'-TTCGCAAGCTTCTA-GAGCGCCGCGCTTTCCG-3' (SEQ ID NO: 46), which have been designed based on the nucleotide sequence of the full-length cDNA of EcR (SEQ ID NO: 19), PCR is carried out with the cloned EcR cDNA as a template, so as to obtain a DNA fragment encoding EcR-DF.

Subsequently, this DNA fragment is inserted into a suitable vector that depends on a host, so as to construct an expression vector. In addition, when EcR-DF is allowed to express in a host, an expression vector may be constructed such that a histidine tag is added to the N-terminus of EcR-DF.

Herein, *Escherichia coli* is preferably used as a host because a relatively large amount of EcR-DF can be obtained therefrom. However, such a host is not limited to *Escherichia coli*, and various types of cells that are conventionally used in a gene expression system, can be used. Examples of such cells may include: mammalian cell lines such as COS-7 cells or CHO cells; and insect cells such as Sf-9.

When *Escherichia coli* is used as a host, a vector pET-28b (+) used for expression in *Escherichia coli* can be used as an expression vector. Using the vector pET-28b(+) used for expression in *Escherichia coli*, a histidine tag can be added to the N-terminus of EcR-DF to be expressed.

EcR-DF expressed in a host can be generated according to a common method. When an *Escherichia coli* EL21(DE3) strain is transformed with an expression vector formed by incorporating DNA encoding EcR-DF into pET-28b(+), and when the expression of EcR-DF is induced by 1PTG, EcR-DF forms an insoluble inclusion body. In such a case, EcR-DF can be obtained in a desired form by solubilizing the inclusion body and then refolding it.

Next, USP-AE and USP-DE used in the present screening method will be described.

An example of USP-AE may be a segment having the amino acid sequence shown in SEQ ID NO: 2. However, USP-AE is not limited to the segment having the amino acid sequence shown in SEQ ID NO: 2. For example, USP-AE may be a segment, which has an amino acid sequence comprising a deletion, substitution, and/or addition of one or more amino acids with respect to the amino acid sequence shown in SEQ ID NO: 2, and which may form a complex with EcR-DF. The term "more amino acids" is used herein to mean, for example, 2 to 200 amino acids, preferably 2 to 100 amino acids, and more preferably 2 to 50 amino acids.

Moreover, USP-DE may be a segment having the amino acid sequence shown in SEQ ID NO: 3. However, USP-DE is not limited to the segment having the amino acid sequence shown in SEQ ID NO: 3. For example, USP-DE may be a segment, which has an amino acid sequence comprising a deletion, substitution, and/or addition of one or more amino acids with respect to the amino acid sequence shown in SEQ ID NO: 3, and which may form a complex with EcR-DF. The term "more amino acids" is used herein to mean, for example, 2 to 20 amino acids, preferably 2 to 10 amino acids, and more preferably 2 to 5 amino acids.

Preparation of these USP-AE and USP-DE can be carried out according to the aforementioned method for preparing EcR-DF. In particular, 4 sets of degenerate primers used for cloning of USP-cDNA, specific primers used for 5' RACE, and specific primers used for 3' RACE are shown in FIG. 3. These 4 sets of degenerate primers were named as USP-F1 and USP-R1; USP-F2 and USP-R2; USP-F3 and USP-R3; and USP-F4 and USP-R4.

The nucleotide sequences of the 4 sets of degenerate primers, those of the specific primers used for 5' RACE (USP-5'R1 and USP-5'R2), those of the specific primers used for 3' RACE (USP-3'F1 and USP-3'F2), and those of primers specific for the anchor sequences of SMART™RACE cDNA Amplification Kit (UPM, NUP, RTG, and RTG-N), are shown below.

```
USP-F1:                                  (SEQ ID NO: 23)
5'-ATCAGAARTGTCTNGCNTGC-3'

USP-F2:                                  (SEQ ID NO: 24)
5'-ARTGTCTIGCNTGCGGNATG-3'
```

-continued

USP-R1:  (SEQ ID NO: 25)
5'-CTCGGACAGCACGCGRTCRA-3'

USP-R2:  (SEQ ID NO: 26)
5'-GACAGCACGCGRTCRAADAT-3'

USP-F3:  (SEQ ID NO: 27)
5'-CGATCGCITGGMGNTCNATG-3'

USP-F4:  (SEQ ID NO: 28)
5'-TCGCITGGMGITCNATGGAG-3'

USP-R3:  (SEQ ID NO: 29)
5'-CTACAKGATIYTGGTRTCGA-3'

USP-R4:  (SEQ ID NO: 30)
5'-CAKGATIYTGGTRTCGATSG-3'

USP-5'R1:  (SEQ ID NO: 31)
5'-TGAGCTGCTTGGATGTGCAT-3'

USP-5'R2:  (SEQ ID NO: 32)
5'-GCTGCTTGGATGTGCATCCT-3'

USP-3'F1:  (SEQ ID NO: 33)
5'-CGCTCCATCTCGCTGAAGAGCTTC-3'

USP-3'F2:  (SEQ ID NO: 34)
5'-GTCCATCGCGTCCTACATC-3'

UPM:  (SEQ ID NO: 35)
5'-CTAATACGACTCACTATAGGGCAAGCAGTGGTAACAACGCAGAGT-3'

NUP:  (SEQ ID NO: 36)
5'-AAGCAGTGGTAACAACGCAGAGT-3'

RTG:  (SEQ ID NO: 37)
5'-AACTGGAAGAATTCGCGGCCG-3'

RTG-N:  (SEQ ID NO: 38)
5'-TGGAAGAATTCGCGGCCGCAG-3'

The nucleotide sequence of the cDNA of USP that is cloned according to the aforementioned method for preparing EcR-DF is shown in SEQ ID NO: 39, and the putative amino acid sequence of USP is shown in SEQ ID NO: 40.

DNA encoding EcR-DF is amplified by PCR using EcR cDNA as a template. Thereafter, the amplified DNA is cloned into a suitable vector, and a suitable host is then transformed with the above vector. Thereafter, EcR-DF, which has been allowed to express in the obtained transformant, is recovered, so as to prepare EcR-DF.

In order to construct an expression vector having DNA encoding USP-AE, a primer USP-A: 5'-TTCTTGCTAG-CATGTCCATAGAGTCGCGTTTAG-3' (SEQ ID NO: 41), and a primer USP-Er1: 5'-ATTACAAGCTTACATGACGT-TGGCGTCGATG-3' (SEQ ID NO: 42) are used. In order to construct an expression vector having DNA encoding USP-DE, a primer USP-D: 5'-CATATGGCTAGCAAGAGGGAG-GCAGTTCAGGAG-3' (SEQ ID NO: 43), and the primer USP-Er1 (SEQ ID NO: 42) are used. Using these primers, USP-AE and USP-DE can be obtained as in the case of EcR-DF, as described above.

In the present screening method, using EcR-DF, USP-AE, and USP-DE as obtained above, the ability of a test substance to bind to a molting hormone receptor (ligand ability) is evaluated. For example, the ability of a test substance to bind to a complex consisting of EcR-DF and USP-AE or USP-DE can be evaluated by labeling the test substance. In this evaluation, EcR-DF and USP-AE or USP-DE may be mixed with a test substance, and the ability of the test substance to bind to a complex consisting of EcR-DF and USP-AE or USP-DE may be then evaluated. Otherwise, a complex consisting of EcR-DF and USP-AE or USP-DE has previously been prepared, and thereafter, a test substance may be allowed to act on the complex, and the ability thereof may be evaluated.

In order to label a test substance, a method using radioisotope may be used.

As stated above, the present screening method provides an effective means for searching for a substance that suppresses induction of the expression of a gene cluster associated with molting and/or metamorphosis due to a heterodimer of EcR and USP, using a complex consisting of EcR-DF and USP-AE or USP-DE.

The present invention will be described more in detail below in the following examples. However, the examples are not intended to limit the technical scope of the present invention.

EXAMPLE 1

Determination of Nucleotide Sequences of EcR and USP Derived from *Spodoptera litura*

Material

In the present example, a *Spodoptera litura* larva (the last instar (the sixth-instar) larva (with a body length of approximately 4 cm and a body weight of approximately 1.5 g)) provided from Kumiai Chemical Industry Co., Ltd. was used. The *Spodoptera litura* larva was excised under a stereoscopic microscope, and a fat body thereof was extirpated using a forceps. It was then placed in an Eppendorf tube and then freeze-dried with liquid nitrogen. The thus freeze-dried product was then conserved at −80° C. until it was used for extraction of total RNA.

RT-PCR

In order to extract total RNA from the extirpated fat body of *Spodoptera litura*, an RNA extraction reagent ISOGEN (Nippon Gene Co., Ltd.) was used in accordance with protocols provided with the reagent. All aliquot of the extracted total RNA solution was diluted with DEPC-treated water, and the concentration of the diluted solution was quantified with a spectrophotometer.

2 μg of total RNA was prepared from the obtained total RNA solution. Thereafter, first strand cDNA was synthesized from the total RNA using Ready-To-Go™ T-Primed First-Strand Kit (Amersham Biosciences) in accordance with protocols provided with the kit. At the same time, first strand cDNA was synthesized from 1 μg of total RNA using SMART™RACE cDNA Amplification Kit (CLONTECH), separately.

Using the synthesized first strand cDNA as a template, a PCR reaction was carried out employing a thermal cycler. Primers shown in FIGS. 2 and 3 were used as degenerate primers. The composition of a PCR reaction solution is shown in Table 1.

TABLE 1

| PCR reaction solution | |
|---|---|
| 10 × PCR Buffer (TAKARA) | 2 μl |
| dNTP Mixture (2.5 mM) | 2 μl |
| Primer (forward, 10 μM) | 2 μl |
| Primer (reverse, 10 μM) | 1 μl |
| Template DNA | 0.5 μl |
| TAKARA Taq ™ (5 U/μl) | 0.1 μl |
| Sterilized water | 13.5 μl |
| Total | 20.1 μl |

The reaction was carried out by maintaining at 94° C. for 3 minutes, performing a cycle consisting of denaturation at 94°

C. for 30 seconds, annealing at 55° C. for 30 seconds, and elongation at 72° C. for 30 seconds, 35 times, and then treating at 72° C. for 7 minutes.

A PCR product was subcloned using TA Cloning Kit (Invitrogen). That is, a PCR product was ligated to a vector (pCR 2.1) included in the kit, and competent cells INVαF' (Invitrogen) were then transformed with the obtained plasmid DNA. Thereafter, plasmid DNA into which the PCR product had been inserted was selected, and the nucleotide sequence of the PCR product was determined. Thermo Sequence Cy5.5 dye terminator cycle sequencing kit (Amersham Biosciences) was used for a cycle sequence reaction in which plasmid DNA was used as a template.

5' RACE and 3' RACE

A primer used for 5' RACE and a primer used for 3' RACE were prepared based oil the nucleotide sequence of a cDNA fragment that had been amplified by the aforementioned RT-PCR. In addition, cDNA used as a template in 5' RACE was synthesized using SMART™RACE cDNA Amplification Kit. On the other hand, cDNA used as a template in 3' RACE was synthesized using Ready-To-Go™ T-Primed First-Strand Kit.

Using these primers, the nucleotide sequence of the full-length cDNA of EcR and the nucleotide sequence of the full-length cDNA of USP were determined, The nucleotide sequence of the full-length cDNA of EcR is shown in SEQ ID NO: 19, and the putative amino acid sequence of EcR is shown in SEQ ID NO: 20. The nucleotide sequence of the full-length cDNA of USP is shown in SEQ ID NO: 39, and the putative amino acid sequence of USP is shown in SEQ ID NO: 40.

EXAMPLE 2

Expression of EcR Recombinant and USP Recombinant (*Escherichia coli*)

Preparation of DNA Fragment

First, in order to produce various recombinants with different lengths containing the ligand-binding region (E region) of EcR, the following primers, to which the sequence of a specific restriction site was added, were designed based on the nucleotide sequence obtained in Example 1:

```
EcR-A:                                    (SEQ ID NO: 44)
5'-TTCTTGCTAGCATGTCCATAGAGTCGCGTTTAG-3'

EcR-D:                                    (SEQ ID NO: 21)

EcR-Ef:                                   (SEQ ID NO: 45)
5'-TTTTTGGATCCACAAGAAGGCTATGAACAACC-3'

EcR-Er1:                                  (SEQ ID NO: 22)
5'-TTGTTAAGCTTAGTCCCAGATCTCCTCGAGGA-3'

EcR-F:                                    (SEQ ID NO: 46)
5'-TTCGCAAGCTTCTAGAGCGCCGCGCTTTCCG-3'
```

Moreover, in order to produce various recombinants with different lengths containing the ligand-binding region (E region) of USP, the following primers, to which the sequence of a specific restriction site was added, were designed based on the nucleotide sequence obtained in Example 1:

```
USP-A:                                    (SEQ ID NO: 41)
5'-TTCTTGCTAGCATGTCCATAGAGTCGCGTTTAG-3'

USP-D:                                    (SEQ ID NO: 43)
5'-CATATGGCTAGCAAGAGGGAGGCAGTTCAGGAG-3'
```

```
                       -continued
USP-Ef:                                   (SEQ ID NO: 47)
5'-TTTTTGGATCCTTCAGTGCAGGTACAGGAATT-3'

USP-Er1:                                  (SEQ ID NO: 42)
5'-ATTACAAGCTTACATGACGTTGGCGTCGATG-3'
```

Using these primers, a PCR reaction was carried out with the plasmid used for cloning in Example 1 as template DNA. The obtained PCR product was subcloned. The composition of a PCR reaction solution is shown in Table 2.

TABLE 2

| PCR reaction solution | |
|---|---|
| 10 × EX PCR Buffer (TAKARA) | 3 μl |
| dNTP Mixture (2.5 mM) | 3 μl |
| Primer (forward, 10 μM) | 1.5 μl |
| Primer (reverse, 10 μM) | 1.5 μl |
| Template DNA | 0.15 μl |
| TAKARA EX Taq ™ Hot Start Version (5 U/μl) | 0.15 μl |
| Sterilized water | 20.7 μl |
| Total | 30 μl |

The reaction was carried out by maintaining at 94° C. for 3 minutes, performing a cycle consisting of denaturation at 94° C. for 30 seconds, annealing at 60° C. for 30 seconds, and elongation at 72° C. for 1 minute, 15 times, and then treating at 72° C. for 7 minutes.

The PCR product was recovered from agarose gel, and was then subcloned using TOPO TA Cloning™ Kit (Invitrogen) in accordance with protocols provided with the kit. A DNA sequencer was used to confirm that the nucleotide sequence of a PCR product of interest was correct. Thereafter, a plasmid was digested with specific restriction enzymes (a combination of BamHI-HindIII or NheI-HindIII). The resultant was subjected to 1% agarose gel electrophoresis again, and a DNA fragment of interest was then recovered from the gel.

In the present example, as shown in FIG. 4, full-length EcR (EcR-AF) was obtained using primers EcR-A and EcR-F; a DNA fragment encoding a segment (EcR-DF) from D region to F region of EcR was obtained using primers EcR-D and EcR-F; a DNA fragment encoding a segment (EcR-DE) from D region to E region of EcR was obtained using primers EcR-D and EcR-Er1; a DNA fragment encoding a segment (EcR-EF) from E region to F region of EcR was obtained using primers EcR-Ef and EcR-F; and a DNA fragment encoding a segment (EcR-E) corresponding to the E-region of EcR was obtained using primers EcR-Ef and EcR-Er1. Moreover, in the present example, as shown in FIG. 5, a DNA fragment encoding a segment (USP-AE) from A region to E region of USP was obtained using primers USP-A and USP-Er1; a DNA fragment encoding a segment (USP-DE) from D region to E region of USP was obtained using primers USP-D and USP-Er1; and a DNA fragment encoding a segment (USP-E) corresponding to the E region of USP was obtained using primers USP-Ef and USP-Er1.

Transformation

In order to allow an EcR recombinant and a USP recombinant encoded by the obtained DNA fragments to express in *Escherichia coli*, an expression vector used for transformation was first constructed. As a plasmid vector, pET-28b(+) (Novagen) was used. This vector was constructed such that a histidine (His) tag was added to the N-terminus of a protein of interest. This plasmid DNA was prepared from 25 ml of a culture solution, using High Purity Plasmid Midiprep System (MARLINGEN BIOSCIENCE). Whether or not insert DNA of interest had been precisely inserted into a vector with no displacements in the triplet codon and the frame was confirmed, and it was then used as an expression vector for the following experiments.

Subsequently, using the thus constructed expression vector and the competent cells of an *Escherichia coli* DH5α strain, the cells were transformed with the vector according to the heat shock method and electroporation.

Expression of Protein of Interest

A single colony of the *Escherichia coli* BL21(DE3) strain containing the above expression vector was inoculated into 5 ml of an LB medium, and it was then subjected to shake culture at 37° C. overnight (preculture). Thereafter, a 500-ml Erlenmeyer flask or Sakaguchi flask equipped with a baffle was used as an incubator, and 100 ml of an LB medium and 100 µl of kanamycin were added thereto. Thereafter, 5 ml of the preculture solution was further added thereto. The obtained mixture was subjected to shake culture at 37° C. (culture). When $OD_{600}$ became 0.6 to 0.8, IPTG was added thereto, so as to initiate the induction of a protein of interest. Conditions for induction of each construct are shown in Table 3. It is to be noted that the same conditions were applied to EcR-AF, EcR-DF, EcR-DE, EcR-EF, and EcR-E.

TABLE 3

| | IPTG final concentration | Induction temperature | Time |
|---|---|---|---|
| EcR | 1 mM | 37° C. | 3 h |
| USP-AE | 0.1 mM | 20° C. | 16 h |
| USP-DE | 0.2 mM | 26.5° C. | 6 h |
| USP-E | 0.5 mM | 26.5° C. | 4 h |

After the induction, the culture solution was centrifuged at 4° C. at 8,000 rpm for 5 minutes, so as to collect cells. In the case of an EcR recombinant, cells were well suspended in 15 ml of PBS. In the case of a USP recombinant, cells were well suspended in 10 ml of a lysis buffer (50 nM $NaH_2PO_4$/300 mM NaCl/10 mM imidazole (pH8.0)). Thereafter, 10 mg of lysozyme (SIGMA) was added to each suspension, and the obtained mixture was slowly suspended with a rotator in a low-temperature chamber for 1 hour. It was then freeze-dried at −80° C. After 1 hour or more had passed, the freeze-dried product was unfrozen. Thereafter, using an ultrasonic disintegrator, cells (the USP recombinant) were disintegrated at 120 W for 5 minutes, and cells (the EcR recombinant) were disintegrated at 120 W for 10 minutes. Thereafter, the resultant was centrifuged at 4° C. at 10,000 rpm for 15 minutes.

In the case of the EcR recombinant, a precipitate fraction obtained after centrifugation was suspended in 4 ml of PBS. Thereafter, 1 ml of 25% Triton X-100 was added thereto, and the obtained mixture was then slowly suspended with a rotator at room temperature for 4 hours to overnight. Subsequently, the suspension was centrifuged at 4° C. at 9,000 rpm for 10 minutes. The obtained precipitate was centrifuged in 4 ml of PBS at 4° C. at 9,000 rpm for 5 minutes and then washed. This operation was repeated 5 to 10 times to eliminate Triton X-100 (until the precipitate lost stickiness). Finally, the supernatant was completely eliminated, and the remaining precipitate was then conserved at −20° C. until it was used for purification. On the other hand, in the case of the USP recombinant, cells were disintegrated, and the supernatant fraction obtained after centrifugation was used for the subsequent purification.

Figure 6:
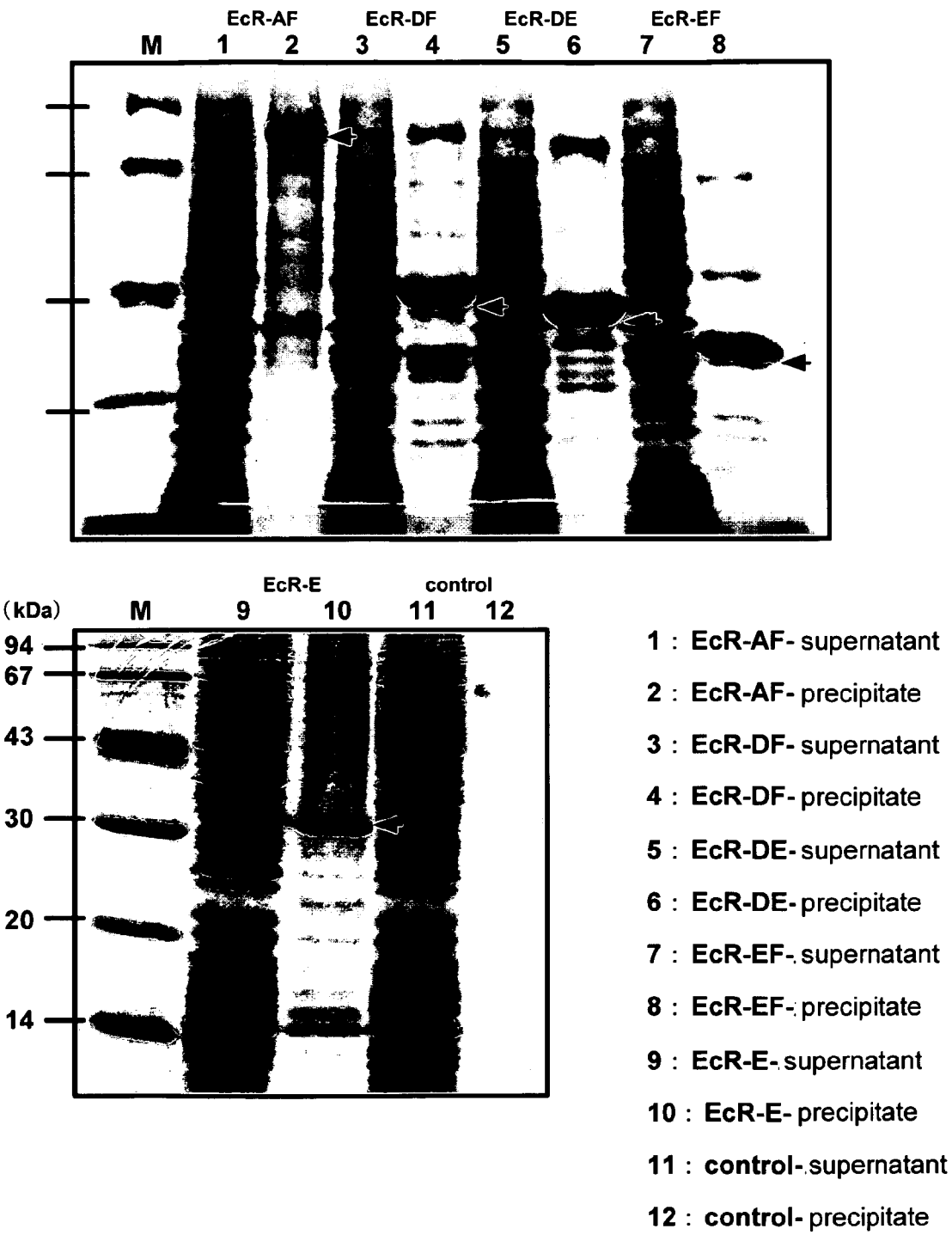
FIG. 6 includes several photographs showing the results of SDS-PAGE performed on EcR recombinants expressed in *Escherichia coli*.

Subsequently, as a result of confirmation by SDS-PAGE, it was found that the expressed EcR recombinants (EcR-AF, -DF, -DE, -EF, and -E) existed in an insoluble inclusion body fraction (FIG. 6). On the other hand, in the case of all the expressed USP recombinants (USP-AE, -DE, and -E), a portion thereof was recovered as a soluble fraction (FIG. 7).

SDS-PAGE was carried out as follows. A sample was mixed with an appropriate amount of sample buffer (0.2M Tris-HCl (pH6.8)/8% SDS/24% β-ME/40% glycerol/0.05% BPB), and the obtained mixture was treated at 100° C. for 5 minutes. As a molecular weight marker, LMW Calibration Kit for SDS Electrophoresis (Amersham Biosciences) was used. After completion of the electrophoresis, the gel was fixed with a decolorizing solution (50% methanol/7% acetic acid) for 15 minutes, and it was then shaken in a CBB staining solution (0.25% CBB R-250/50% methanol/5% acetic acid) for 15 minutes. Finally, decolorization was carried out with a decolorizing solution until the color of background disappeared.

Figure 8:
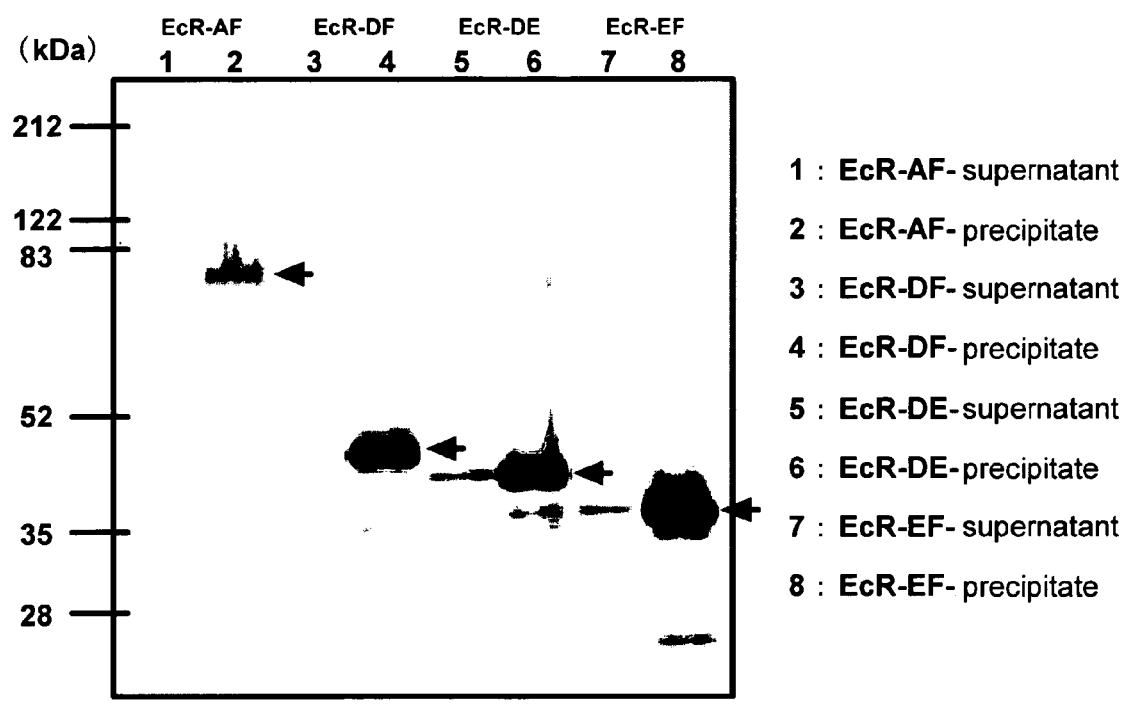
FIG. 8 is a photograph showing the results of Western blotting performed to confirm EcR recombinants.
Figure 9A:
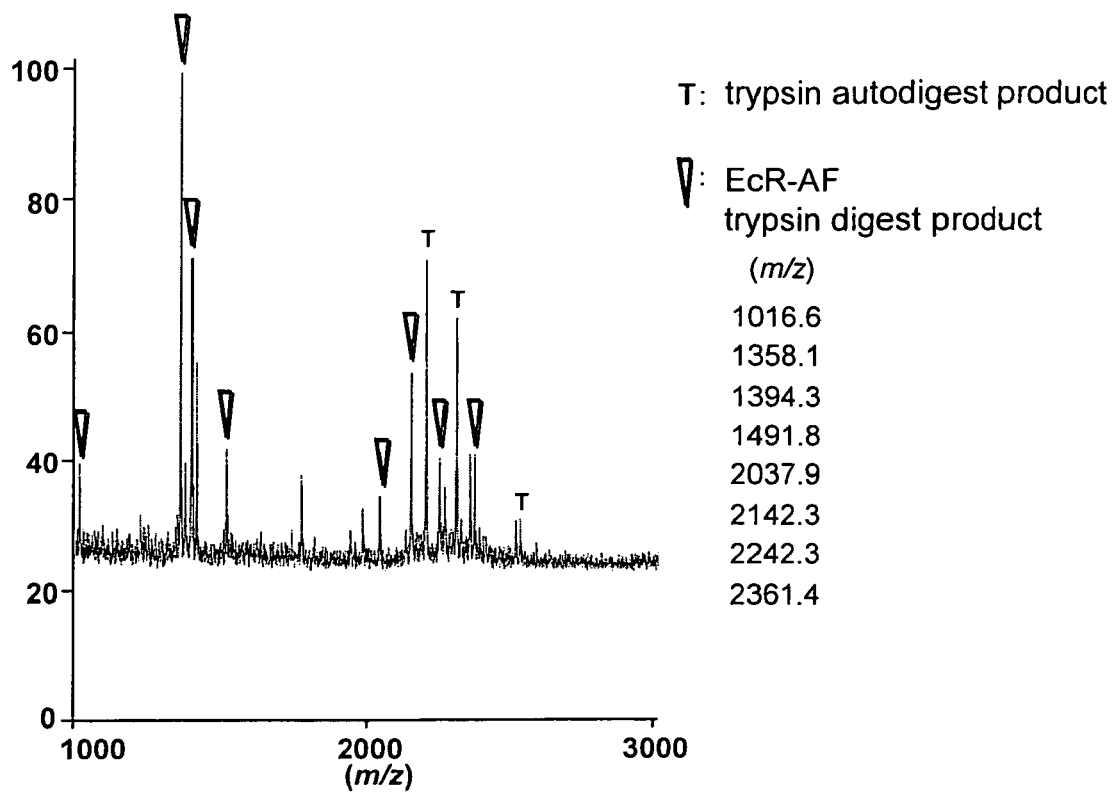
FIG. 9A is a characteristic diagram showing the results obtained by measuring the molecular mass of an EcR recombinant using MALDI-TOF-MS.
Figure 9B:
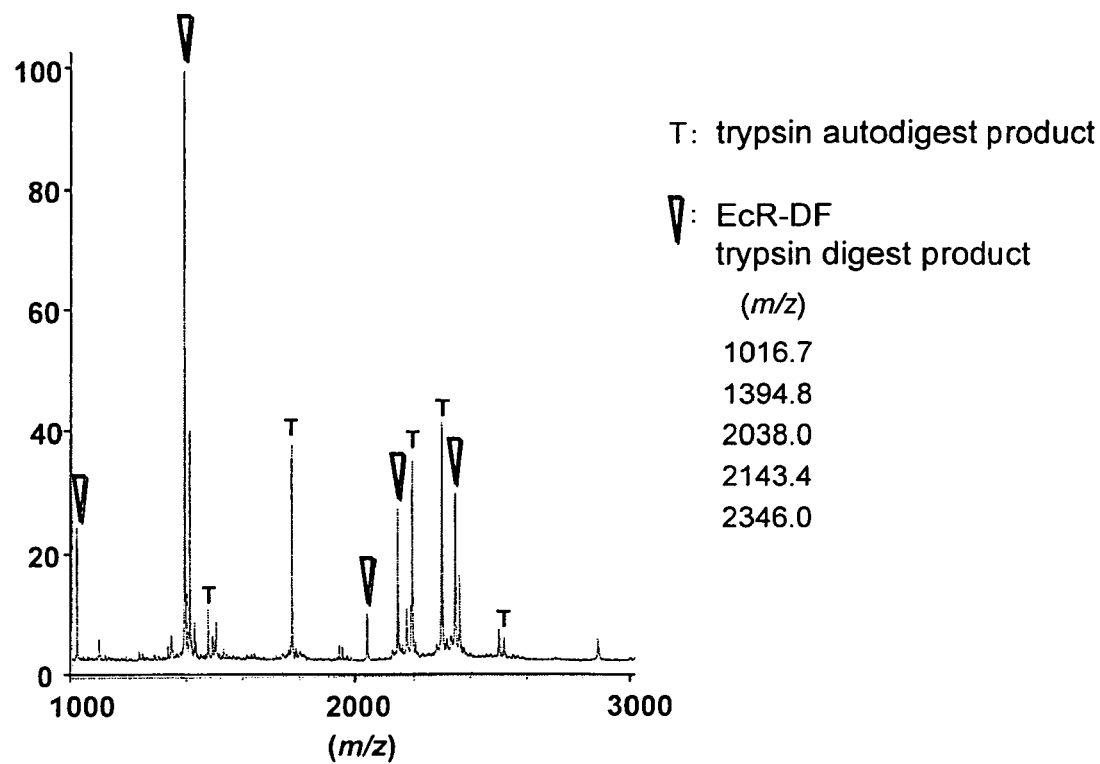
FIG. 9B is a characteristic diagram showing the results obtained by measuring the molecular mass of another EcR recombinant using MALDI-TOF-MS.
Figure 9C:
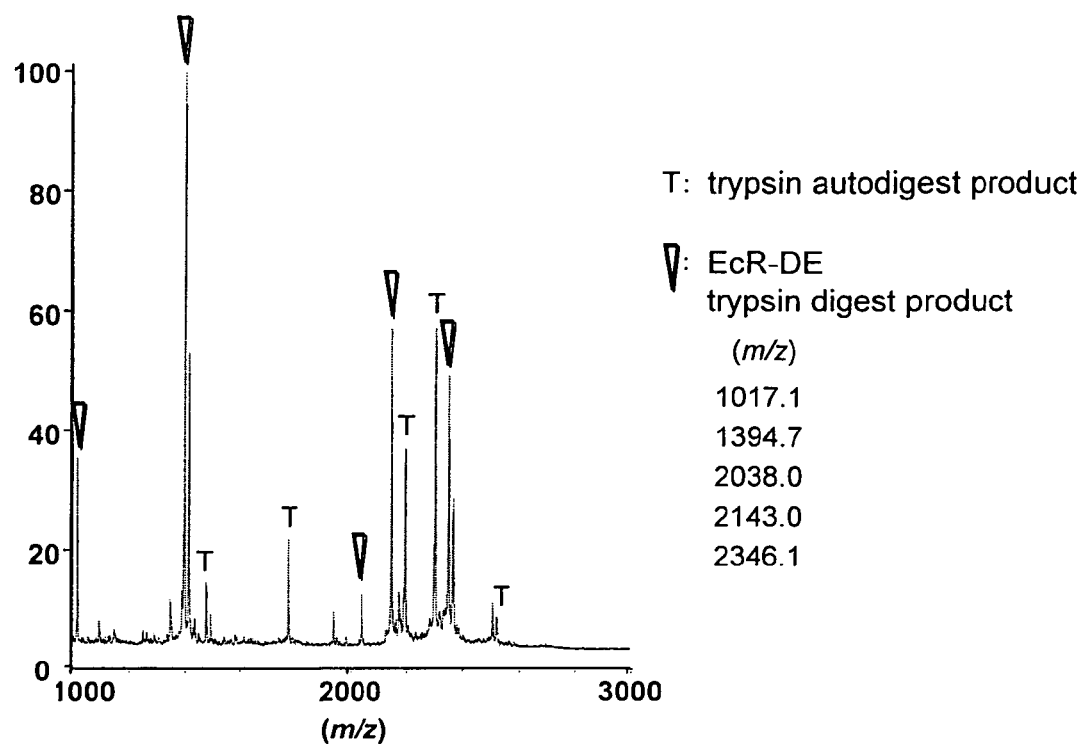
FIG. 9C is a characteristic diagram showing the results obtained by measuring the molecular mass of another EcR recombinant using MALDI-TOF-MS.
Figure 9D:
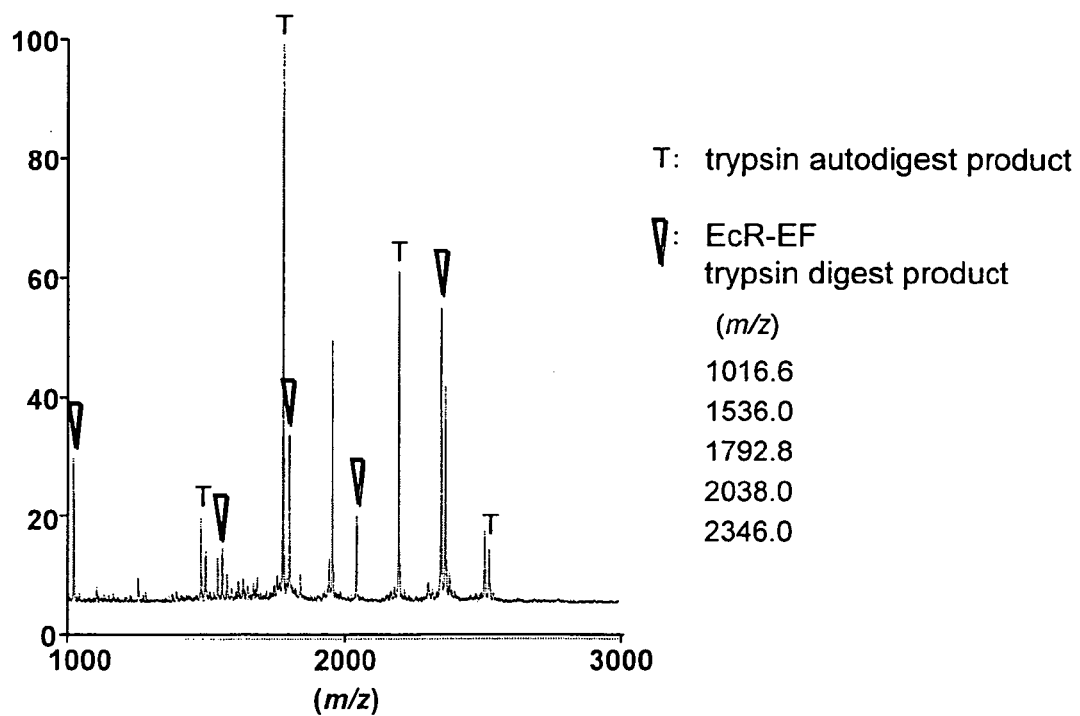
FIG. 9D is a characteristic diagram showing the results obtained by measuring the molecular mass of another EcR recombinant using MALDI-TOF-MS.
Figure 9E:
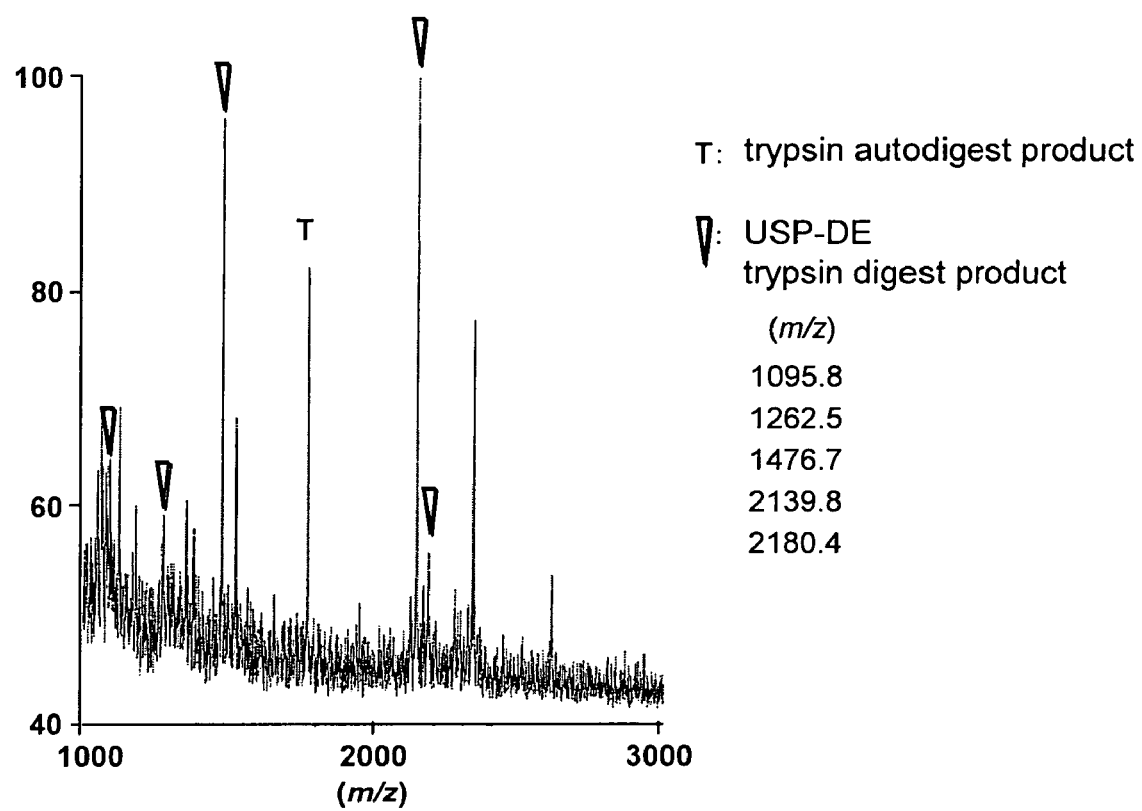
FIG. 9E is a characteristic diagram showing the results obtained by measuring the molecular mass of an EcR recombinant using MALDI-TOF-MS.

In order to confirm that the expressed recombinant was the one of interest, Western blotting was carried out using an anti-His-tag antibody. Precision Prestained Standard (BIO-RAD) was used as a molecular weight marker. After completion of the electrophoresis, using a blocking device, the gel was blocked on a PVDF membrane (ATTO) at 100 mA for 30 minutes. After completion of the blocking, in order to prevent non-specific adsorption of the antibody, blocking was carried out in TBST (137 mM NaCl/2.68 mM KCl/25 mM Tris/0.05% Tween-20) containing 5% skimmed milk for 2 hours to overnight. After completion of the blocking, the membrane was washed with TBST for 10 minutes 4 times. Subsequently, the membrane was incubated at room temperature in an anti-His-antibody (Amersham Biosciences) that had been 2,000 times diluted with TBST. 1.5 hours later, the membrane was washed with TBST for 10 minutes 4 times. Thereafter, an anti-mouse IgG conjugated HRP that had been 5,000 times diluted with TBST was added thereto, and the obtained mixture was incubated at room temperature. 1 hour later, the membrane was washed with TBST for 10 minutes 4 times. SuperSignal West Dura Extended Duration Substrate (Pierce) was then added thereto as a substrate of HRP, so that the resultant was allowed to emit chemoluminescence. The emitted chemoluminescence was then analyzed with an imaging analyzer. As a result, as shown in FIG. 8, it was found that all the expression products were those of interest. Thereafter, the sample subjected to SDS-PAGE was cut out of the gel, and the molecular mass of a digest obtained by digestion with trypsin was measured using MALDI-TOF-MS. As Shown in FIGS. 9A, 9B, 9C, 9D, and 9E, digests of the products of interest were confirmed. Thus, it was found that all the obtained expression products were products of interests.

Purification of Protein Of Interest (EcR Recombinant)

As stated above, all the EcR recombinants form insoluble inclusion bodies, and expression products exist in such inclusion bodies. Since such an EcR recombinant cannot directly be used for the subsequent experiment regarding binding to a ligand, which will be described later, it should be solubilized and refolded, so that it can bind to a ligand. In such a refolding reaction, it is necessary to solubilize an inclusion body in a high-concentration urea or a guanidine hydrochloride aqueous solution and then gradually eliminate such urea or guanidine hydrochloride. Thus, dialysis or dilution has often been applied. In the present example, an EcR recombinant was first solubilized in 8 M urea, and it was then subjected to a refolding reaction in which dilution was applied. When the final concentration of urea became 1 M or less, the solubilized protein was reprecipitated, and thus it became insolubilized.

Thus, refolding was attempted using gel filtration chromatography. The aim of this method is that, using gel with a small exclusion limit, the EcR recombinants that cannot be incorporated into the pores of the gel are eluted to an exclusion limit position. On the other hand, since urea has a low molecular weight, it can be incorporated into the pores of the gel, and thus it is eluted later than the EcR recombinants are. Thus, it was considered that urea can be eliminated from the solubilized EcR recombinant-urea solution, and that the EcR recombinants can be recovered in a solubilized state. Such a refolding reaction was carried out applying gel filtration chromatography. As a result, it was confirmed by SDS-PAGE that all the EcR recombinants were eluted to an exclusion limit position (FIG. 10).

Figure 11:
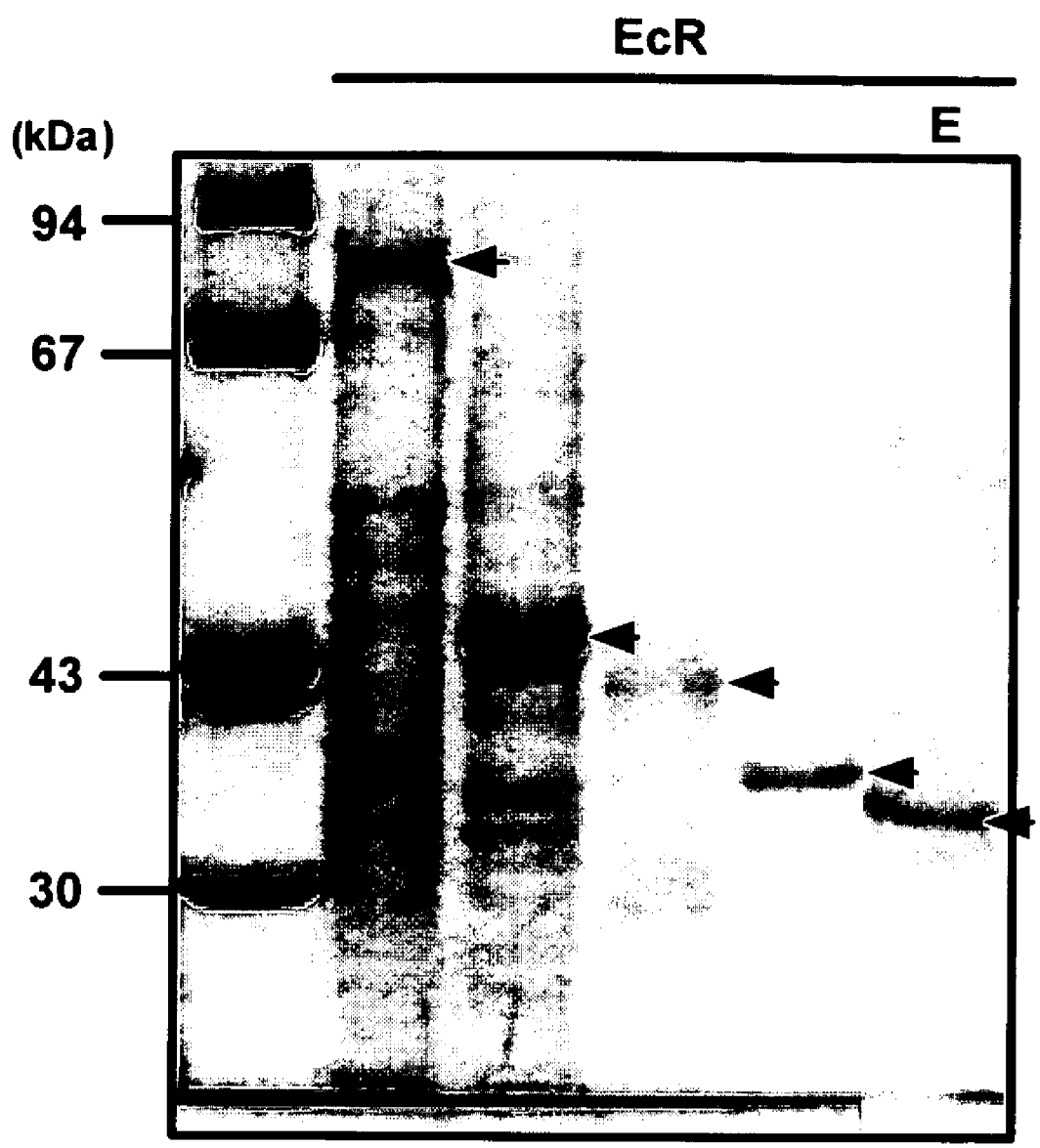
FIG. 11 is a photograph showing the results of SDS-PAGE performed on the purified EcR recombinant.

Each of the eluted EcR recombinants was concentrated by ultrafiltration. The concentration of this sample was quantified by the Bradford method. As a result, it was found that 186 μg of EcR-AF, 206 μg of EcR-DF, 98 μg of EcR-DE, 46 μg of EcR-EF, and 182 μg of EcR-E were obtained from 25 ml each of the culture solution. The thus purified EcR recombinant solution was subjected to SDS-PAGE. The results are shown in FIG. 11.

(USP Recombinant)

Figure 12A:
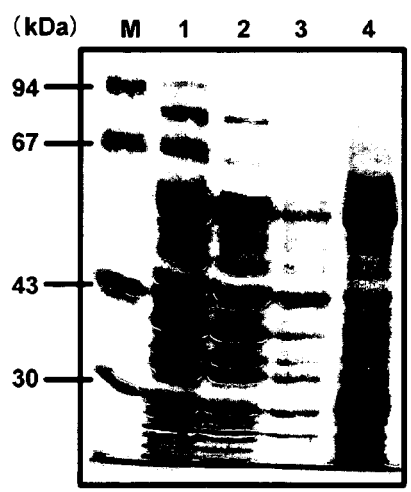
FIG. 12 includes several photographs showing the results of SDS-PAGE performed on each fraction obtained after affinity purification of USP recombinants.
Figure 12B:
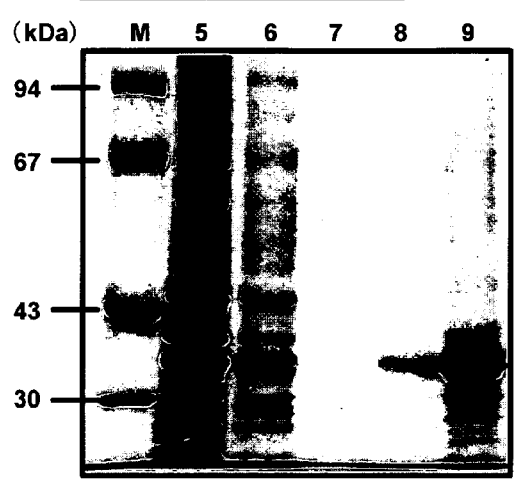
Figure 12C:
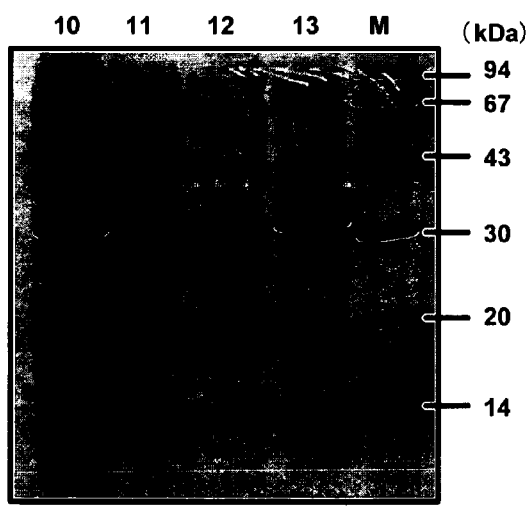

As stated above, several USP recombinants existed in a soluble fraction (refer to FIG. 7). Since a His-tag was added to the N-terminus of such a USP recombinant, the USP recombinant was subjected to affinity purification using a nickel resin (FIG. 12). It was concentrated by ultrafiltration, and was then quantified by the Bradford method. As a result, it was found that 814 μg of USP-AE, 417 μg of USP-DE, and 1.3 mg of USP-E were obtained from 100 ml each of the culture solution.

EXAMPLE 3

Expression of EcR Recombinant and USP Recombinant (Cultured Animal Cells)

In order to use as positive controls in Example 4 "Analysis of ability of EcR recombinant and USP recombinant to bind to ligand" described later, ill Example 3, the EcR recombinant and the USP recombinant were allowed to express in cultured animal cells, and extracts were prepared from the cells.

Figure 13:
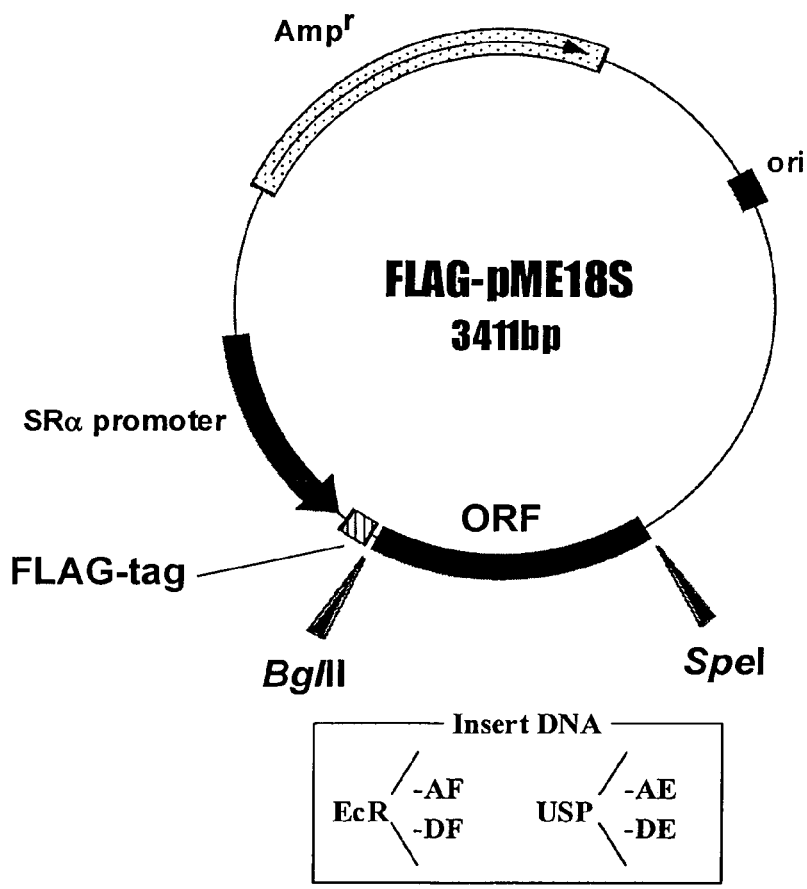
FIG. 13 is a block diagram showing an expression vector produced in Example 3 (SEQ ID NOS: 48-53)

COS-7 cells were used as cultured animal cells. As an expression plasmid used herein, EcR-AF, EcR-DF, USP-AE, or USP-DE was inserted into a position downstream of an SRα promoter, and a FLAG tag was then added to the N-terminus thereof (FIG. 13).

ECR-AF incorporated into this expression plasmid could be obtained by PCR using the plasmid used for cloning in Example 1 as a template and using a set of primers, EcR-Af and EcR-Fr. EcR-DF incorporated into the expression plasmid could be obtained by PCR using the plasmid used for cloning in Example 1 as a template and using a set of primers, EcR-Df and EcR-Fr. The nucleotide sequences of the primers EcR-Af, EcR-Df, and EcR-Fr are shown below.

```
EcR-Af:                               (SEQ ID NO: 48)
5'-CATTAGGATCCATGTCCATAGAGTCGCGTTTAG-3'

EcR-Df:                               (SEQ ID NO: 49)
5'-CATTAGGATCCAGGCCTGAGTGCGTGGTGCCT-3'

EcR-Fr:                               (SEQ ID NO: 50)
5'-GATTTACTAGTCTAGAGCGCCGCGCTTTCCG-3'
```

USP-AE incorporated into the expression plasmid could be obtained by PCR using the plasmid used for cloning in Example 1 as a template and using a set of primers, USP-Af and USP-Fr. USP-DE incorporated into the expression plasmid could be obtained by PCR using the plasmid used for cloning in Example 1 as a template and using a set of primers, USP-Df and USP-Er. The nucleotide sequences of the primers USP-Af, USP-Df, and USP-Er are shown below.

```
USP-Af:                               (SEQ ID NO: 51)
5'-ATAACGGATCCATGTCAGTGGCGAAGAAAGATAAG-3'

USP-Df:                               (SEQ ID NO: 52)
5'-ATTACGGATCCAAGAGGGAGGCAGTTCAAGAG-3'

USP-Er:                               (SEQ ID NO: 53)
5'-ATTACACTAGTTACATGACGTTGGCGTCGATG-3'
```

Each expression plasmid DNA was independently introduced into COS-7 cells. 48 hours later, each extract was prepared from the cells. In addition, plasmid DNA into which EcR-AF had been inserted and plasmid DNA into which USP-AE had been inserted were co-introduced into COS-7 cells, and an extract was then prepared in the same manner. Moreover, plasmid DNA into which, EcR-DF had been inserted and plasmid DNA into which USP-AE had been inserted were co-introduced into COS-7 cells, and an extract was then prepared in the same manner. Furthermore, plasmid DNA into which EcR-AF had been inserted and plasmid DNA into which USP-DE had been inserted were co-introduced into COS-7 cells, and an extract was then prepared in the same manner. Further, plasmid DNA into which EcR-DF had been inserted and plasmid DNA into which USP-DE had been inserted were co-introduced into COS-7 cells, and an extract was then prepared in the same manner. The expression of a product of interest in the COS-7 cells was confirmed by Western blotting using an anti-FLAG antibody.

By the aforementioned operations, 4 types of extracts containing each of EcR-AF, EcR-DF, USP-AE, and USP-DE, an extract containing the coexpressed EcR-AF and USP-AE, an extract containing the coexpressed EcR-DF and USP-AE, an extract containing the coexpressed EcR-AF and USP-DE, and an extract containing the coexpressed EcR-DF and USP-DE, were prepared.

Figure 14:
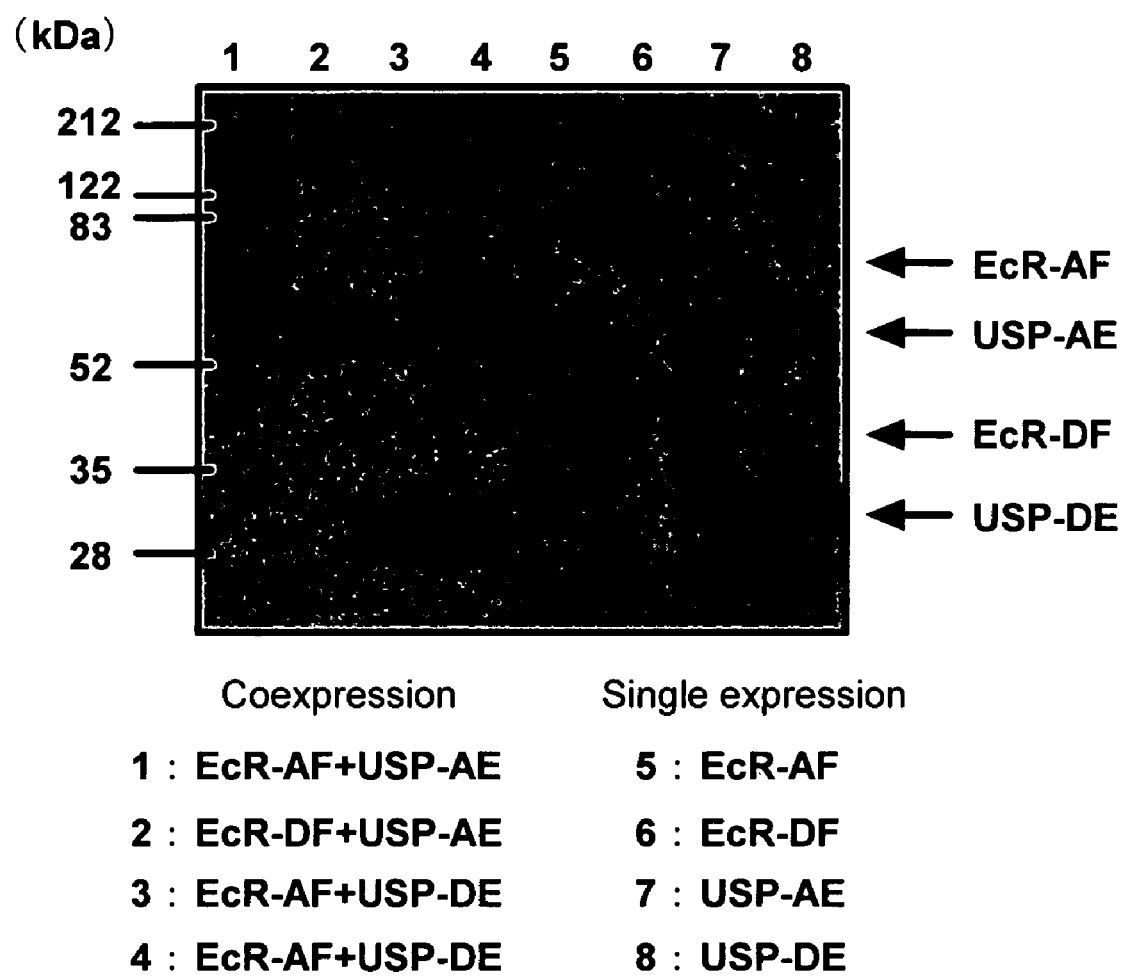
FIG. 14 is a photograph showing the results of Western blotting, which has been carried out to confirm the presence of an EcR recombinant in a system wherein the EcR recombinant has been allowed to express in mammalian cells.

Western blotting using an anti-FLAG antibody was performed on the obtained extracts, so as to confirm the expression of proteins of interest. The results are shown in FIG. 14. As shown in FIG. 14, the single expression and coexpression of proteins of interest were confirmed in all of the extracts.

EXAMPLE 4

Analysis of Ability of EcR Recombinant and USP Recombinant to Bind to Ligand

In Example 4, using the EcR recombinants and USP recombinants obtained in Examples 2 and 3, the ability of complexes consisting of these EcR recombinants and USP recombinants to bind to a ligand was analyzed. In the present example, ponasterone A, an ecdysone agonist derived from plants, was used as a ligand.

In Example 4, in order to separate a binding form from a free form, the charcoal dextran method was applied. This is a common method applied when a steroid hormone is used as a ligand. By adding an activated carbon solution coated with dextran to a reaction solution when the reaction is terminated, a ligand that has not bound to a receptor is adsorbed on the activated carbon. Thereafter, the reaction solution is centrifuged, thereby separating an activated carbon fraction (precipitate fraction) from a supernatant fraction in which a receptor/ligand complex exists.

Figure 15:
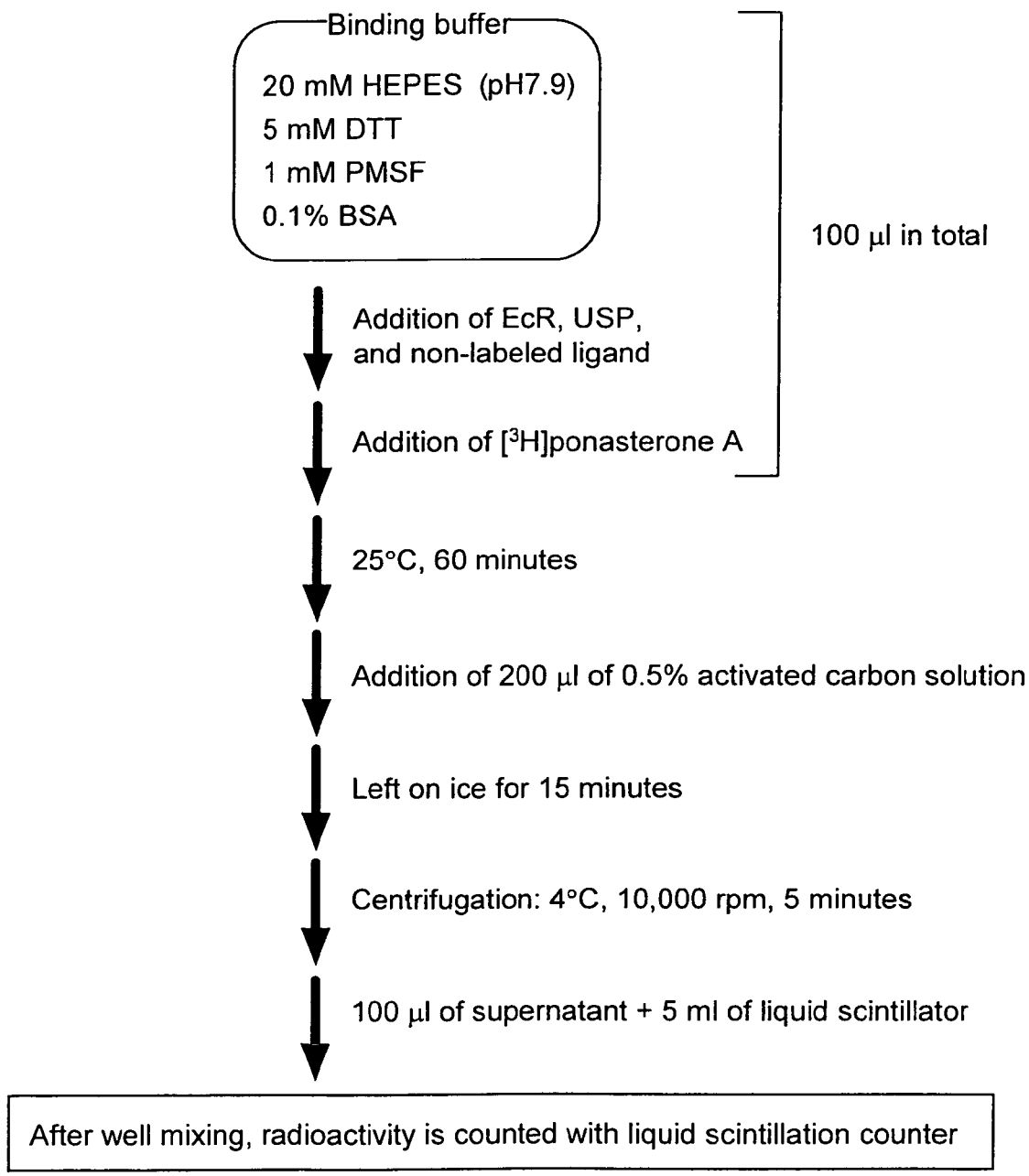
FIG. 15 is a flow chart showing the process of an experiment in Example 4.

The flow of the experiment in Example 4 is shown in FIG. 15. In order to prevent the non-specific binding of ponasterone A to a receptor (a complex consisting of an EcR recombinant and a USP recombinant), 1% BSA was first added to a binding buffer (20 mM HEPES (pH7.4)/5 mM DTT/1 nM PMSF). Thereafter, USP-AE or USP-DE was mixed with the EcR-AF, EcR-DF, EcR-DE, EcR-EF, or EcR-E, purified in Example 2. Thereafter, [$^3$H]ponasterone A ([24, 25, 26, 27-3H] Ponasterone A (American Radiolabeled Chemicals Inc.)) with a final concentration of 1.37 nM was further added thereto. The obtained mixture was reacted at 25° C. 40 minutes later, the reaction was terminated by addition of 200 μl of an activated carbon solution (0.5% Charcoal, dextran coated (SIGMA)/20 mm HEPES/50 mM NaCl). A supernatant fraction obtained after centrifugation was mixed with a liquid scintillator, and the radioactivity (DPM) of the obtained mixture was measured using a liquid scintillation counter (ALOKA LSC-5100). The obtained measurement value was defined as the total binding amount. Moreover, the same experiment was carried out with the exception that nonradioactive ponasterone A that was 10,000 times stronger than [$^3$H]ponasterone A was added. Then, the amount of a ligand non-specifically binding to a receptor was obtained. The amount of a ligand specifically binding to a receptor was defined as a value obtained by subtracting the non-specific binding amount from the total binding amount.

Figure 16:
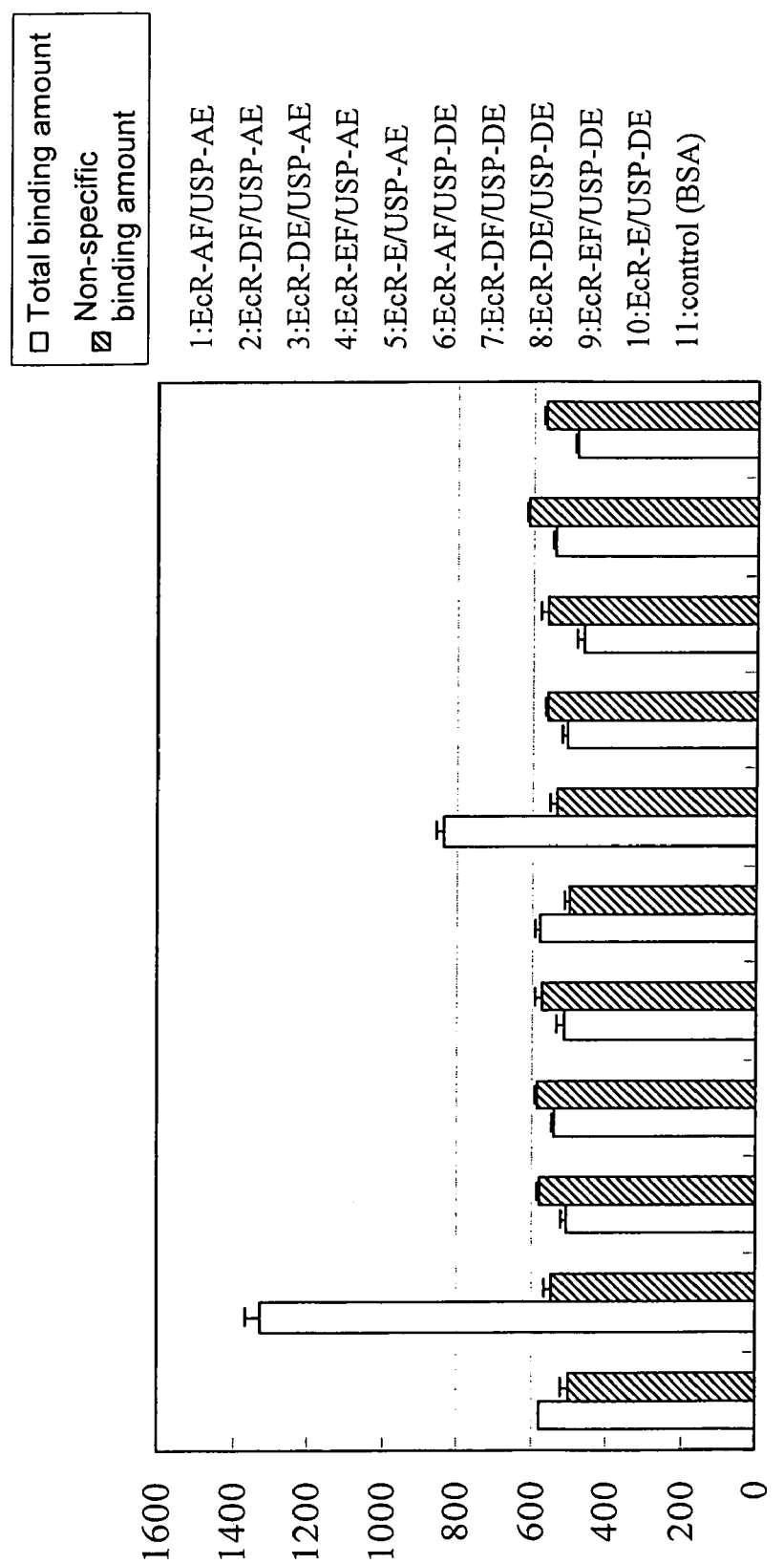
FIG. 16 is a characteristic diagram showing the results obtained by measuring the ability of EcR recombinants and USP recombinants, which have been allowed to express in *Escherichia coli*, to bind to ponasterone A.

The results are shown in FIG. 16. FIG. 16 shows that a complex consisting of EcR-DF and USP-AE and a complex consisting of EcR-DF and USP-DE had ability to bind to a ligand. On the other hand, in the single use of EcR or USP, no specific bindings were observed regardless of the length of EcR or USP.

Figure 17:
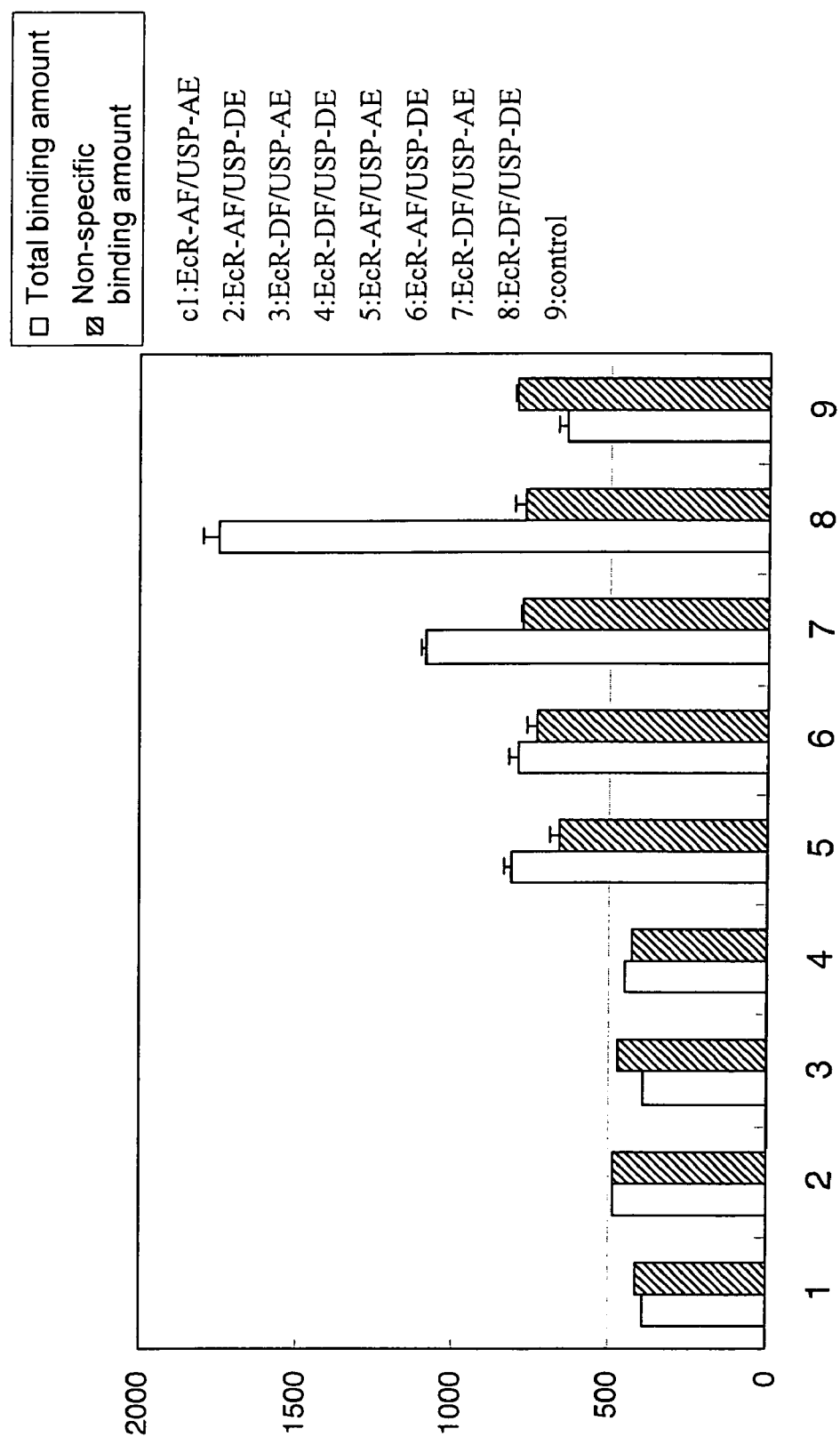
FIG. 17 is a characteristic diagram showing the results obtained by measuring the ability of EcR recombinants and USP recombinants, which have been allowed to express in mammalian cells, to bind to ponasterone A.

At the same time, the same binding experiment was carried out using the extracts prepared in Example 3. As a result, as shown in FIG. 17, when EcR-DF and USP-AE, or EcR-DF and USP-DE, were allowed to coexpress in cells, a strong binding to a ligand was observed (lanes 7 and 8). However, when each of the above combinations was allowed to singly express and they were then mixed with each other, no such bindings were observed (lanes 3 and 4). Moreover, when EcR-AF was combined with USP-AE or when EcR-AF was combined with USP-DE, no bindings to a ligand were observed both in the case of coexpression and in the case of mixing them after a single expression.

From the above results, it was found that since EcR-DF binds to ponasterone A, not only the region E, but also at least both the D region and F region should bind to ponasterone A. It has been suggested so far that the D region is associated with dimerization with USP. The results obtained in the present example strongly support that dimerization is essential for binding to a ligand. With regard to the F region, the length of the amino acids thereof is extremely short, conservativeness among various organisms is low, and the role of the structural chemical activity thereof is unclear under the present circumstances. It was at least found that the F region plays an important role for binding to a ligand.

In both an expression system using *Escherichia coli* and an expression system using mammalian cells, the binding of the full-length EcR recombinant (EcR-AF) to ponasterone A was observed, but it was extremely weak. Accordingly, in the present example, it was found for the first time that when a ligand binding to EcR is screened, it is necessary not to use the full-length EcR, but to use an EcR-DF recombinant.

EXAMPLE 5

Analysis of Conditions for Binding Experiment

Conditions such as molar ratio, reaction time, reaction temperature, and salt concentration are considered to be important for the interaction between a complex and a ligand. In order to more efficiently observe the binding of the aforementioned complex consisting of EcR-DF and USP-AE to a ligand, such conditions as molar ratio, reaction time, reaction temperature, and salt concentration will be analyzed in the Example 5.

Analysis of Molar Ratio Between EcR-DF and USP-AE

Figure 18:
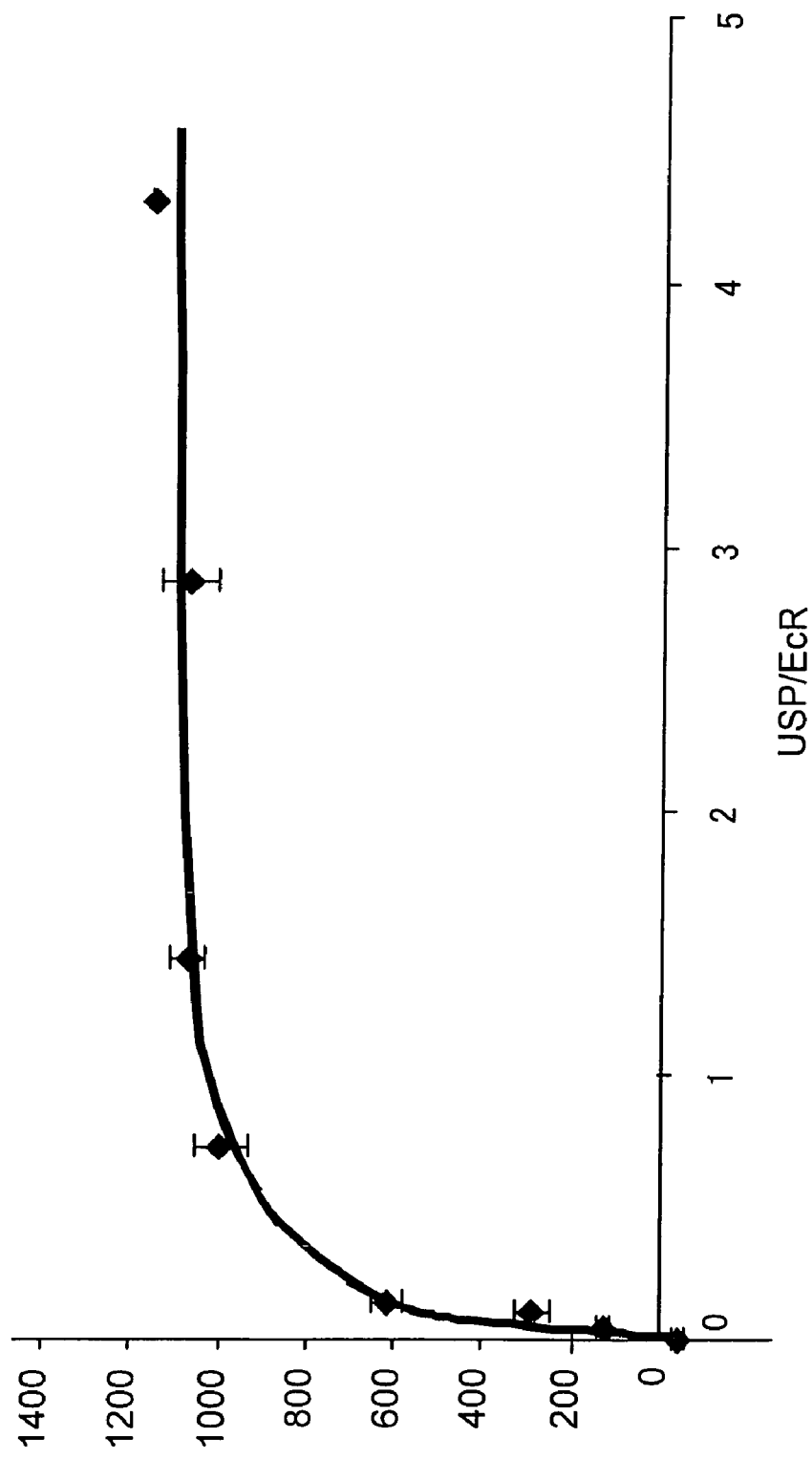
FIG. 18 is a characteristic diagram showing the results obtained by examining the optimal molar ratio between EcR-DF and USP-AE in a binding reaction between an EcR-DF/USP-AE complex and a ligand.

The optimal reaction time for a binding reaction between a complex consisting of EcR-DF and USP-AE and a ligand was analyzed as follows. First, USP-AE with various types of concentrations was added to a certain amount of EcR-DF, and the obtained mixture was then reacted at 25° C. for 40 minutes in a water bath. The concentration of ponasterone A in the reaction solution was set at 1.34 nM. The results obtained by measuring the binding of ponasterone A to the complex are shown in FIG. 18. As is clear from FIG. 18, when the ratio between EcR-DF and USP-AE was approximately 1:1, the binding of ponasterone A to the EcR-DF/USP-AE complex became saturated. From these results, it is said that the ratio between EcR-DF and USP-AE is preferably set at 1:1, at a molar ratio, for the binding reaction of the EcR-DF/USP-AE complex to a ligand. It is to be noted that EcR-DF and USP-AE were used at a molar ratio of 1:1 in the subsequent experiments.

Analysis of Reaction Time

Figure 19:
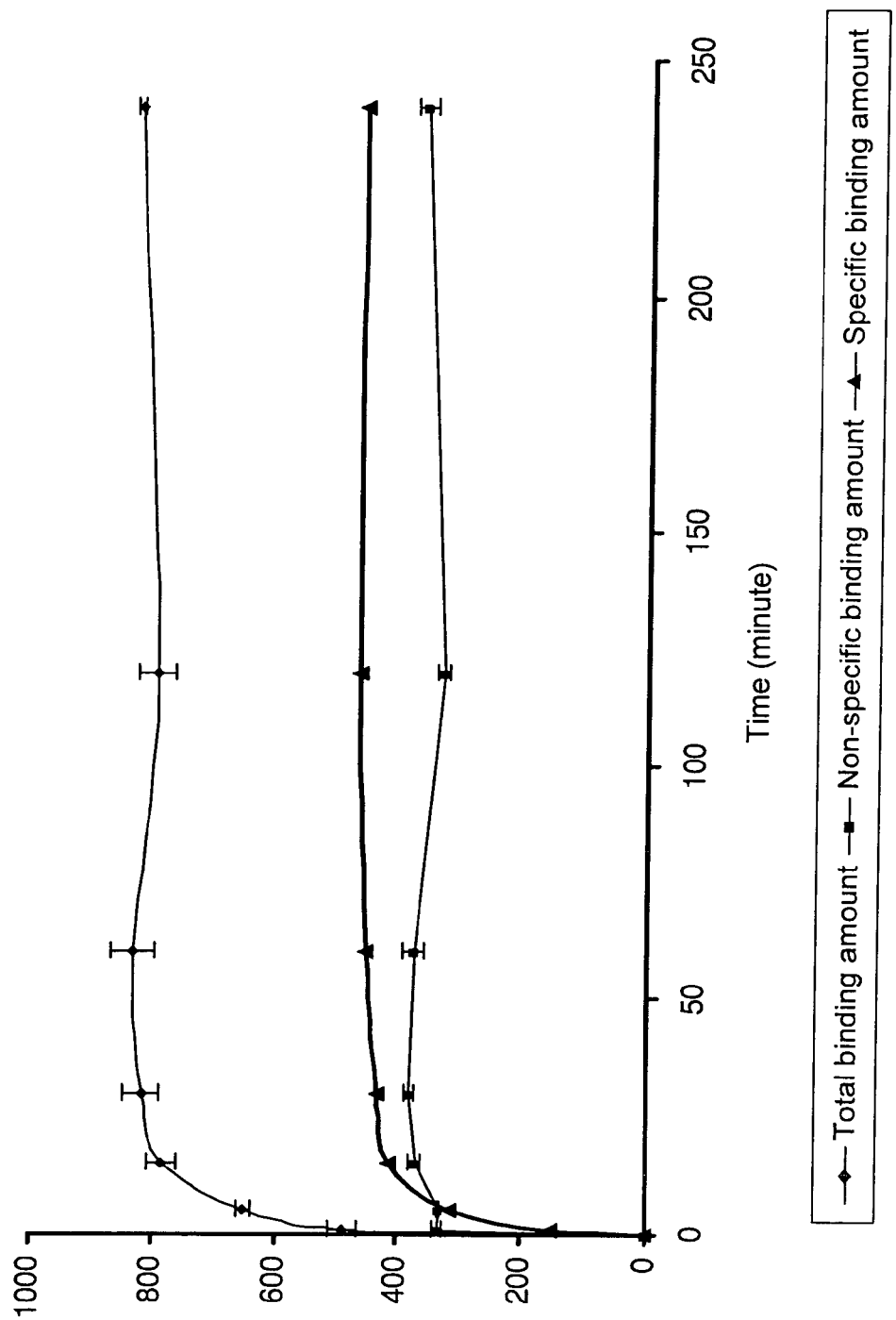
FIG. 19 is a characteristic diagram showing the results obtained by examining the optimal reaction time, with regard to a binding reaction between an EcR-DF/USP-AE complex and a ligand.

The optimal reaction time for a binding reaction between a complex consisting of EcR-DF and USP-AE and a ligand was analyzed as follows. First, EcR-DF was mixed with USP-AE at a molar ratio of 1:1, and the obtained mixture was then reacted at 25° C. in a water bath for a period of time of 5 minute, 5 minutes, 15 minutes, 30 minutes, 60 minutes, 120 minutes, and 240 minutes. The concentration of ponasterone A in the reaction solution was set at 1.34 nM. The results are shown in FIG. 19. As is clear from FIG. 19, the binding of ponasterone A to the above complex became almost saturated in the reaction for 60 minutes. From these results, it is said that the reaction time is preferably set between 30 and 90 minutes for the binding reaction of the EcR-DF/USP-AE complex to a ligand. It is to be noted that the reaction time was set at 60 minutes in the subsequent experiments.

Analysis of Reaction Temperature

Figure 20:
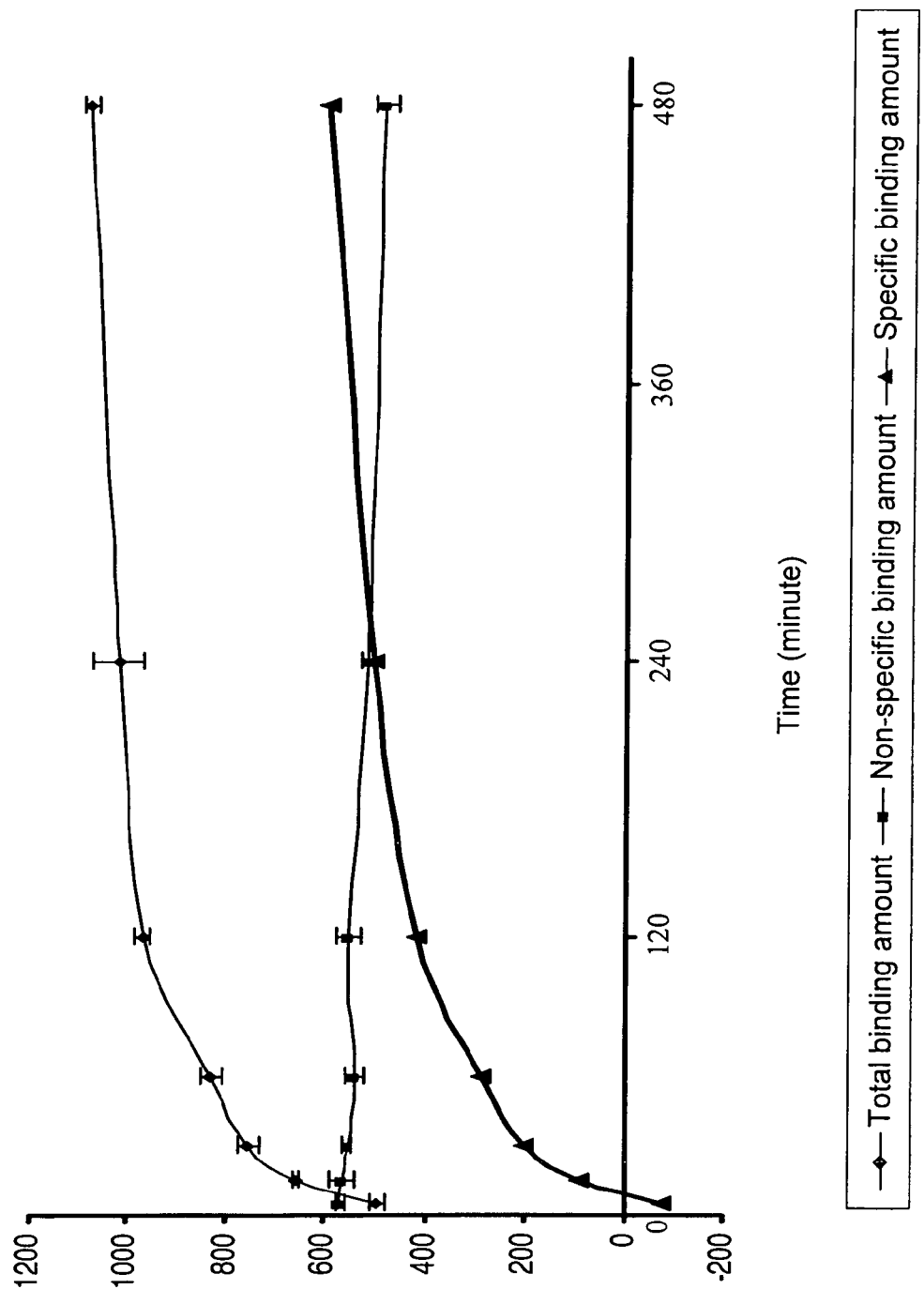
FIG. 20 is a characteristic diagram showing the results obtained by examining the optimal reaction temperature, with regard to a binding reaction between an EcR-DF/USP-AE complex and a ligand.

The optimal reaction temperature for a binding reaction between a complex consisting of EcR-DF and USP-AE and a ligand was analyzed as follows. The same binding reaction as described in the above section "analysis of reaction time" was carried out with the exception that the reaction was carried out in a low-temperature chamber at 4° C. The results are shown in FIG. 20. As is clear from FIG. 20, the time necessary for saturation of the binding was 8 hours in the low-temperature chamber at 4° C. In contrast, as shown in FIG. 20, the time necessary for saturation of the binding was 60 minutes at a reaction temperature of 25° C. From these results, it is said that the reaction temperature is preferably set between 20° C. and 37° C. for the binding reaction of the EcR-DF/USP-AE complex to a ligand. It is to be noted that the reaction temperature was set at 25° C. in the subsequent experiments.

Analysis of Salt Concentration

Figure 21:
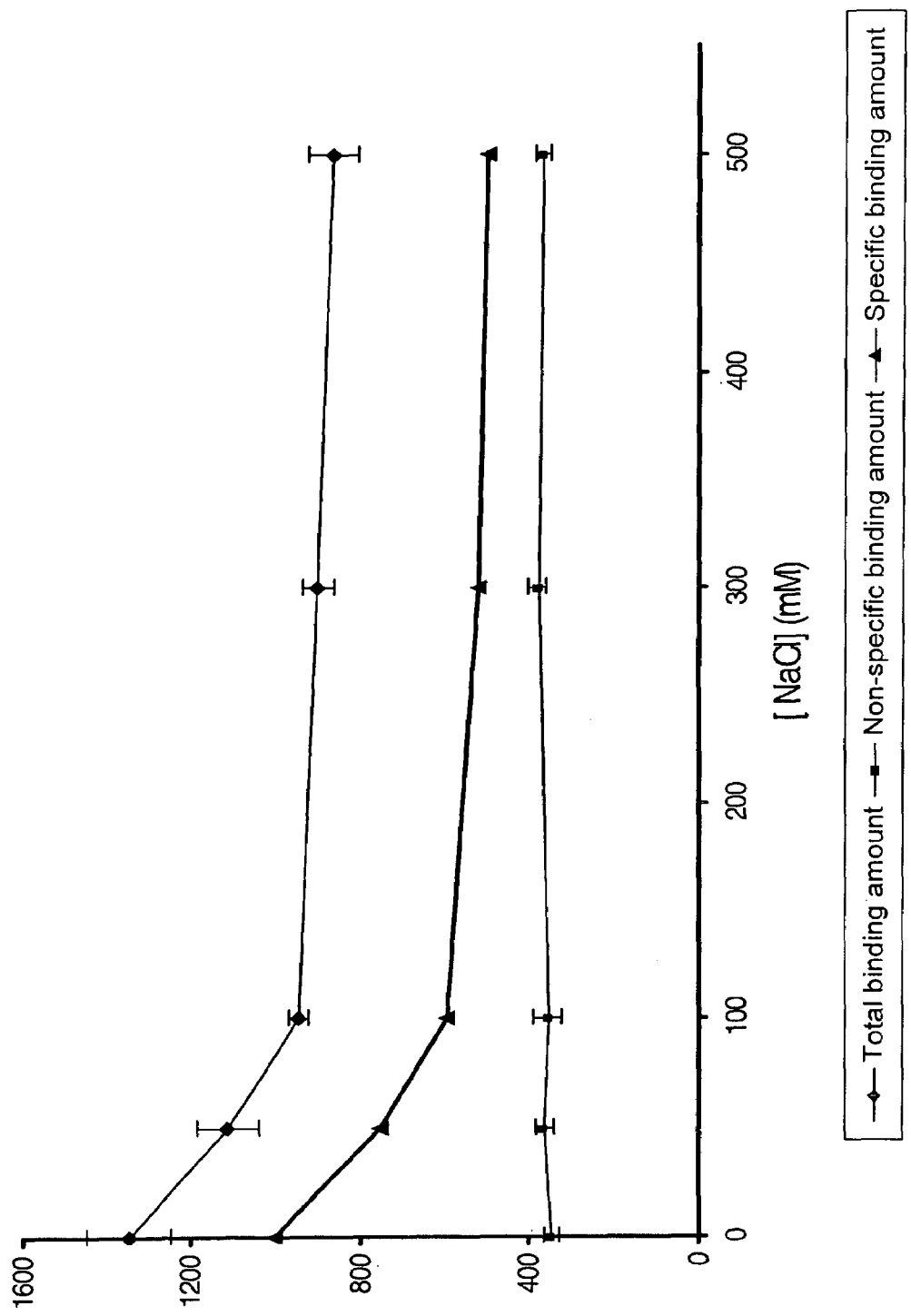
FIG. 21 is a characteristic diagram showing the results obtained by examining the optimal salt concentration, with regard to a binding reaction between an EcR-DF/USP-AE complex and a ligand.

The optimal salt concentration for a binding reaction between a complex consisting of EcR-DF and USP-AE and a ligand was analyzed as follows. First, EcR-DF was mixed with USP-AE at a molar ratio of 1:1, and the obtained mixture was then reacted at 25° C. in a water bath. During this reaction, the salt (NaCl) concentration was set at final concentrations of 0 mM, 50 mM, 100 mM, 300 mM, and 500 mM in the reaction solution. The results are shown in FIG. 21. As is clear from FIG. 21, as the salt concentration increased, the specific binding of a ligand to the above complex decreased. From these results, it is said that the salt concentration is preferably set between 0 and 100 mM for the binding reaction of the EcR-DF/USP-AE complex to a ligand. It is to be noted that no salts were added to the reaction solution in the subsequent experiments.

EXAMPLE 6

Scatchard Analysis of Binding of Complex to Ligand

Figure 22:
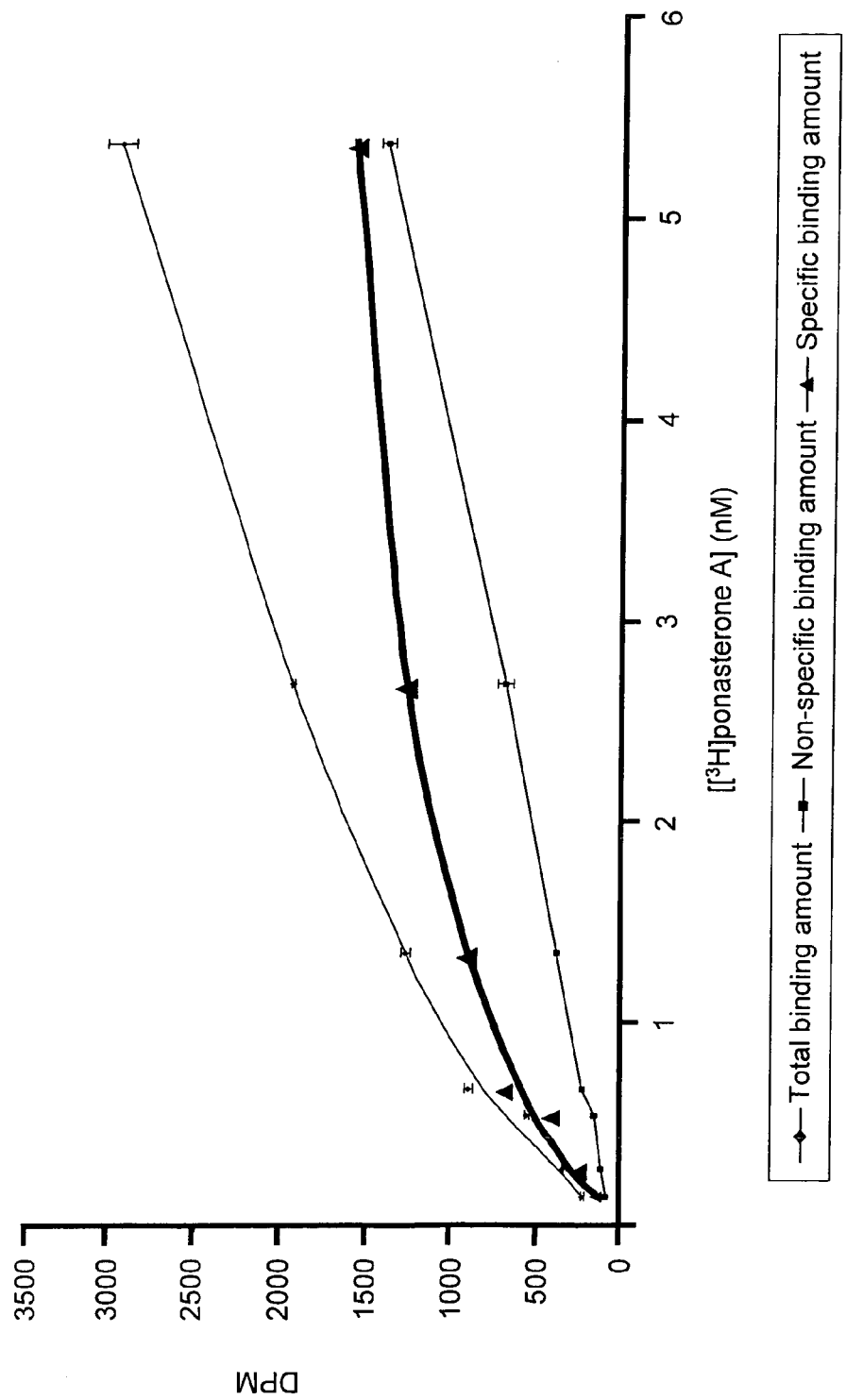
FIG. 22 is a characteristic diagram showing a binding curve in a binding reaction between an EcR-DF/USP-AE complex and a ligand.
Figure 23:
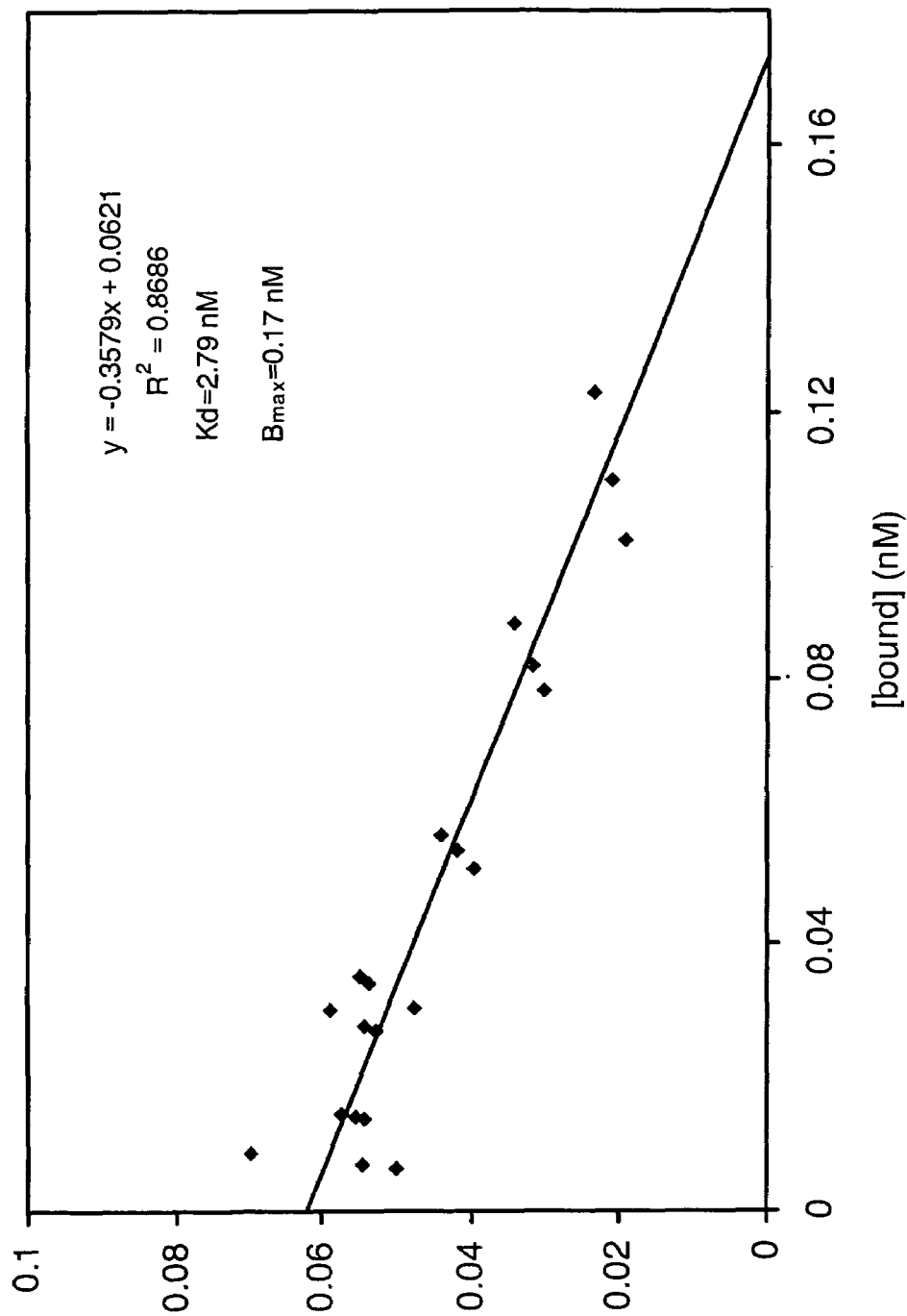
FIG. 23 is a characteristic diagram showing the results of Scatchard analysis performed on a binding reaction between an EcR-DF/USP-AE complex and a ligand.

In Example 6, using EcR-DF and USP-AE, the dissociation constant (Kd) of the complex to ponasterone A was obtained as follows. First, EcR-DF was mixed with USP-AE at a molar ratio of 1:1, and [$^3$H]ponasterone A with various concentrations was then added to the mixture. An activated carbon solution was added to the reaction solution to eliminate free ligands. The amount of the EcR-DF/USP-AE complex binding to [$^3$H]ponasterone A (total binding amount) was obtained by measuring the radioactivity of a supernatant fraction obtained after centrifugation. Moreover, the same experiment was carried out with the exception that nonradioactive ponasterone A that was 10,000 times stronger than [$^3$H]ponasterone A was added, so as to obtained non-specific binding. The results obtained by plotting the binding curve based on the measurement results are shown in FIG. 22. Scatchard analysis was carried out based on the values in the binding curve as shown in FIG. 22. The results are shown in FIG. 23. In FIG. 23, the horizontal axis indicates the specific bound amount of [$^3$H]ponasterone A (nM), the vertical axis indicates specific binding amount (bound)/total binding amount-specific binding amount (free).

As is clear from FIG. 23, as a result of the Scatchard analysis, a single line was obtained, and Kd=2.79 nM and Bmax=0.17 nM.

EXAMPLE 7

Construction of Screening System for Insect Inhibitor

In Example 7, a screening system used for screening an insect inhibitor was constructed based on the results of Examples 1 to 6. As described in Examples 1 to 6, when binding analysis was carried out using ponasterone A as an ecdysone agonist, ponasterone A binding to a complex consisting of EcR-DF and USP-AE was observed. In order to confirm whether or not this system functions as a screening system, the binding of the complex to other ecdysone agonists should also be observed. Thus, using 20-hydroxyecdysone that is an ecdysone active in living insect bodies and tebufenozide (RH-5992) that is a synthetic ecdysone agonist, the binding experiment was carried out between the EcR-EF/USP-AE complex and each of the above compounds.

Figure 24:
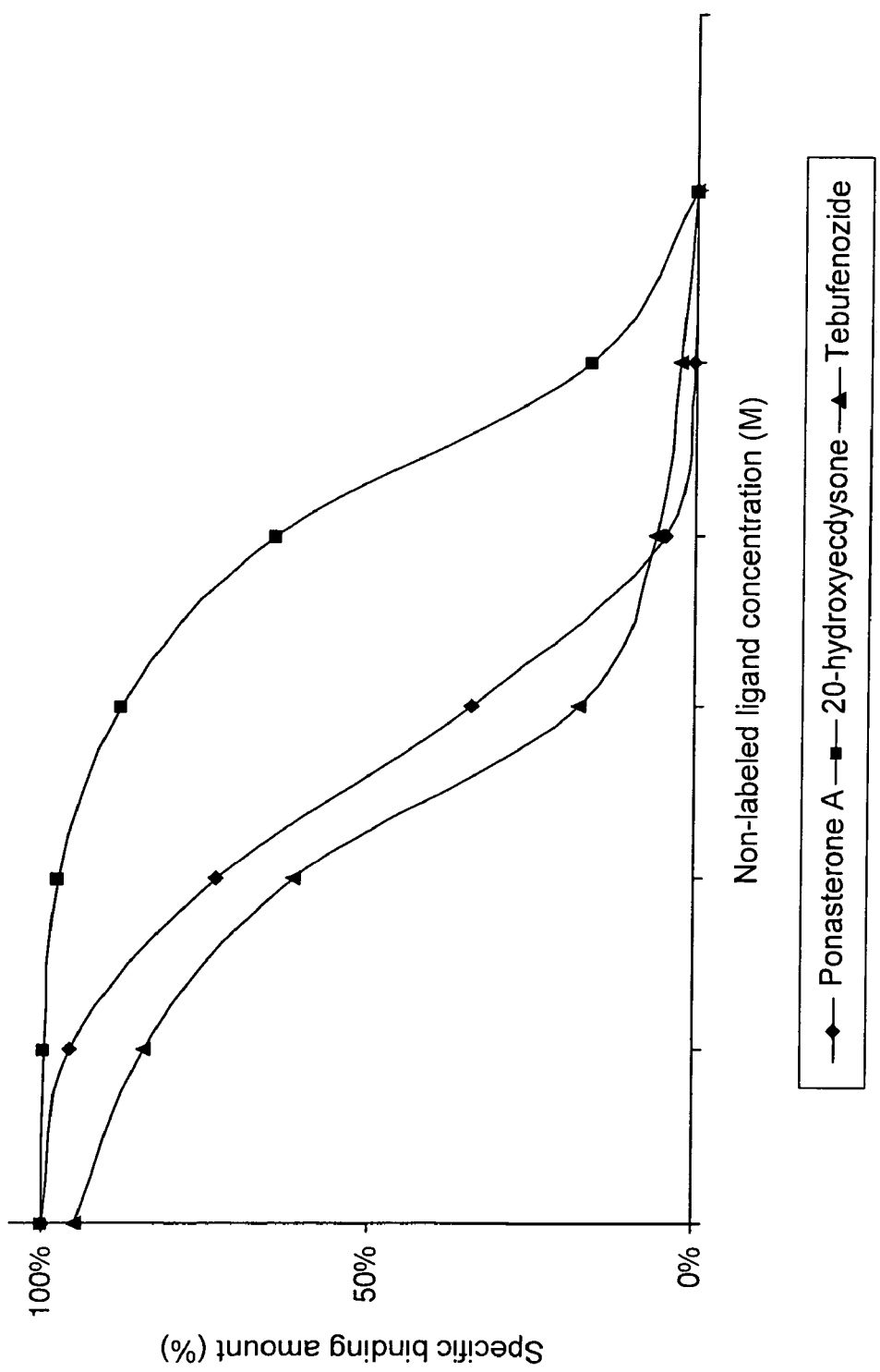
FIG. 24 is a characteristic diagram showing the results obtained by analyzing the binding of each of ecdysone and an ecdysone agonist to an EcR-DF/USP-AE complex.

First, EcR-DF and USP-AE were mixed into a binding buffer, and [$^3$H]ponasterone A was then added thereto in the same manner as in Example 4. Also, the same experiment was carried out with the exception that 20-hydroxyecdysone or tebufenozide that was 10,000 times stronger than [$^3$H]ponasterone A was added thereto, so as to obtain nonspecific binding. As a result, both 20-hydroxyecdysone and tebufenozide exhibited activity of binding to the EcR-EF/USP-AE complex. Thus, the same experiment was carried out while the concentration of 20-hydroxyecdysone or tebufenozide was changed. The results are shown in FIG. 24. As is clear from FIG. 24, it was found that both 20-hydroxyecdysone and tebufenozide concentration-dependently inhibit the binding of [$^3$H]ponasterone A to the above complex.

From these results, it was found that the binding experiment using EcR-DF and USP-AE can be used as a screening system for screening an insect growth inhibitor.

Subsequently, in the present example, using a screening system in which ability to bind to the EcR-DF/USP-AE complex is used as an index, 4 types of compounds were evaluated in terms of such binding ability. As compounds to be evaluated, 4-nonylphenol, stilbestrol, and diethyl phthalate (endocrine disrupters), and estradiol-17β (female hormone) were used.

Figure 25:
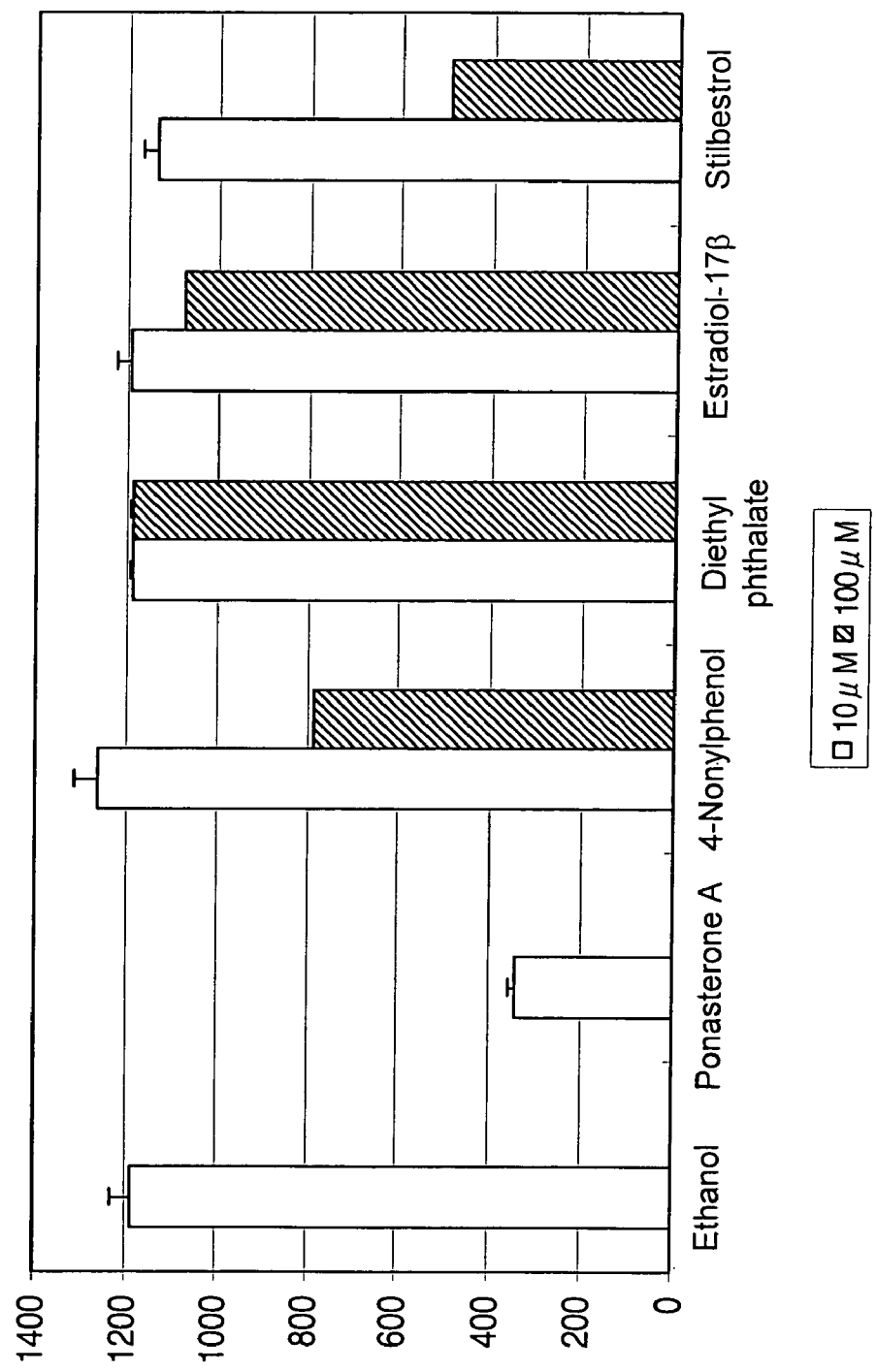
FIG. 25 is a characteristic diagram showing the results obtained by analyzing the binding of an EcR-DF/USP-AE complex to each of endocrine disrupters and a female hormone.

The results are shown in FIG. 25. As is clear from FIG. 25, 4-nonylphenol, stilbestrol, and estradiol-17β exhibited activity of binding to the EcR-DF/USP-AE complex. In particular, 4-nonylphenol and stilbestrol exhibited strong binding activity. It has been known so far that EcR basically binds to compounds having a steroid skeleton, such as ponasterone A. On the other hand, compounds having no steroid skeletons to which EcR binds have been limited to several types. All the substances exhibiting binding activity in the present example have no steroid skeletons, and further, the fact that the substance binds to EcR has not yet been known. From these results, it is said that a screening system, in which EcR-DF and USP-AE or USP-DE expressed in *Escherichia coli* are used, could be established as a novel system for searching for an insect growth inhibitor.

INDUSTRIAL APPLICABILITY

As stated above in detail, the present invention provides a completely novel molting hormone receptor capable of binding to an insect molting hormone. In addition, according to the present invention, a substance that can be applied to a disinfectant or the like can efficiently be screened using the above molting hormone receptor.

All publications, patents and patent applications cited herein are incorporated herein by reference in their entirety.

The invention claimed is:

1. An isolated insect molting hormone receptor comprising the following polypeptide (a) and polypeptide (b) or (c):
 (a) a polypeptide, which has the amino acid sequence shown in SEQ ID NO: 1, or a polypeptide, which has an amino acid sequence comprising a deletion, substitution, or addition of up to 10 amino acids with respect to the amino acid sequence shown in SEQ ID NO: 1, wherein the polypeptide forms a complex together with the following polypeptide (b) or (c), and the complex is capable of binding to a molting hormone;
 (b) a polypeptide, which has the amino acid sequence shown in SEQ ID NO: 2, or a polypeptide, which has an amino acid sequence comprising a deletion, substitution, or addition of up to 2 amino acids with respect to the amino acid sequence shown in SEQ ID NO: 2, and which may form a complex together with the polypeptide (a); or
 (c) a polypeptide, which has the amino acid sequence shown in SEQ ID NO: 3, or a polypeptide, which has an amino acid sequence comprising a deletion, substitution, or addition of up to 10 amino acids with respect to the amino acid sequence shown in SEQ ID NO: 3, and which may form a complex together with the polypeptide (a).

2. The isolated insect molting hormone receptor according to claim 1, wherein the polypeptides (a), (b), and (c) are expressed in *Escherichia coli*.

3. The isolated insect molting hormone receptor according to claim 1, wherein the polypeptide (a) is allowed to express in *Escherichia coli*, and is then solubilized such that the polypeptide (a) has activity of binding to the polypeptide (b) or (c).

4. A method for screening a ligand binding to a molting hormone receptor, which comprises:
contacting a test substance with insect molting hormone receptor according to any one of claims 1 to 3; and
measuring the binding of the complex to the test substance.

5. The method for screening a ligand binding to a molting hormone receptor according to claim 4, wherein the insect molting hormone receptor is mixed with the test substance, and the mixture is then reacted for 30 to 90 minutes.

6. The method for screening a ligand binding to a molting hormone receptor according to claim 4, wherein the insect molting hormone receptor is mixed with the test substance, and the mixture is then reacted at a temperature between 20° C. and 37° C.

7. The method for screening a ligand binding to a molting hormone receptor according to claim 4, wherein the insect molting hormone receptor is mixed with the test substance, and the mixture is then reacted under conditions wherein the mixture is substantially free of salts.

8. The isolated insect molting hormone receptor according to claim 1, wherein polypeptide (a) has an amino acid sequence comprising a deletion, substitution, or addition of up to 5 amino acids and forms a complex together with polypeptides (b) or (c) and wherein the complex is capable of binding to a molting hormone.

9. The isolated insect molting hormone receptor according to claim 1, wherein polypeptide (a) has an amino acid sequence comprising a deletion, substitution, or addition of up to 1 amino acid and forms a complex together with polypeptides (b) or (c) and wherein the complex is capable of binding to a molting hormone.

10. The isolated insect molting hormone receptor according to claim 1, wherein polypeptide (a) has an amino acid sequence comprising SEQ ID NO:1 and wherein said polypeptide forms a complex together with polypeptides (b) or (c) and wherein the complex is capable of binding to a molting hormone.

11. The isolated insect molting hormone receptor according to claim 1, wherein polypeptide (b) has an amino acid sequence comprising a deletion, substitution, or addition of up to 1 amino acid and may form a complex together with the polypeptide (a).

12. The isolated insect molting hormone receptor according to claim 1, wherein polypeptide (b) has an amino acid sequence comprising SEQ ID NO:2 and may form a complex together with the polypeptide (a).

13. The isolated insect molting hormone receptor according to claim 1, wherein polypeptide (c) has an amino acid sequence comprising a deletion, substitution, or addition of up to 5 amino acids and may form a complex together with the polypeptide (a).

14. The isolated insect molting hormone receptor according to claim 1, wherein polypeptide (c) has an amino acid sequence comprising a deletion, substitution, or addition of up to 1 amino acid and may form a complex together with the polypeptide (a).

15. The isolated insect molting hormone receptor according to claim 1, wherein polypeptide (c) has an amino acid sequence comprising SEQ ID NO:3 and may form a complex together with the polypeptide (a).

* * * * *